(12) United States Patent
You et al.

(10) Patent No.: US 10,232,082 B2
(45) Date of Patent: Mar. 19, 2019

(54) IMPLANTABLE SCAFFOLDS FOR TREATMENT OF SINUSITIS

(71) Applicant: 480 Biomedical, Inc., Watertown, MA (US)

(72) Inventors: Changcheng You, Northbridge, MA (US); Quynh Pham, Methuen, MA (US); Danny Concagh, Medfield, MA (US)

(73) Assignee: 480 Biomedical, Inc., Watertown, MA (US)

( * ) Notice: Subject to any disclaimer, the term of this patent is extended or adjusted under 35 U.S.C. 154(b) by 0 days.

(21) Appl. No.: 15/492,103

(22) Filed: Apr. 20, 2017

(65) Prior Publication Data
US 2017/0224476 A1    Aug. 10, 2017

Related U.S. Application Data

(63) Continuation-in-part of application No. 15/197,686, filed on Jun. 29, 2016.
(Continued)

(51) Int. Cl.
| | |
|---|---|
| A61F 2/18 | (2006.01) |
| A61L 27/34 | (2006.01) |
| A61M 25/10 | (2013.01) |
| A61M 31/00 | (2006.01) |
| A61L 27/54 | (2006.01) |
| A61K 31/58 | (2006.01) |
| A61L 27/58 | (2006.01) |
| A61L 27/18 | (2006.01) |
| A61L 27/56 | (2006.01) |
| A61F 2/90 | (2013.01) |

(52) U.S. Cl.
CPC .............. *A61L 27/34* (2013.01); *A61F 2/186* (2013.01); *A61F 2/90* (2013.01); *A61K 31/58* (2013.01); *A61L 27/18* (2013.01); *A61L 27/54* (2013.01); *A61L 27/56* (2013.01); *A61L 27/58* (2013.01); *A61M 25/10* (2013.01); *A61M 31/002* (2013.01); *A61F 2210/0004* (2013.01); *A61F 2250/0031* (2013.01); *A61F 2250/0067* (2013.01); *A61L 2300/222* (2013.01); *A61L 2300/41* (2013.01); *A61L 2300/604* (2013.01); *A61L 2300/608* (2013.01); *A61M 2025/105* (2013.01); *A61M 2210/0681* (2013.01)

(58) Field of Classification Search
CPC ...... A61F 2/18; A61F 2/186; A61F 2210/004; A61F 2250/0067; A61F 2250/001; A61F 2210/0057; A61L 27/54; A61L 27/34; A61L 31/06; A61L 31/10; A61L 31/148; A61L 31/16
See application file for complete search history.

(56) References Cited

U.S. PATENT DOCUMENTS

| | | | |
|---|---|---|---|
| 4,886,062 A | 12/1989 | Wiktor | |
| 5,133,732 A | 7/1992 | Wiktor | |

(Continued)

FOREIGN PATENT DOCUMENTS

WO    2009079418 A2    6/2009

*Primary Examiner* — Paul B Prebilic
(74) *Attorney, Agent, or Firm* — Medlen and Carroll, LLP

(57) ABSTRACT

This disclosure describes, inter alia, materials, devices, kits and methods that may be used to treat chronic sinusitis. More specifically, a drug-eluting scaffold is implanted in the middle meatus to treat chronic sinusitis for weeks to months.

47 Claims, 17 Drawing Sheets

Related U.S. Application Data

(60) Provisional application No. 62/332,134, filed on May 5, 2016, provisional application No. 62/289,982, filed on Feb. 2, 2016, provisional application No. 62/186,030, filed on Jun. 29, 2015.

(56) References Cited

U.S. PATENT DOCUMENTS

| | | |
|---|---|---|
| 5,170,802 A | 12/1992 | Mehra |
| 5,224,491 A | 7/1993 | Mehra |
| 5,265,601 A | 11/1993 | Mehra |
| 5,336,163 A | 8/1994 | DeMane et al. |
| 5,447,724 A | 9/1995 | Helmus |
| 5,464,650 A | 11/1995 | Berg |
| 5,591,198 A | 1/1997 | Boyle et al. |
| 5,613,981 A | 3/1997 | Boyle et al. |
| 5,653,727 A | 8/1997 | Wiktor |
| 5,897,521 A | 4/1999 | Lavigne |
| 5,899,934 A | 5/1999 | Amundson et al. |
| 5,913,896 A | 6/1999 | Boyle et al. |
| 6,047,431 A | 4/2000 | Canonica |
| 6,153,252 A * | 11/2000 | Hossainy .............. A61F 2/82 427/2.25 |
| 6,161,029 A | 12/2000 | Spreigl et al. |
| 6,240,616 B1 * | 6/2001 | Yan .............. A61F 2/91 29/527.2 |
| 6,301,507 B1 | 10/2001 | Bakels et al. |
| 6,330,481 B1 | 12/2001 | Van Wijk et al. |
| 6,346,116 B1 | 2/2002 | Brooks et al. |
| 6,385,491 B1 | 5/2002 | Lindemans et al. |
| 6,449,507 B1 | 9/2002 | Hill et al. |
| 6,487,446 B1 | 11/2002 | Hill et al. |
| 6,532,388 B1 | 3/2003 | Hill et al. |
| 6,543,452 B1 | 4/2003 | Lavigne |
| 6,628,987 B1 | 9/2003 | Hill et al. |
| 6,718,208 B2 | 4/2004 | Hill et al. |
| 6,770,080 B2 | 8/2004 | Kaplan et al. |
| 6,863,684 B2 | 3/2005 | Kim et al. |
| 6,904,318 B2 | 6/2005 | Hill et al. |
| 6,909,920 B2 | 6/2005 | Lokhoff et al. |
| 6,923,828 B1 | 8/2005 | Wiktor |
| 6,945,992 B2 | 9/2005 | Goodson, IV et al. |
| 7,184,828 B2 | 2/2007 | Hill et al. |
| 7,184,829 B2 | 2/2007 | Hill et al. |
| 7,323,008 B2 | 1/2008 | Kantor et al. |
| 7,356,903 B2 | 4/2008 | Krivoruchko et al. |
| 7,361,168 B2 | 4/2008 | Makower et al. |
| 7,386,351 B2 | 6/2008 | Hine et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,547,323 B2 | 6/2009 | Lavigne |
| 7,559,925 B2 | 7/2009 | Goldfarb et al. |
| 7,578,899 B2 | 8/2009 | Edwin et al. |
| 7,615,072 B2 | 11/2009 | Rust et al. |
| 7,641,644 B2 | 1/2010 | Chang et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,662,141 B2 | 2/2010 | Eaton et al. |
| 7,662,142 B2 | 2/2010 | Eaton et al. |
| 7,678,099 B2 | 3/2010 | Ressemann et al. |
| 7,686,798 B2 | 3/2010 | Eaton et al. |
| 7,691,094 B2 | 4/2010 | Eaton et al. |
| 7,697,972 B2 | 4/2010 | Verard et al. |
| 7,704,259 B2 | 4/2010 | Kaplan et al. |
| 7,713,255 B2 | 5/2010 | Eaton et al. |
| 7,717,933 B2 | 5/2010 | Becker |
| 7,717,955 B2 | 5/2010 | Lane et al. |
| 7,720,521 B2 | 5/2010 | Chang et al. |
| 7,727,186 B2 | 6/2010 | Makower et al. |
| 7,727,226 B2 | 6/2010 | Chang et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,803,150 B2 | 9/2010 | Chang et al. |
| 7,806,919 B2 | 10/2010 | Bloom et al. |
| 7,815,673 B2 | 10/2010 | Bloom et al. |
| 7,842,062 B2 | 11/2010 | Keith et al. |
| 7,854,744 B2 | 12/2010 | Becker |
| 7,951,131 B2 | 1/2011 | Eaton et al. |
| 7,879,061 B2 | 2/2011 | Keith et al. |
| 7,914,639 B2 | 3/2011 | Layne et al. |
| 7,951,130 B2 | 3/2011 | Eaton et al. |
| 7,918,871 B2 | 4/2011 | Truitt et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 7,955,346 B2 | 6/2011 | Mauch et al. |
| 7,967,807 B2 | 6/2011 | Murray |
| 7,967,857 B2 | 6/2011 | Lane |
| 7,972,378 B2 | 7/2011 | Tabor et al. |
| 7,993,350 B2 | 8/2011 | Ventura et al. |
| 7,993,675 B2 | 8/2011 | Oliver et al. |
| 8,025,635 B2 | 9/2011 | Eaton et al. |
| 8,034,099 B2 | 10/2011 | Pellegrini |
| 8,046,052 B2 | 10/2011 | Verard et al. |
| 8,052,693 B2 | 11/2011 | Shahoian |
| 8,052,750 B2 | 11/2011 | Tuval et al. |
| 8,088,101 B2 | 1/2012 | Chang et al. |
| 8,100,933 B2 | 1/2012 | Becker |
| 8,109,918 B2 | 2/2012 | Eaton et al. |
| 8,114,062 B2 | 2/2012 | Muni et al. |
| 8,114,113 B2 | 2/2012 | Becker |
| 8,118,757 B2 | 2/2012 | Morriss |
| 8,123,722 B2 | 2/2012 | Chang et al. |
| 8,126,549 B2 | 2/2012 | Sigg et al. |
| 8,142,422 B2 | 3/2012 | Makower et al. |
| 8,146,400 B2 | 4/2012 | Goldfarb et al. |
| 8,152,842 B2 | 4/2012 | Schlun |
| 8,157,940 B2 | 4/2012 | Edwin et al. |
| 8,172,828 B2 | 5/2012 | Chang et al. |
| 8,182,432 B2 | 5/2012 | Kim et al. |
| 8,190,389 B2 | 5/2012 | Kim et al. |
| 8,192,420 B2 | 6/2012 | Morriss et al. |
| 8,206,349 B2 | 6/2012 | Slenker et al. |
| 8,211,169 B2 | 7/2012 | Lane et al. |
| 8,241,266 B2 | 8/2012 | Keith et al. |
| 8,249,700 B2 | 8/2012 | Clifford et al. |
| 8,273,253 B2 | 9/2012 | Curran |
| 8,277,503 B2 | 10/2012 | Lavigne |
| 8,277,504 B2 | 10/2012 | Lavigne |
| 8,282,667 B2 | 10/2012 | Drontle et al. |
| 8,313,762 B2 | 11/2012 | Oliver et al. |
| 8,317,816 B2 | 11/2012 | Becker |
| 8,328,865 B2 | 12/2012 | Bales, Jr. et al. |
| 8,328,867 B2 | 12/2012 | Dolan et al. |
| 8,333,799 B2 | 12/2012 | Bales, Jr. et al. |
| 8,333,800 B2 | 12/2012 | Bruszewski et al. |
| 8,337,454 B2 | 12/2012 | Eaton et al. |
| 8,337,650 B2 | 12/2012 | Edwin et al. |
| 8,348,969 B2 | 1/2013 | Keith et al. |
| 8,348,995 B2 | 1/2013 | Tuval et al. |
| 8,348,996 B2 | 1/2013 | Tuval et al. |
| 8,353,952 B2 | 1/2013 | Thompson et al. |
| 8,377,083 B2 | 2/2013 | Mauch et al. |
| 8,414,473 B2 | 4/2013 | Jenkins et al. |
| 8,414,643 B2 | 4/2013 | Tuval et al. |
| 8,425,457 B2 | 4/2013 | John et al. |
| 8,425,488 B2 | 4/2013 | Clifford et al. |
| 8,435,261 B2 | 5/2013 | Arcand et al. |
| 8,435,290 B2 | 5/2013 | Clifford et al. |
| 8,439,687 B1 | 5/2013 | Morriss et al. |
| 8,452,392 B2 | 5/2013 | Morriss et al. |
| 8,460,323 B2 | 6/2013 | Mauch et al. |
| 8,485,199 B2 | 7/2013 | Morriss |
| 8,500,793 B2 | 8/2013 | Zipse et al. |
| 8,500,801 B2 | 8/2013 | Eberhardt et al. |
| 8,529,548 B2 | 9/2013 | Blott et al. |

(56) References Cited

U.S. PATENT DOCUMENTS

| | | |
|---|---|---|
| 8,529,941 B2 | 9/2013 | Hakimimehr et al. |
| 8,535,707 B2 | 9/2013 | Arensdorf et al. |
| 8,540,694 B2 | 9/2013 | Flaherty et al. |
| 8,551,156 B2 | 10/2013 | Wack et al. |
| 8,562,672 B2 | 10/2013 | Bonhoeffer et al. |
| 8,563,510 B2 | 10/2013 | Hakimimehr et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,585,730 B2 * | 11/2013 | Eaton .................. A61K 9/70 606/199 |
| 8,585,731 B2 | 11/2013 | Abbate et al. |
| 8,617,337 B2 | 12/2013 | Layne et al. |
| 8,623,043 B1 | 1/2014 | Keith et al. |
| 8,647,379 B2 | 2/2014 | McDermott et al. |
| 8,647,458 B2 | 2/2014 | Banas et al. |
| 8,657,846 B2 | 2/2014 | Keith et al. |
| 8,657,867 B2 | 2/2014 | Dorn et al. |
| 8,663,192 B2 | 3/2014 | Hester et al. |
| 8,673,000 B2 | 3/2014 | Tabor et al. |
| 8,673,099 B2 | 3/2014 | Bogert |
| 8,691,288 B2 | 4/2014 | Myntti |
| 8,702,626 B1 | 4/2014 | Kim et al. |
| 8,702,702 B1 | 4/2014 | Edwards et al. |
| 8,715,169 B2 | 5/2014 | Chang et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,297 B2 | 6/2014 | Miyoshi et al. |
| 8,747,389 B2 | 6/2014 | Goldfarb et al. |
| 8,747,460 B2 | 6/2014 | Tuval et al. |
| 8,758,420 B2 | 6/2014 | Dorn et al. |
| 8,763,222 B2 | 7/2014 | Abbate et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,764,786 B2 | 7/2014 | Becker |
| 8,765,715 B2 | 7/2014 | Oliver et al. |
| 8,777,017 B2 | 7/2014 | Curran |
| 8,777,911 B2 | 7/2014 | Heagle et al. |
| 8,777,926 B2 | 7/2014 | Chang et al. |
| 8,795,713 B2 | 8/2014 | Makower et al. |
| 8,801,670 B2 | 8/2014 | Drontle et al. |
| 8,801,775 B2 | 8/2014 | Griswold |
| 8,801,776 B2 | 8/2014 | House et al. |
| 8,802,131 B2 | 8/2014 | Arensdorf et al. |
| 8,828,041 B2 | 9/2014 | Chang et al. |
| 8,834,513 B2 | 9/2014 | Hanson et al. |
| 8,834,564 B2 | 9/2014 | Tuval et al. |
| 8,840,602 B2 | 9/2014 | Morris et al. |
| 8,845,619 B2 | 9/2014 | Blott et al. |
| 8,852,143 B2 | 10/2014 | Chang et al. |
| 8,858,586 B2 | 10/2014 | Chang et al. |
| 8,858,974 B2 | 10/2014 | Eaton et al. |
| 8,864,774 B2 | 10/2014 | Liu et al. |
| 8,864,787 B2 | 10/2014 | Muni et al. |
| 8,870,893 B2 | 10/2014 | Makower et al. |
| 8,876,894 B2 | 11/2014 | Tuval et al. |
| 8,876,895 B2 | 11/2014 | Tuval et al. |
| 8,888,686 B2 | 11/2014 | Drontle et al. |
| 8,894,614 B2 | 11/2014 | Muni et al. |
| 8,905,922 B2 | 12/2014 | Makower et al. |
| 8,920,419 B2 | 12/2014 | Edwards et al. |
| 8,926,689 B2 | 1/2015 | Bogert |
| 8,932,276 B1 | 1/2015 | Morriss et al. |
| 8,945,088 B2 | 2/2015 | Chang et al. |
| 8,951,225 B2 | 2/2015 | Evard et al. |
| 8,968,269 B2 | 3/2015 | Becker |
| 8,979,888 B2 | 3/2015 | Morriss et al. |
| 8,986,341 B2 | 3/2015 | Abbate et al. |
| 8,997,998 B2 | 4/2015 | Curran et al. |
| 9,005,284 B2 | 4/2015 | Ressemann |
| 9,011,363 B2 | 4/2015 | Clopp et al. |
| 9,022,967 B2 | 5/2015 | Oliver et al. |
| 9,039,657 B2 | 5/2015 | Makower et al. |
| 9,039,680 B2 | 5/2015 | Makower et al. |
| 9,050,440 B2 | 6/2015 | Becker |
| 9,055,965 B2 | 6/2015 | Chang et al. |
| 9,072,619 B2 | 7/2015 | Lam et al. |
| 9,072,681 B2 | 7/2015 | Hakimimehr et al. |
| 9,078,783 B2 | 7/2015 | Morriss et al. |
| 9,084,691 B2 | 7/2015 | Wack et al. |
| 9,084,876 B2 | 7/2015 | Makower et al. |
| 9,089,258 B2 | 7/2015 | Goldfarb et al. |
| 9,095,364 B2 | 8/2015 | Muni et al. |
| 9,095,646 B2 | 8/2015 | Chow et al. |
| 9,101,384 B2 | 8/2015 | Makower et al. |
| 9,101,739 B2 | 8/2015 | Lesch, Jr. et al. |
| 9,114,040 B2 | 8/2015 | Dorn et al. |
| 9,138,569 B2 | 9/2015 | Edgren et al. |
| 9,144,663 B2 | 9/2015 | Ahlberg et al. |
| 9,192,692 B2 | 11/2015 | Medina et al. |
| 9,192,751 B2 | 11/2015 | Macaulay et al. |
| 9,220,879 B2 | 12/2015 | Chang et al. |
| 9,238,125 B2 | 1/2016 | Vaccaro et al. |
| 9,241,834 B2 | 1/2016 | Chang et al. |
| 9,271,925 B2 | 3/2016 | Hammerick |
| 9,295,547 B2 | 3/2016 | Costello et al. |
| 9,308,358 B2 | 4/2016 | Oliver et al. |
| 9,308,361 B2 | 4/2016 | Muni et al. |
| 9,320,876 B2 | 4/2016 | Ressemann et al. |
| 9,333,220 B2 | 5/2016 | Tijsma et al. |
| 9,333,365 B2 | 5/2016 | Zhao |
| 9,351,750 B2 | 5/2016 | Muni et al. |
| 9,398,966 B2 | 7/2016 | Thompson |
| 9,402,719 B2 | 8/2016 | Lane |
| 9,427,343 B2 | 8/2016 | Bogert |
| 9,456,897 B2 | 10/2016 | Krivoruchko et al. |
| 9,498,239 B2 | 11/2016 | Schreck et al. |
| 9,504,556 B2 | 11/2016 | Bebb |
| 9,504,812 B2 | 11/2016 | Edgren et al. |
| 9,561,119 B2 | 2/2017 | Eberhardt et al. |
| 9,597,485 B2 | 3/2017 | Edgren et al. |
| 9,622,850 B2 | 4/2017 | Bebb et al. |
| 9,629,644 B2 | 4/2017 | Schreck et al. |
| 9,649,477 B2 | 5/2017 | Muni et al. |
| 9,662,168 B2 | 5/2017 | Edwards et al. |
| 9,675,451 B2 | 6/2017 | Garde et al. |
| 9,681,914 B2 | 6/2017 | Edwards et al. |
| 9,700,326 B2 | 7/2017 | Morriss et al. |
| 9,707,110 B2 | 7/2017 | McDermott et al. |
| 9,717,612 B2 | 8/2017 | Dorn et al. |
| 2003/0108588 A1 * | 6/2003 | Chen .................. A61K 9/0024 424/423 |
| 2004/0078077 A1 | 4/2004 | Binette |
| 2005/0107870 A1 * | 5/2005 | Wang .................. A61L 31/10 623/1.44 |
| 2005/0245906 A1 * | 11/2005 | Makower .............. A61B 5/06 604/891.1 |
| 2006/0106361 A1 | 5/2006 | Muni |
| 2006/0229711 A1 | 10/2006 | Yan |
| 2007/0014830 A1 | 1/2007 | Tijsma |
| 2007/0208252 A1 | 9/2007 | Makower |
| 2008/0243140 A1 | 10/2008 | Gopferich et al. |
| 2009/0030499 A1 | 1/2009 | Bebb et al. |
| 2009/0182404 A1 | 7/2009 | Shokoohi |
| 2009/0258053 A1 | 10/2009 | Horvers |
| 2009/0270965 A1 | 10/2009 | Sinha et al. |
| 2010/0016946 A1 | 1/2010 | McDermott |
| 2010/0131049 A1 | 5/2010 | Perkins et al. |
| 2010/0331619 A1 | 12/2010 | Miyoshi et al. |
| 2011/0009951 A1 | 1/2011 | Bogert |
| 2011/0015612 A1 | 1/2011 | Arcand et al. |
| 2011/0054552 A1 | 3/2011 | Takayama et al. |
| 2011/0060214 A1 | 3/2011 | Makower |
| 2011/0118802 A1 | 5/2011 | Usui |
| 2011/0155149 A1 | 6/2011 | Mauch |
| 2011/0270379 A1 | 11/2011 | Bruszewski |
| 2012/0035677 A1 | 2/2012 | Imabayashi et al. |
| 2012/0059454 A1 | 3/2012 | Millwee |
| 2012/0071824 A1 | 3/2012 | Chang et al. |
| 2013/0006055 A1 | 1/2013 | Goldfarb et al. |
| 2013/0035739 A1 | 2/2013 | Goto |
| 2013/0165873 A1 | 6/2013 | Morriss et al. |

(56) References Cited

U.S. PATENT DOCUMENTS

| | | |
|---|---|---|
| 2013/0231529 A1 | 9/2013 | Chang et al. |
| 2013/0253564 A1 | 9/2013 | Edgren et al. |
| 2013/0261388 A1 | 10/2013 | Jenkins et al. |
| 2013/0282113 A1 | 10/2013 | Punga et al. |
| 2013/0304196 A1 | 11/2013 | Kelly |
| 2013/0310780 A1 | 11/2013 | Phillips |
| 2013/0310781 A1 | 11/2013 | Phillips et al. |
| 2013/0324970 A1 | 12/2013 | Arcand et al. |
| 2014/0012075 A1 | 1/2014 | Konstorum |
| 2014/0031852 A1 | 1/2014 | Edgren et al. |
| 2014/0031917 A1 | 1/2014 | Thompson |
| 2014/0074140 A1 | 3/2014 | Johnson et al. |
| 2014/0074141 A1 | 3/2014 | Johnson et al. |
| 2014/0079755 A1 | 3/2014 | Eaton et al. |
| 2014/0100644 A1 | 4/2014 | Palasis |
| 2014/0107763 A1 | 4/2014 | Layne et al. |
| 2014/0107766 A1 | 4/2014 | Banas et al. |
| 2014/0154236 A1 | 6/2014 | Hester et al. |
| 2014/0200444 A1 | 7/2014 | Kim et al. |
| 2014/0222144 A1 | 8/2014 | Eberhardt et al. |
| 2014/0276408 A1 | 9/2014 | Abbate |
| 2014/0276654 A1 | 9/2014 | Jenkins |
| 2014/0296898 A1 | 10/2014 | Chang et al. |
| 2014/0330372 A1 | 11/2014 | Weston et al. |
| 2014/0336693 A1 | 11/2014 | Goldfarb et al. |
| 2014/0336694 A1 | 11/2014 | Becker |
| 2015/0119974 A1 | 4/2015 | Rothstein |
| 2015/0196735 A1 | 7/2015 | Olig et al. |

\* cited by examiner

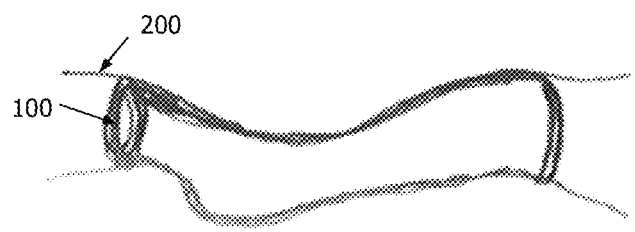
FIG. 13
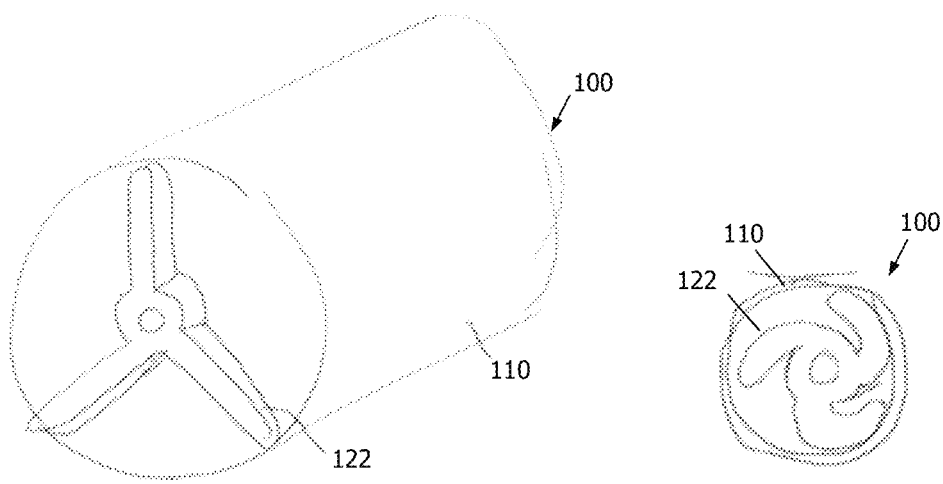
FIG. 14A
FIG. 14B
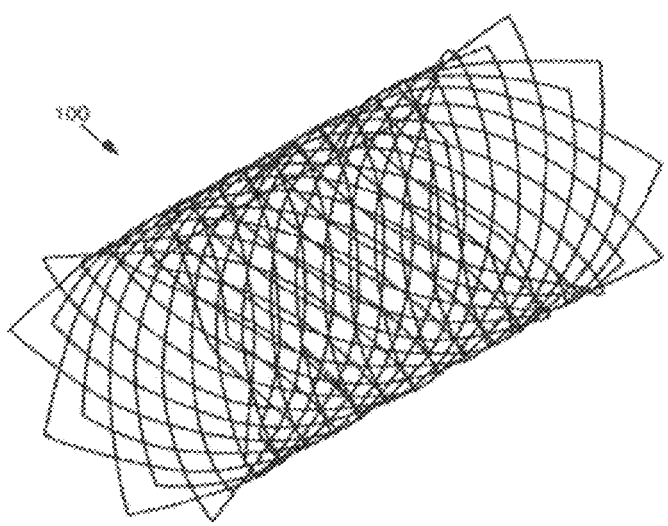
FIG. 15

FIG. 29A  FIG. 29B

IMPLANTABLE SCAFFOLDS FOR TREATMENT OF SINUSITIS

CROSS-REFERENCE TO RELATED APPLICATIONS

This application is a continuation in part of U.S. Ser. No. 15/197,686 entitled IMPLANTABLE SCAFFOLDS FOR TREATMENT OF SINUSITIS and filed Jun. 29, 2016, which claims the benefit of U.S. Provisional Application No. 62/186,030 entitled IMPLANTABLE SCAFFOLDS FOR TREATMENT OF SINUSITIS and filed Jun. 29, 2015, U.S. Provisional Application No. 62/289,982 entitled IMPLANTABLE SCAFFOLDS FOR TREATMENT OF SINUSITIS and filed Feb. 2, 2016, and U.S. Provisional Application No. 62/332,134 entitled IMPLANTABLE SCAFFOLDS FOR TREATMENT OF SINUSITIS and filed May 5, 2016, each of which is hereby incorporated by reference in its entirety.

FIELD OF THE DISCLOSURE

This disclosure describes, inter alia, materials, devices, kits and methods that may be used to treat chronic rhinosinusitis.

BACKGROUND

Chronic rhinosinusitis (CRS) is a common condition defined by symptomatic inflammation of the paranasal sinuses lasting longer than 12 weeks. Up to 16% of the population is affected by this condition. Cavities associated with CRS include the maxillary, frontal, ethmoid, ostiomeatal complex, ethmoid infundibulum and sphenoid sinuses as well as the middle meatus location, or a combination thereof. Common symptoms of CRS include impaired nasal obstruction, facial pressure or fullness, nasal discharge, and olfactory loss; these symptoms likely arise due to mucosal inflammation, local infection, and/or impairment of mucociliary function.

While there is no approved therapy for the treatment of CRS, evidence-based medical management supports the use of a host of oral or topical corticosteroid therapies for the disease. High-volume, daily saline irrigation with adjunct application of a topical corticosteroid via nasal sprays is common as a first-line therapy. Second line agents for flare-ups and worsening disease include a short course of oral corticosteroids, although this approach can lead to unintended systemic side effects including glaucoma, osteoporosis and avascular necrosis of the hip and shoulder. It is estimated that up to 12-50% of CRS patients do not respond positively to this recommended medical regimen and are often candidates for Functional Endoscopic Sinus Surgery (FESS) and/or balloon sinuplasty dilation.

Avoidance of surgical interventions in the treatment of CRS would be ideal for patients since these procedures carry surgery-associated risks, cause post-operative pain and discomfort, and require burdensome and costly post-operative cleaning. Clinical data has demonstrated that topical corticosteroids are effective in reducing inflammation associated with CRS and thus, are a rational choice for the management of this condition.

An ideal treatment for CRS would provide local and sustained anti-inflammatory drug delivery in the sinuses of patients as an alternative treatment option to sinus surgery. Such a therapy would ideally establish safe and effective sustained drug delivery localized to the inflamed tissue and in some cases could prevent the need for surgery.

FESS involves removal of bone and tissue to enlarge sinus outflow tracts, widen sinus openings or ostia and allow for ventilation of previously obstructed sinus cavities and restoration of mucociliary clearance. Currently, there are approximately 500,000 procedures performed annually in the United States.

By removing small pieces of bone, polyps, and/or debridement of tissue within the sinus cavities, FESS has proven to be an effective way to improve the drainage pathway of the sinuses. However, a significant number of postoperative complications such as inflammation, swelling, disease recurrence, need for repeat procedures and synechiae are often observed. Postoperative care is therefore an important component of FESS. Approximately 10-20% of FESS patients become refractory, do not respond to treatment, and may require additional surgical intervention or lifelong medical therapy.

Some form of sinus packing is generally conducted postoperatively to FESS. Examples of packing materials include simple dressings moistened with saline, foam dressings based on polysaccharide gel, PEG-based materials, and middle meatal spacers. Implantable sinus stents have also been devised and these scaffolds are intended to stabilize the sinus openings and the turbinates, reduce edema, and/or prevent obstruction by tissue adhesion. They also have the capability of being integrated with therapeutic agent(s) that may be delivered topically over time. This local delivery of therapeutic agent(s) may be superior to topical application in the postoperative setting. In this regard, the USFDA-approved PROPEL™ system (Intersect ENT, Menlo Park, Calif., USA) is a self-expanding, bioresorbable, steroid-eluting stent that is intended for use in the ethmoid sinus post-FESS.

SUMMARY

As used herein, terms "sinus" and "sinus cavity" refer to both sinus cavities and nasal cavities, which include, for example, the maxillary, frontal and ethmoid sinuses, the ostiomeatal complex, the ethmoid infundibulum and the sphenoid sinuses as well as the middle meatus (a sinus cavity).

The present disclosure describes various sinus scaffolds having fiber-based and non-fiber-based designs. These designs vary in form, dimension, and delivery location (i.e. maxillary, frontal, ethmoidal, sphenoidal sinuses, and middle meatus). In addition, therapeutic agent(s) may optionally be included within the scaffolds for local delivery over a brief or extended period of time. Therefore, these scaffolds may be used to improve sinus patency, for example, in surgically modified sinus spaces or in sinus spaces that have not previously undergone surgical modification. Moreover, these scaffolds may be used to deliver local therapeutic agent(s) to such sinus spaces, including, for instance, as part of a treatment program that is an alternative to sinus surgery (e.g., FESS) or in other instances as part of a postoperative care of FESS in some embodiments.

In various aspects, the present disclosure pertains to generally tubular scaffolds that are configured for implantation in a sinus cavity of a patient. As used herein, "generally tubular" includes hollow shapes of circular cross-section or non-circular cross-section (e.g., oval, etc.) and hollow shapes of constant diameter or variable diameter (e.g. of tapered diameter, such as in a hollow frustum). Both ends of the generally tubular scaffold may be open, one end may be open and the other end closed, or both ends may be closed. In many beneficial embodiments described herein a generally tubular scaffold is employed, which is in the shape of a hollow cylinder (i.e., having a circular cross-section and a constant diameter), in which both ends are open. The scaffolds may have a fiber-based or non-fiber-based structure and comprise a scaffold material and an optional conformal coating, which comprises a coating material that at least partially coats the scaffold material.

The scaffold material may or may not comprise a therapeutic agent, for example, selected from the therapeutic agents described elsewhere herein, among other possibilities.

Where the scaffold comprises a therapeutic agent, the scaffold may be provided with a variety of release profiles.

In some embodiments, the scaffold may demonstrate certain cumulative release characteristic when subjected to an in vitro assay wherein the scaffold is submerged in a pH 7.4 PBS buffer solution containing 2% wt % SDS at 37° C. under gentle shaking on a rotary shaker, wherein a volume of the buffer solution in which the scaffold is submerged is at least 10 times greater than a volume of the buffer solution at which a quantity of therapeutic agent corresponding to the total amount of therapeutic agent in the scaffold is at a saturation point in the buffer solution (sometimes referred to as sink conditions), and wherein buffer is removed completely weekly for quantification and replaced with fresh buffer.

After one week in such in vitro conditions, the scaffold may demonstrate a cumulative release of therapeutic agent based on total amount of therapeutic agent in the scaffold ranging from 1% or less to 70% or more (e.g., ranging from 1% to 2% to 5% to 10% to 15% to 20% to 25% to 30% to 35% to 40% to 45% to 50% to 55% to 60% to 65% to 70%) (i.e., ranging between any two of the preceding numerical values), beneficially ranging from 2% to 50%, more beneficially ranging from 5% to 30%, in certain embodiments.

Alternatively or in addition, after two weeks in such in vitro conditions, the scaffold may demonstrate a cumulative release of therapeutic agent based on total amount of therapeutic agent in the scaffold ranging from 5% or less to 80% or more (e.g., ranging from 5% to 7% to 10% to 15% to 20% to 25% to 30% to 35% to 40% to 45% to 50% to 55% to 60% to 65% to 70% to 75% to 80%) (i.e., ranging between any two of the preceding numerical values), beneficially ranging from 7% to 50%, more beneficially ranging from 10% to 30%, in certain embodiments.

Alternatively or in addition, after four weeks in such in vitro conditions, the scaffold may demonstrate a cumulative release of therapeutic agent based on total amount of therapeutic agent in the scaffold ranging from 10% or less to 90% or more (e.g., ranging from 10% to 15% to 20% to 25% to 30% to 35% to 40% to 45% to 50% to 55% to 60% to 65% to 70% to 75% to 80% to 85% to 90%) (i.e., ranging between any two of the preceding numerical values), beneficially ranging from 20% to 75%, more beneficially ranging from 30% to 60%, in certain embodiments.

Alternatively or in addition, after eight weeks in such in vitro conditions, the scaffold may demonstrate a cumulative release of therapeutic agent based on total amount of therapeutic agent in the scaffold ranging from 25% or less to 100% (e.g., ranging from 20% to 25% to 30% to 35% to 40% to 45% to 50% to 55% to 60% to 65% to 70% to 75% to 80% to 85% to 90% to 95% to 100%) (i.e., ranging between any two of the preceding numerical values), beneficially ranging from 30% to 90%, more beneficially ranging from 40% to 80%, in certain embodiments.

In some embodiments, the scaffold may demonstrate certain cumulative in vivo release characteristic.

For example, after one week in vivo in a human sinus or a rabbit sinus, the scaffold may demonstrate a cumulative release of therapeutic agent based on total amount of therapeutic agent in the scaffold ranging from 1% or less to 45% or more (e.g., ranging from 1% to 1.5% to 2% to 3% to 5% to 10% to 15% to 20% to 25% to 30% to 35% to 40% to 45%) (i.e., ranging between any two of the preceding numerical values), beneficially 1.5 ranging to 35%, more beneficially ranging from 3% to 20%, in certain embodiments.

Alternatively or in addition, after two weeks in vivo in a human sinus or a rabbit sinus, the scaffold may demonstrate a cumulative release of therapeutic agent based on total amount of therapeutic agent in the scaffold ranging from 3% or less to 50% or more (e.g., ranging from 3% to 5% to 7% to 10% to 15% to 20% to 25% to 30% to 35% to 40% to 45% to 50%) (i.e., ranging between any two of the preceding numerical values), beneficially ranging from 5% to 35%, more beneficially ranging from 7% to 20%, in certain embodiments.

Alternatively or in addition, after four weeks in vivo in a human sinus or a rabbit sinus, the scaffold may demonstrate a cumulative release of therapeutic agent based on total amount of therapeutic agent in the scaffold ranging from 7% or less to 60% or more (e.g., ranging from 7% to 10% to 15% to 20% to 25% to 30% to 35% to 40% to 45% to 50% to 55% to 60%) (i.e., ranging between any two of the preceding numerical values), beneficially ranging from 15% to 50%, more beneficially ranging from 20% to 30%, in certain embodiments.

Alternatively or in addition, after eight weeks in vivo in a human sinus or a rabbit sinus, the scaffold may demonstrate a cumulative release of therapeutic agent based on total amount of therapeutic agent in the scaffold ranging from 15% or less to 100% (e.g., ranging from 15% to 20% to 25% to 30% to 35% to 40% to 45% to 50% to 55% to 60% to 65% to 70% to 75% to 80% to 85% to 90% to 95% to 100%) (i.e., ranging between any two of the preceding numerical values), beneficially ranging from 20% to 60%, more beneficially ranging from 25% to 55%, in certain embodiments.

In embodiments where the scaffolds comprise a fiber-based structure, the scaffold may comprise a braided structure containing one or more strands of the scaffold material.

In some embodiments, which may be used in conjunction with any of the above aspects and embodiments, the braided structure may comprise opposing sets of helical strands. For example, each set of helical strands may comprise between 2 and 64 members, more typically between 8 and 32 members.

In some embodiments, which may be used in conjunction with any of the above aspects and embodiments, the braided structure may comprise a first strand of material having a first stiffness and a second strand of material having a second stiffness that is greater than the first stiffness. As a specific example, the second strand of material may have a modulus of >3GPa which may be at least 2 times the modulus of the first strand of material.

In some embodiments, which may be used in conjunction with any of the above aspects and embodiments, the braided structure may comprise cells of differing size. For example, a portion of the braided structure may be removed such that cells of differing sizes are formed or the braided structure may be braided such that cells of differing sizes are formed, among other possibilities. In some instances, the cells of differing size may include first cells having a first area and second cells having a second area, wherein first area is at least 50% greater than the second area. Variation in cell size may occur, for example, along a longitudinal length of the scaffold and/or around a circumference of the scaffold.

In some embodiments, which may be used in conjunction with any of the above aspects and embodiments, the scaffold may comprise a longitudinal elastomeric fiber that is mechanically coupled to two or more nodes of the braided structure.

In some embodiments, which may be used in conjunction with any of the above aspects and embodiments, one or more ends of the one or more strands may be woven back into the braided structure and bonded.

In some embodiments, the generally tubular scaffolds of the present disclosure may comprise a scaffold material that includes an elongate member that is wound into a spiral tubular structure. In certain of these embodiments, the elongate member is in the form of a ribbon-shaped elongate member that is wound into a spiral tubular structure. The ribbon-shaped elongate member may, for example, be in the form of a solid film or may comprise apertures (e.g., formed by forming holes in a solid film, formed by crossing fibers within a braided structure, etc.).

In some embodiments, the generally tubular scaffolds of the present disclosure comprise a scaffold material that includes a plurality of parallel open hoops. In certain of these embodiments, the open hoops are ribbon-shaped open hoops. The ribbon-shaped open hoops may, for example, be in the form of a solid film or may comprise apertures.

In some embodiments, the generally tubular scaffolds of the present disclosure comprise a scaffold material that includes a knitted structure. In certain of these embodiments, the knitted structure may comprise a single strand that can be pulled to unravel and remove the scaffold.

In some embodiments, the generally tubular scaffolds of the present disclosure may comprise a plurality of radially expandable inserts within a generally tubular structure. In certain of these embodiments, each radially expandable insert may comprise a hub and a plurality of radially expandable arms or may comprise a braided hoop, among other possibilities.

In some embodiments, which may be used in conjunction with any of the above aspects and embodiments, a distal end of the generally tubular scaffolds may be configured to be captured by an additional device, and the generally tubular scaffolds may be configured to be inverted and removed by pulling the distal end into a lumen formed by the generally tubular scaffold.

In some embodiments, which may be used in conjunction with any of the above aspects and embodiments, the generally tubular scaffolds may comprise a conformal coating, for example, formed from an elastomeric or non-elastomeric coating material. For instance, the coating material may be an elastomeric material that comprises poly(L-lactide-co-ε-caprolactone) (also referred to herein as poly(lactide-co-caprolactone) and as poly(lactic acid-co-caprolactone)) with urethane crosslinks, urea crosslinks, or both urethane and urea crosslinks; the coating material may be an elastomeric material that comprises diisocyanate-cured (e.g., hexamethylene diisocyanate-cured, etc.), hydroxyl-terminated branched poly(L-lactide-co-ε-caprolactone). The coating material may or may not comprise a therapeutic agent, for example, selected from the therapeutic agents described elsewhere herein, among other possibilities. The coating material may cover alternating areas along a length of the generally tubular scaffolds, and/or the coating material may cover ends of the generally tubular scaffolds while not covering an area between the ends of generally tubular scaffolds, among many other possibilities. In the case of braided structures, the coating material may cover some nodes of the braided structure while leaving other nodes uncovered. A thickness of the coating material at nodes of the braided structure may range, for example, from 1 to 100 times a thickness of the coating material between nodes of the braided structure (e.g., ranging anywhere from 1 to 2 to 5 to 10 to 25 to 50 to 75 to 100 times a thickness of the coating material between nodes of the braided structure).

In certain embodiments, which may be used in conjunction with any of the above aspects and embodiments, the scaffold may have a conformal coating, which may be further coated with an additional conformal coating that comprises an additional coating material and a therapeutic agent, for example, selected from the therapeutic agents described elsewhere herein, among other possibilities. The additional conformal coating may range, for example, from between 1 μm to 25 μm in thickness (e.g., ranging from 1 to 2 to 5 to 20 to 25 μm in thickness), among other possibilities. In certain embodiments, the additional coating material may be a biodegradable polymer such as poly(lactide-co-ε-caprolactone) or a mixture of poly(lactide-co-ε-caprolactone) and an additional polymer such as a homopolymer or copolymer of lactide, for instance, poly(lactide-co-glycolide) (also referred to herein as poly(lactic acid-co-glycolic acid)). Where included, the additional polymer may be present, as a weight percent of the additional conformal coating, in amounts ranging, for example, from 5 to 50%. The poly(lactide-co-ε-caprolactone) may have, for example, a molar percentage of lactide ranging from 50 to 95% and a molar percentage of caprolactone ranging from 50 to 5%, among other possibilities. Where present, the poly(lactide-co-glycolide) may have, for example, a molar percentage of lactide ranging from 50 to 99.9% and a molar percentage of glycolide ranging from 50 to 0.1%, among other possibilities. In certain specific embodiments, the additional conformal coating may comprise from 50 to 99.9 wt % (e.g., from 50 to 60 to 70 to 80 to 90 to 95 to 99 to 99.5 to 99.9 wt %) of one or more biodegradable polymers and from 0.1 to 50 wt % (e.g., from 0.1 to 0.5 to 1 to 5 to 10 to 20 to 30 to 40 to 50 wt %) mometasone furoate, among many other possibilities. Typical amounts of mometasone furoate may range, for example, from 0.1 μg/mm$^2$ or less to 20 μg/mm$^2$ or more (i.e., ranging from 0.1 or less to 20 μg or more of mometasone furoate per square mm of scaffold surface area, where scaffold surface area, A, is calculated as A=πDL, where D is the manufactured diameter of the scaffold and L is the manufactured length of the scaffold), for example, ranging from 0.1 μg/mm$^2$ to 0.2 μg/mm$^2$ to 0.5 μg/mm$^2$ to 1 μg/mm$^2$ to 2 μg/mm$^2$ to 5 μg/mm$^2$ to 10 μg/mm$^2$ to 15 μg/mm$^2$ to 20 μg/mm$^2$ (i.e., ranging between any two of the preceding numerical values), more typically ranging from 1 μg/mm$^2$ to 10 μg/mm$^2$, among other possible values.

In certain embodiments, which may be used in conjunction with any of the above aspects and embodiments, the scaffold may be further coated with a conformal topcoat layer, which is disposed over the additional conformal coating that comprises an additional coating material and a therapeutic agent. The topcoat layer may be formed, for example, from a single biodegradable polymer or a blend of biodegradable polymers selected from those described elsewhere herein. In certain embodiments, the topcoat layer may be formed from the same polymer or polymers found in the underlying additional conformal coating, but will not contain a therapeutic agent. The topcoat layer may be employed, for example, to delay and/or slow release of the therapeutic agent in the underlying additional conformal coating. The topcoat layer may range, for example, from between 1 μm and 30 μm in thickness, among other possibilities.

In other aspects, the present disclosure pertains to methods of treatment that comprises (a) introducing a scaffold, for example, a scaffold in accordance with any of the above aspects and embodiments, into a sinus cavity of a patient while in a radially constrained shape and (b) removing a constraint that maintains the scaffold in the constrained shape, such that the scaffold self-expands within the sinus cavity. Examples of sinus cavities suitable for device implantation include the ethmoid sinus, the middle meatus space, the frontal sinus ostia (also referred to as the frontal recess), the maxillary sinus ostia and the sphenoid sinus ostia, among others.

In still other aspects, the present disclosure pertains to kits that comprise (a) a scaffold, for example, a scaffold in accordance with any of the above aspects and embodiments, (b) a delivery catheter and (c) an optional loading aid. In certain embodiments, a scaffold in accordance with any of the above aspects and embodiments may be loaded into a 15 French delivery catheter or smaller, into a 9 French delivery catheter or smaller, into a 6 French delivery catheter or smaller, or even into a 4 French delivery catheter or smaller. In certain embodiments, a scaffold in accordance with any of the above aspects and embodiments may be loaded into 6.5 french to 9 french catheter.

In some embodiments, the delivery catheter may be configured to maintain the scaffold in a radially constrained shape and to remove a constraint that maintains the scaffold in said radially constrained shape at a delivery location.

In some embodiments, which may be used in conjunction with any of the above aspects and embodiments, the delivery catheter may comprise an expandable device. For example, the delivery catheter may be a balloon catheter that comprises a catheter shaft having an inflation lumen and one or more inflatable balloons disposed at or near a distal end of a catheter shaft, which one or more inflatable balloons may or may not be at least partially coated with a therapeutic-agent-containing coating.

In still other aspects, the present disclosure pertains to delivery systems that comprise (a) a scaffold, for example, as scaffold in accordance with any of the above aspects and embodiments and (b) a delivery catheter, wherein the scaffold is positioned in a radially constrained shape within the delivery catheter. Such delivery systems may be used, for example, in a method of treatment that comprises (a) introducing the scaffold into the sinus cavity of a patient while in the radially constrained shape, such that the scaffold is positioned at a delivery location in the sinus cavity and (b) removing a constraint that maintains the scaffold in the radially constrained shape, such that the scaffold self-expands within the sinus cavity.

In still other aspects, the present disclosure pertains to delivery systems that comprise (a) a scaffold, for example, as scaffold in accordance with any of the above aspects and embodiments and (b) a delivery catheter comprising an expandable device, wherein the scaffold is be positioned on, in, under, proximal to, or distal to the expandable device. For example, the expandable device may be an expandable frame or an inflatable balloon. For instance, the delivery catheter may be a balloon catheter that comprises a catheter shaft having an inflation lumen and one or more inflatable balloons disposed at or near a distal end of a catheter shaft, which one or more inflatable balloons may or may not be at least partially coated with a therapeutic-agent-containing coating. Such delivery systems may be used, for example, in a method of treatment that comprises (a) introducing the scaffold into the sinus cavity of a patient such that the scaffold is positioned at a delivery location in the sinus cavity and (b) expanding the expandable device while the expandable device is positioned in the lumen of the scaffold.

In yet other aspects, the present disclosure pertains to methods of forming a coated scaffold comprising: (a) applying a first coating solution comprising a first solvent, a branched biodegradable polymer and a diisocyanate cross-linking agent to a scaffold in accordance with any of the above aspects and embodiments and (b) curing the applied first coating solution at room temperature or at elevated temperature.

In certain embodiments, which may be used in conjunction with any of the above aspects and embodiments, the branched biodegradable polymer may be, for example, a branched poly(lactide-co-ε-caprolactone), for instance, a branched hydroxyl terminated poly(lactide-co-ε-caprolactone).

In certain embodiments, which may be used in conjunction with any of the above aspects and embodiments, the solution may further comprise a chain terminator. For example, the chain terminator may be an alcohol, for example a C8-C18 alcohol, such as 1-dodecanol and stearyl alcohol, among many other possibilities.

In certain embodiments, which may be used in conjunction with any of the above aspects and embodiments, the diisocyanate cross-linking agent may be hexamethylene diisocyanate, among many other possibilities.

In certain embodiments, which may be used in conjunction with any of the above aspects and embodiments, the first solvent may comprise dichloromethane or ethyl acetate among many other possibilities. In certain of these embodiments, the first solvent may further comprise anisole as a co-solvent.

In certain embodiments, which may be used in conjunction with any of the above aspects and embodiments, the scaffold may be a braided structure comprising one or more strands of the scaffold material and a plurality of nodes and the coating solution may be applied to at least the nodes of the scaffold.

In certain embodiments, which may be used in conjunction with any of the above aspects and embodiments, the method may further comprise applying a second coating solution comprising an additional biodegradable polymer (e.g., poly(lactide-co-ε-caprolactone), among many other possibilities), a second solvent (e.g., comprising ethyl formate and anisole, among many other possibilities), and a therapeutic agent to the scaffold after applying the first coating solution. The therapeutic agent may be a steroidal anti-inflammatory drug such as mometasone furoate, among many other possibilities.

Other aspects of the present disclosure pertain to coated scaffolds formed by methods in accordance with any of the above aspects and embodiments.

Potential benefits of the present disclosure include one or more of the following, in association with adult and pediatric procedures, among others: (a) stabilization of sinus openings/ostia, (b) reduction of synechiae and post-operative adhesions, (c) local and extended therapeutic agent delivery for therapy as an alternative to surgery (for example, the treatment of patients that have failed medical management based on the administration of oral and/or topical steroids), preoperative and/or postoperative care, and (d) therapeutic agent delivery to refractory patients not responsive to FESS, (e) prevention of stenosis of ostia/opening of sinuses following surgical dilation.

These and other aspects, embodiments and benefits of the present disclosure will become immediately apparent to those of ordinary skill in the art upon review of the detailed description and claims to follow.

Additional enumerated aspects of the present disclosure are set forth in the following paragraphs:

Aspect 1. A scaffold configured for implantation in a sinus cavity, said scaffold comprising a generally tubular structure having a lumen and comprising a scaffold material and an optional conformal coating comprising a coating material that at least partially coats the scaffold material.

Aspect 2. The scaffold of aspect 1, wherein the scaffold comprises a fiber-based structure.

Aspect 3. The scaffold of aspect 1, wherein the scaffold comprises a braided structure comprising one or more strands of the scaffold material.

Aspect 4. The scaffold of aspect 3, wherein the braided structure comprises opposing sets of helical strands.

Aspect 5. The scaffold of aspect 4, wherein each set of helical strands comprises between 2 and 64 members.

Aspect 6. The scaffold of aspect 3, wherein the braided structure comprises a first strand of material having a first stiffness and a second strand of material having a second stiffness that is greater than the first stiffness.

Aspect 7. The scaffold of aspect 6, wherein the second strand of material has a modulus of >5GPa and which is at least 2 times that of the first strand of material.

Aspect 8. The scaffold of any of aspects 3-7, wherein the braided structure comprises cells of differing size.

Aspect 9. The scaffold of aspect 8, wherein a portion of the braided structure is removed such that cells of differing sizes are formed or wherein the braided structure is braided such that cells of differing sizes are formed.

Aspect 10. The scaffold of aspect 8, comprising first cells having a first area and second cells having a second area, wherein first area is at least 50% greater than the second area.

Aspect 11. The scaffold of aspect 8, wherein a variation in cell size occurs along a longitudinal length of the scaffold.

Aspect 12. The scaffold of aspect 8, wherein a variation in cell size occurs around a circumference of the scaffold.

Aspect 13. The scaffold of any of aspects 3-12, further comprising a longitudinal elastomeric fiber that is mechanically coupled to two or more nodes of the braided structure.

Aspect 14. The scaffold of any of aspects 3-13, where one or more ends of said one or more strands is woven back into the braided structure and bonded.

Aspect 15. The scaffold of any of aspects 3-14, wherein the scaffold comprises said conformal coating comprising a coating material.

Aspect 16. The scaffold of aspect 15, wherein the coating material comprises an elastomer.

Aspect 17. The scaffold of aspect 16, wherein the elastomer comprises urethane crosslinks.

Aspect 18. The scaffold of any of aspects 15-17, wherein the coating material covers some nodes of the braided structure while leaving other nodes uncovered.

Aspect 19. The scaffold of any of aspects 15-18, wherein the coating material covers alternating areas along a length of the braided structure.

Aspect 20. The scaffold of any of aspects 15-18, wherein the coating material covers ends of the braided structure but not does not cover an area between the ends of the braided structure.

Aspect 21. The scaffold of any of aspects 15-20, wherein a thickness of the coating material at nodes of the braided structure range from 1 to 100 times a thickness of the coating material between nodes of the braided structure.

Aspect 22. The scaffold of any of aspects 15-21, wherein the one or more strands of the scaffold material comprise poly(lactide-co-glycolide) and wherein the coating material is an elastomeric material that comprises poly(L-lactide-co-caprolactone) with urethane crosslinks, urea crosslinks, or both urethane and urea crosslinks.

Aspect 23. The scaffold of any of aspects 15-21, wherein the one or more strands of the scaffold material comprise poly(lactide-co-glycolide) and wherein the coating material is an elastomeric material that comprises diisocyanate-cured, hydroxyl-terminated branched poly(L-lactide-co-caprolactone).

Aspect 24. The scaffold of aspect 23, wherein the hydroxyl-terminated branched poly(L-lactide-co-caprolactone) is cured with hexamethylene diisocyanate.

Aspect 25. The scaffold of any of aspects 15-21, 23 and 24, wherein the scaffold is further coated with an additional coating material that comprises from 50 to 99.9 wt % poly(L-lactide-co-caprolactone) and from 0.1 to 50 wt % mometasone furoate.

Aspect 26. The scaffold of aspect 22, wherein the scaffold is further coated with an additional coating material that comprises from 50 to 99.9 wt % poly(L-lactide-co-caprolactone) and from 0.1 to 50 wt % mometasone furoate.

Aspect 27. The scaffold of aspect 3, wherein the braided structure is in the form of a ribbon-shaped elongate member that is wound into a spiral tubular structure.

Aspect 28. The scaffold of aspect 1, wherein the scaffold comprises an elongate member that is wound into a spiral tubular structure.

Aspect 29. The scaffold of aspect 1, wherein the scaffold comprises a plurality of parallel open hoops.

Aspect 30. The scaffold of aspect 29, wherein the open hoops are ribbon-shaped open hoops.

Aspect 31. The scaffold of aspect 30, wherein the ribbon-shaped open hoops have a plurality of apertures.

Aspect 32. The scaffold of aspect 31, wherein the plurality of apertures creates a braid-like structure.

Aspect 33. The scaffold of aspect 1, wherein the generally tubular structure is a knitted structure.

Aspect 34. The scaffold of aspect 33, wherein the knitted structure comprises a single strand that can be pulled to unravel and remove the scaffold.

Aspect 35. The scaffold of aspect 1, comprising a plurality of radially expandable inserts within the generally tubular structure.

Aspect 36. The scaffold of aspect 35, wherein the radially expandable inserts comprise a hub and a plurality of radially expandable arms or wherein the radially expandable inserts comprise a braided hoop.

Aspect 37. The scaffold of aspect 1, wherein a distal end of the scaffold is configured to be captured by an additional device and wherein the scaffold is configured to be inverted and removed from the sinus cavity by pulling the distal end into the lumen.

Aspect 38. A method of treatment comprising (a) introducing a scaffold in accordance with any of aspects 1-37 into a sinus cavity of a patient while in a radially constrained shape and (b) removing a constraint that maintains the scaffold in said constrained shape, such that the scaffold self-expands within the sinus cavity.

Aspect 39. The method of aspect 38, wherein the sinus cavity is the ethmoid sinus, the middle meatus space, the frontal sinus ostia, the maxillary sinus ostia, the sphenoid sinus ostia, or the frontal sinus recess.

Aspect 40. A kit comprising (a) a scaffold in accordance with any of aspects 1-37, (b) a delivery catheter, and (c) an optional loading aid.

Aspect 41. The kit of aspect 40, wherein the delivery catheter is configured to maintain the scaffold in a radially constrained shape and to remove a constraint that maintains the scaffold in said radially constrained shape at a delivery location.

Aspect 42. The kit of aspect 40, wherein the delivery catheter comprises an expandable device.

Aspect 43. The kit of aspect 40, wherein the delivery catheter is a balloon catheter that comprises a catheter shaft having an inflation lumen and one or more inflatable balloons disposed at or near a distal end of a catheter shaft.

Aspect 44. The kit of aspect 43, wherein at least one of the one or more inflatable balloons is at least partially coated with a therapeutic-agent-containing coating.

Aspect 45. A delivery system comprising (a) a scaffold in accordance with any of aspects 1-37 and (b) a delivery catheter, wherein the scaffold is positioned in a radially constrained shape within the delivery catheter.

Aspect 46. A method of treatment using the delivery system of aspect 45, comprising: (a) introducing the scaffold into the sinus cavity of a patient while in the radially constrained shape, such that the scaffold is positioned at a delivery location in the sinus cavity and (b) removing a constraint that maintains the scaffold in the radially constrained shape, such that the scaffold self-expands within the sinus cavity.

Aspect 47. A delivery system comprising (a) a scaffold in accordance with any of aspects 1-37 and (b) a delivery catheter comprising an expandable device, wherein the scaffold is positioned on, in, under, proximal to, or distal to the expandable device.

Aspect 48. The delivery system of aspect 47, wherein the expandable device is an inflatable balloon or an expandable frame.

Aspect 49. The delivery system of aspect 47, wherein the delivery catheter is a balloon catheter that comprises a catheter shaft having an inflation lumen and one or more inflatable balloons disposed at or near a distal end of a catheter shaft.

Aspect 50. The delivery system of aspect 49, wherein at least one of the one or more inflatable balloons is at least partially coated with a therapeutic-agent-containing coating.

Aspect 51. A method of treatment using the delivery system of aspect 47, comprising: (a) introducing the scaffold into the sinus cavity of a patient such that the scaffold is positioned at a delivery location in the sinus cavity and (b) expanding the expandable device while the expandable device is positioned in the lumen of the scaffold.

Aspect 52. The method of aspect 51, wherein the expandable device is a balloon.

Aspect 53. A method of forming a coated scaffold comprising: (a) applying a first coating solution comprising a first solvent, a branched biodegradable polymer and a diisocyanate cross-linking agent to a scaffold and (b) curing the applied first coating solution at elevated temperature, wherein the scaffold is configured for implantation in a sinus cavity and wherein the scaffold has a generally tubular structure having a lumen and comprising a scaffold material.

Aspect 54. The method of aspect 53, wherein the branched biodegradable polymer is a branched hydroxyl terminated poly(lactide-co-caprolactone).

Aspect 55. The method of any of aspects 53-54, wherein the scaffold material comprises poly(lactide-co-glycolide).

Aspect 56. The method of any of aspects 53-54, wherein the first solution further comprises a chain terminator.

Aspect 57. The method of aspect 56, wherein the diisocyanate cross-linking agent is hexamethylene diisocyanate, wherein the chain terminator is 1-dodecanol, or a combination of both.

Aspect 58. The method of any of aspects 53-57, wherein the first solvent comprises dichloromethane and, optionally, anisole.

Aspect 59. The method of any of aspects 53-57, wherein the first solvent comprises ethyl acetate.

Aspect 60. The method of aspect 58 or 59, wherein the scaffold is a braided structure comprising one or more strands of the scaffold material and a plurality of nodes and wherein the coating solution is applied to at least the nodes of the scaffold.

Aspect 61. The method of any of aspects 53-57, wherein the method further comprises applying a second coating solution comprising a second solvent, an additional biodegradable polymer and a therapeutic agent to the scaffold after curing.

Aspect 62. The method of aspect 61, wherein the additional biodegradable polymer is poly(lactide-co-caprolactone).

Aspect 63. The method of any of aspects 61-62, wherein the therapeutic agent is a steroidal anti-inflammatory drug.

Aspect 64. The method of any of aspects 61-62, wherein the therapeutic agent is mometasone furoate.

Aspect 65. The method of aspect 64, wherein the second solvent comprises ethyl formate and anisole.

Aspect 66. The method of any of aspects 61-65, wherein the first coating solution and the second coating solution are applied in a spray process.

Aspect 67. A scaffold formed by the method of any of aspects 53-66.

Aspect 68. The scaffold of any of aspects 1-37, wherein the scaffold material comprises a therapeutic agent.

Aspect 69. The scaffold of aspect 68, wherein the therapeutic agent is a steroidal anti-inflammatory drug.

Aspect 70. The scaffold of any of aspects 15-26, wherein the coating material comprises a therapeutic agent.

Aspect 71. The scaffold of aspect 70, wherein the therapeutic agent is a steroidal anti-inflammatory drug.

Aspect 72. The scaffold of any of aspects 15-26, further comprising an additional conformal coating that comprises an additional coating material and a therapeutic agent.

Aspect 73. The scaffold of aspect 72, wherein the therapeutic agent is a steroidal anti-inflammatory drug.

Aspect A1. An expandable scaffold, wherein the scaffold is adapted to be delivered to a sinus cavity of a human and self-expand to a first width within the sinus cavity and wherein the scaffold is adapted to further expand over time to a second width in vivo as the surrounding sinus cavity enlarges such that the scaffold remains in contact with the sinus cavity.

Aspect A2. The expandable scaffold of aspect A1, wherein the scaffold is adapted to be implanted into a human middle meatus.

Aspect A3. The expandable scaffold of any of aspects A1-A2, wherein the second width is at least 125% of the first width.

Aspect A4. The expandable scaffold of any of aspects A1-A2, wherein the second width is at least 150% of the first width.

Aspect A5. The expandable scaffold of any of aspects A1-A4, wherein the scaffold is adapted to further expand to the second width over a period of at least 6 weeks.

Aspect A6. The expandable scaffold of any of aspects A1-A4, wherein the scaffold is adapted to further expand to the second width over a period of at least 12 weeks.

Aspect A7. The expandable scaffold of any of aspects A1-A6, wherein the scaffold comprises a plurality of braided polymeric strands that comprise a biodegradable polymer and a support coating over the braided polymeric strands that comprises a crosslinked biodegradable elastomer.

Aspect A8. The expandable scaffold of aspect A7, wherein the biodegradable polymer comprises poly(lactide-co-glycolide).

Aspect A9. The expandable scaffold of aspect A7, wherein the biodegradable polymer comprises poly(lactide-co-glycolide) having between 80 mol % and 90 mol % lactic acid residues and between 10 mol % and 20 mol % glycolic acid residues and more particularly comprises poly(lactide-co-glycolide) having between 82 mol % and 87 mol % lactic acid residues and between 13 mol % and 18 mol % glycolic acid residues.

Aspect A10. The expandable scaffold of any of aspects A7-A9, wherein the support coating comprises crosslinked poly(lactide-co-caprolactone).

Aspect A11. The expandable scaffold of any of aspects A7-A9, wherein the support coating comprises crosslinked poly(lactide-co-caprolactone) having a molar percentage of lactide ranging from 30% to 50% and a molar percentage of caprolactone ranging from 50% to 70%, more particularly, having a molar percentage of lactide ranging from 35% to 45% and a molar percentage of caprolactone ranging from 55% to 65%.

Aspect A12. The expandable scaffold of any of aspects A7-A9, wherein the support coating comprises an isocyanate-crosslinked poly(lactide-co-caprolactone).

Aspect A13. The expandable scaffold of aspect A12, wherein to poly(lactide-co-caprolactone) in the support coating is crosslinked with hexamethylene diisocyanate.

Aspect A14. The expandable scaffold of any of aspects A7-A13, wherein the expandable scaffold comprises a therapeutic-agent-containing layer over the support coating that comprises a therapeutic agent and a biodegradable polymer.

Aspect A15. The expandable scaffold of aspect A14, wherein the therapeutic-agent-containing layer comprises poly(lactic acid-co-caprolactone).

Aspect A16. The expandable scaffold of aspect A14, wherein the therapeutic-agent-containing layer comprises poly(lactic acid-co-caprolactone) and mometasone furoate.

Aspect A17. The expandable scaffold of any of aspects A15-A16, wherein the expandable scaffold further comprises a topcoat layer over the therapeutic-agent-containing layer that comprises a blend of poly(lactic acid-co-caprolactone) and polylactic acid (also referred to herein as polylactide).

Aspect A18. The expandable scaffold of aspect A17, wherein the poly(lactide-co-caprolactone) in each of the therapeutic-agent-containing layer and the topcoat layer has a molar percentage of lactide ranging from 60% to 80% and a molar percentage of caprolactone ranging from 20% to 40%.

Aspect A19. The expandable scaffold of aspect A17, wherein poly(lactide-co-caprolactone) in each of the therapeutic-agent-containing layer and the topcoat layer has a molar percentage of lactide ranging from 65% to 75% and a molar percentage of caprolactone ranging from 25% to 35%.

Aspect A20. The expandable scaffold of aspect A17, wherein the blend comprises from 60 to 80 wt % poly(lactic acid-co-caprolactone) and from 20 to 40 wt % polylactic acid.

Aspect A21. The expandable scaffold of aspect A17, wherein the blend comprises from 70 to 80 wt % poly(lactic acid-co-caprolactone) and from 20 to 30 wt % polylactic acid, for example, from 73 to 77 wt % poly(lactic acid-co-caprolactone) and from 23 to 27 wt % polylactic acid.

Aspect A22. The expandable scaffold of aspect A17, wherein the poly(lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 60 to 80 wt % poly(lactic acid-co-caprolactone) and from 20 to 40 wt % polylactic acid, for example, from 70 to 80 wt % poly(lactic acid-co-caprolactone) and from 20 to 30 wt % polylactic acid, more particularly, from 73 to 77 wt % poly(lactic acid-co-caprolactone) and from 23 to 27 wt % polylactic acid.

Aspect A23. The expandable scaffold of any of aspects A14-A22, wherein the therapeutic-agent-containing layer comprises between 5 wt % and 50 wt % mometasone furoate.

Aspect A24. The expandable scaffold of any of aspects A14-A22, wherein the therapeutic-agent-containing layer comprises between 20 wt % and 40 wt % mometasone furoate.

Aspect A25. The expandable scaffold of any of aspects A17-A24, wherein the therapeutic-agent-containing layer ranges from 10 to 20 μm in thickness and the topcoat layer ranges from 1 to 5 μm in thickness.

Aspect A26. The expandable scaffold of any of aspects A17-A24, wherein the therapeutic-agent-containing layer ranges from 10 to 16 μm in thickness and the topcoat layer ranges from 1.2 to 2 μm in thickness.

Aspect A27. A method of treatment comprising implanting an expandable scaffold in accordance with any of aspects A1-A26 into a human sinus cavity.

Aspect A28. The method of aspect A27, wherein the scaffold further expands to the second width in vivo as the surrounding sinus cavity enlarges and wherein the second width is at least 125% of the first width.

Aspect A29. The method of aspect A27, wherein the scaffold further expands to the second width in vivo as the surrounding sinus cavity enlarges and wherein the second width is at least 150% of the first width.

Aspect A30. The method of aspect A27, wherein the scaffold further expands to the second width in vivo as the surrounding sinus cavity enlarges and wherein the second width is at least 200% of the first width.

Aspect A31. The method of any of aspects A27-A31, wherein the scaffold further expands to the second width in vivo as the surrounding sinus cavity enlarges over a period of at least 6 weeks.

Aspect A32. The method of any of aspects A27-A31, wherein the scaffold further expands to the second width in vivo as the surrounding sinus cavity enlarges over a period of at least 12 weeks.

Aspect A33. The method of any of aspects A27-A32, wherein the expandable scaffold is implanted into a human middle meatus.

Aspect A34. The method of aspect A33, wherein the native middle meatus has a width ranging from 2 to 5 mm at the time of scaffold delivery.

Aspect A35. The method of any of aspects A27-A34, wherein the expandable scaffold has an unconstrained diameter ranging from 5 to 25 mm at the time of delivery.

Aspect A36. The method of any of aspects A27-A34, wherein the expandable scaffold has an unconstrained diameter ranging from 9 to 15 mm at the time of delivery.

Aspect A37. The method of any of aspects A27-A34, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect A38. The expandable scaffold of any of aspects A1-A26, wherein the expandable scaffold has an unconstrained diameter ranging from 5 to 25 mm at the time of delivery.

Aspect A39. The expandable scaffold of any of aspects A1-A26, wherein the expandable scaffold has an unconstrained diameter ranging from 9 to 15 mm at the time of delivery.

Aspect A40. The expandable scaffold of any of aspects A1-A26, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect A41, the expandable scaffold of any of aspects A14 to A26, wherein the therapeutic agent is mometasone furoate, and wherein a quantity of mometasone furoate initially present in the scaffold per unit scaffold area ranges from 0.1 µg/mm$^2$ to 20 µg/mm$^2$.

Aspect B1. A method of treatment, comprising delivering an expandable scaffold comprising a therapeutic agent to a native middle meatus of a human patient.

Aspect B2. The method of aspect B1, wherein the native middle meatus has a width ranging from 2 to 5 mm at the time of scaffold delivery.

Aspect B3. The method of any of aspects B1-B2, wherein the expandable scaffold has an unconstrained diameter ranging from 5 to 25 mm at the time of delivery.

Aspect B4. The method of any of aspects B1-B2, wherein the expandable scaffold has an unconstrained diameter ranging from 9 to 15 mm at the time of delivery.

Aspect B5. The method of any of aspects B1-B2, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect B6. The method of any of aspects B1-B5, wherein the scaffold comprises a plurality of braided polymeric strands that comprise a biodegradable polymer and a support coating over the braided polymeric strands that comprises a crosslinked biodegradable elastomer.

Aspect B7. The method of aspect B6, wherein the biodegradable polymer comprises poly(lactide-co-glycolide).

Aspect B8. The method of aspect B6, wherein the biodegradable polymer comprises poly(lactide-co-glycolide) having between 80 mol % and 90 mol % lactic acid residues and between 10 mol % and 20 mol % glycolic acid residues, more particularly, having between 82 mol % and 87 mol % lactic acid residues and between 13 mol % and 18 mol % glycolic acid residues.

Aspect B9. The method of any of aspects B6-B8, wherein the support coating comprises crosslinked poly(lactide-co-caprolactone).

Aspect B10. The method of any of aspects B6-B8, wherein the support coating comprises crosslinked poly(lactide-co-caprolactone) having a molar percentage of lactide ranging from 30% to 50% and a molar percentage of caprolactone ranging from 50% to 70%, more particularly, having a molar percentage of lactide ranging from 35% to 45% and a molar percentage of caprolactone ranging from 55% to 65%.

Aspect B11. The method of any of aspects B6-B10, wherein the support coating comprises isocyanate-crosslinked poly(lactide-co-caprolactone).

Aspect B12. The method of aspect B11, wherein to poly(lactide-co-caprolactone) in the support coating is crosslinked with hexamethylene diisocyanate.

Aspect B13. The method of any of aspects B6-B12, wherein the expandable scaffold comprises a therapeutic-agent-containing layer over the support coating that comprises the therapeutic agent and a biodegradable polymer.

Aspect B14, The method of aspect B13, wherein the therapeutic-agent-containing layer comprises poly(lactic acid-co-caprolactone).

Aspect B15. The method of aspect B13, wherein the therapeutic-agent-containing layer comprises poly(lactic acid-co-caprolactone) and mometasone furoate.

Aspect B16. The method of any of aspects B13-B15, wherein the expandable scaffold further comprising a topcoat layer over the therapeutic-agent-containing layer that comprises a blend of poly(lactic acid-co-caprolactone) and polylactic acid.

Aspect B17. The method of aspect B16, wherein the poly(lactide-co-caprolactone) in each of the therapeutic-agent-containing layer and the topcoat layer has a molar percentage of lactide ranging from 60% to 80% and a molar percentage of caprolactone ranging from 20% to 40%.

Aspect B18. The method of aspect B16, wherein the poly(lactide-co-caprolactone) in each of the therapeutic-agent-containing layer and the topcoat layer has a molar percentage of lactide ranging from 65% to 75% and a molar percentage of caprolactone ranging from 25% to 35%.

Aspect B19. The method of any of aspects B16-B18, wherein the blend comprises from 60 to 80 wt % poly(lactic acid-co-caprolactone) and from 20 to 40 wt % polylactic acid.

Aspect B20. The method of any of aspects B16-B18, wherein the blend comprises from 70 to 80 wt % poly(lactic acid-co-caprolactone) and from 20 to 30 wt % polylactic acid, for example, from 73 to 77 wt % poly(lactic acid-co-caprolactone) and from 23 to 27 wt % polylactic acid.

Aspect B21. The method of aspect B16, wherein the poly(lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 60 to 80 wt % poly(lactic acid-co-caprolactone) and from 20 to 40 wt % polylactic acid, for example, from 70 to 80 wt % poly(lactic acid-co-caprolactone) and from 20 to 30 wt % polylactic acid, more particularly, from 73 to 77 wt % poly(lactic acid-co-caprolactone) and from 23 to 27 wt % polylactic acid.

Aspect B22. The method of any of aspects B13-B21, wherein the therapeutic-agent-containing layer comprises between 5 wt % and 50 wt % mometasone furoate.

Aspect B23. The method of any of aspects B13-B21, wherein the therapeutic-agent-containing layer comprises between 20 wt % and 40 wt % mometasone furoate.

Aspect B24. The method of any of aspects B16-B23, wherein the therapeutic-agent-containing layer ranges from 10 to 20 μm in thickness and the topcoat layer ranges from 1 to 5 μm in thickness.

Aspect B25. The method of any of aspects B16-B23, wherein the therapeutic-agent-containing layer ranges from 10 to 16 μm in thickness and the topcoat layer ranges from 1.2 to 2 μm in thickness.

Aspect B26. The method of any of aspects B1-25, wherein the expandable scaffold is delivered to the native middle meatus using a 2 to 4 mm catheter.

Aspect B27. The method of any of aspects B1-B25, wherein the expandable scaffold releases an effective amount of the therapeutic agent in the native middle meatus for a period of at least 12 weeks.

Aspect B28. The method of any of aspects B1-B27, wherein the scaffold self-expands to a first width within the sinus cavity upon delivery and wherein the scaffold expands over time to a second width in vivo as the surrounding sinus cavity enlarges such that the scaffold remains in contact with the sinus cavity.

Aspect B29. The method of aspect B28, wherein the scaffold further expands to the second width in vivo as the surrounding sinus cavity enlarges and wherein the second width is at least 125% of the first width.

Aspect B30. The method of aspect B28, wherein the scaffold further expands to the second width in vivo as the surrounding sinus cavity enlarges and wherein the second width is at least 150% of the first width.

Aspect B31. The method of aspect B28, wherein the scaffold further expands to the second width in vivo as the surrounding sinus cavity enlarges and wherein the second width is at least 200% of the first width.

Aspect B32. The method of any of aspects B28-30, wherein the scaffold further expands to the second width in vivo as the surrounding sinus cavity enlarges over a period of at least 12 weeks.

Aspect B33. The method of any of aspects B1-B32, wherein the therapeutic agent is mometasone furoate, and wherein a quantity of mometasone furoate initially present in the scaffold per unit scaffold area ranges from 0.1 μg/mm$^2$ to 20 μg/mm$^2$.

Aspect C1. An expandable scaffold adapted for delivery to a human sinus comprising a tubular scaffold comprising a plurality of braided polymeric strands that comprise a biodegradable polymer and a support coating over the braided polymeric strands that comprises a crosslinked biodegradable elastomer, wherein after holding the tubular scaffold in a 34° C., submerged in deionized water for 10 weeks in a compressed state between two parallel flat plates such that the axis of the tubular scaffold is parallel to the parallel flat plates and such that the tubular scaffold is compressed between the parallel flat plates to a point where a first distance between the parallel flat plates is 15% of the initial unconstrained diameter such that the tubular scaffold has a first minimum width measured perpendicular to the axis that is equal to the first distance, and wherein after removal the tubular scaffold from the compressed state for six hours, the minimum width of the tubular scaffold recovers to a second minimum width measured perpendicular to the axis that is at least 150% of the first minimum width.

Aspect C2. The expandable scaffold of aspect C1, wherein the biodegradable polymer comprises poly(lactide-co-glycolide).

Aspect C3. The expandable scaffold of aspect C1, wherein biodegradable polymer comprises poly(lactide-co-glycolide) having between 80 mol % and 90 mol % lactic acid residues and between 10 mol % and 20 mol % glycolic acid residues, more particularly, having between 82 mol % and 87 mol % lactic acid residues and between 13 mol % and 18 mol % glycolic acid residues.

Aspect C4. The expandable scaffold of any of aspects C1-C3, wherein the support coating comprises crosslinked poly(lactide-co-caprolactone).

Aspect C5. The expandable scaffold of any of aspects C1-C3, wherein the support coating comprises crosslinked poly(lactide-co-caprolactone) having a molar percentage of lactide ranging from 30% to 50% and a molar percentage of caprolactone ranging from 50% to 70%, more particularly, having a molar percentage of lactide ranging from 35% to 45% and a molar percentage of caprolactone ranging from 55% to 65%

Aspect C6. The expandable scaffold of any of aspects C1-05, wherein the support coating comprises isocyanate-crosslinked poly(lactide-co-caprolactone).

Aspect C7. The expandable scaffold of aspect C6, wherein to poly(lactide-co-caprolactone) in the support coating is crosslinked with hexamethylene diisocyanate.

Aspect C8. The expandable scaffold of any of aspects C1-C7, wherein the expandable scaffold comprises a therapeutic-agent-containing layer over the support coating that comprises the therapeutic agent and a biodegradable polymer.

Aspect C9. The expandable scaffold of any of aspects C1-C8, wherein the expandable scaffold has an unconstrained diameter ranging from 5 to 25 mm at the time of delivery.

Aspect C10. The expandable scaffold of any of aspects C1-C8, wherein the expandable scaffold has an unconstrained diameter ranging from 9 to 15 mm at the time of delivery.

Aspect C11. The expandable scaffold of any of aspects C1-C8, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

C12. The expandable scaffold of aspects C8, wherein the therapeutic agent is mometasone furoate, and wherein a quantity of mometasone furoate initially present in the scaffold per unit scaffold area ranges from 0.1 μg/mm$^2$ to 20 μg/mm$^2$.

Aspect D1. A method of treatment, comprising delivering an expandable scaffold comprising a therapeutic agent to a sinus cavity of a human patient and wherein the expandable scaffold releases the therapeutic agent for a period of at least 12 weeks after delivery.

Aspect D2. The method of aspect D1, wherein the therapeutic agent is an anti-inflammatory agent and wherein the amount of therapeutic agent is an amount effective to reduce inflammation in the sinus cavity.

Aspect D3. The method of any of aspects D1-D2, wherein the sinus cavity is a native middle meatus.

Aspect D4. The method of aspect D3, wherein the middle meatus has a width ranging from 2-5 mm.

Aspect D5. The method of any of aspects D1-D4, wherein less than 15% of the therapeutic agent is released during the first week.

Aspect D6. The method of aspect D5, wherein 20 to 80% of the therapeutic agent is released during the first 12 weeks, more particularly, wherein 30 to 70% of the therapeutic agent is released during the first 12 weeks, even more particularly, wherein 40 to 60% of the therapeutic agent is released during the first 12 weeks.

Aspect D7. The method of any of aspects D1-D8, wherein the expandable scaffold comprises (a) a plurality of braided polymeric strands that comprise a biodegradable polymer and (b) a therapeutic-agent-containing layer over the braided polymeric strands that comprises the therapeutic agent.

Aspect D8. The method of aspect D7, wherein the braided polymeric strands comprise poly(lactide-co-glycolide).

Aspect D9. The method of aspect D7, wherein the braided polymeric strands comprise poly(lactide-co-glycolide), having a molar percentage of lactide ranging from 80% to 90% and a molar percentage of glycolide ranging from 10% to 20%, more particularly, having a molar percentage of lactide ranging from 82% to 87% and a molar percentage of glycolide ranging from 13% to 18%.

Aspect D10, The method of any of aspects D7-D9, wherein the therapeutic-agent-containing layer comprises poly(lactic acid-co-caprolactone).

Aspect D11. The method of any of aspects D7-D9, wherein the therapeutic-agent-containing layer comprises poly(lactic acid-co-caprolactone) and mometasone furoate.

Aspect D12. The method of any of aspects D10-D11, wherein the expandable scaffold further comprising a topcoat layer over the therapeutic-agent-containing layer that comprises a blend of poly(lactic acid-co-caprolactone) and polylactic acid.

Aspect D13. The method of aspect D12, wherein the poly(lactide-co-caprolactone) in each of the therapeutic-agent-containing layer and the topcoat layer has a molar percentage of lactide ranging from 60% to 80% and a molar percentage of caprolactone ranging from 20% to 40%.

Aspect D14. The method of aspect D12, wherein the poly(lactide-co-caprolactone) in each of the therapeutic-agent-containing layer and the topcoat layer has a molar percentage of lactide ranging from 65% to 75% and a molar percentage of caprolactone ranging from 25% to 35%.

Aspect D15. The method of any of aspects D12-D14, wherein the blend comprises from 60 to 80 wt % poly(lactic acid-co-caprolactone) and from 20 to 40 wt % polylactic acid.

Aspect D16. The method of any of aspects D12-D14, wherein the blend comprises from 70 to 80 wt % poly(lactic acid-co-caprolactone) and from 20 to 30 wt % polylactic acid, for example, from 73 to 77 wt % poly(lactic acid-co-caprolactone) and from 23 to 27 wt % polylactic acid.

Aspect D17. The method of aspect D12, wherein poly(lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 60 to 80 wt % poly(lactic acid-co-caprolactone) and from 20 to 40 wt % polylactic acid, for example, from 70 to 80 wt % poly(lactic acid-co-caprolactone) and from 20 to 30 wt % polylactic acid, more particularly, from 73 to 77 wt % poly(lactic acid-co-caprolactone) and from 23 to 27 wt % polylactic acid.

Aspect D18. The method of any of aspects D7-D17, wherein the therapeutic-agent-containing 1 ayer comprises between 5 wt % and 50 wt % mometasone furoate.

Aspect D19. The method of any of aspects D7-D17, wherein the therapeutic-agent-containing layer comprises between 20 wt % and 40 wt % mometasone furoate.

Aspect D20. The method of any of aspects D12-D19, wherein the therapeutic-agent-containing layer ranges from 10 to 20 µm in thickness and the topcoat layer ranges from 1 to 5 µm in thickness.

Aspect D21. The method of any of aspects D12-D19, wherein the therapeutic-agent-containing layer ranges from 10 to 16 µm in thickness and the topcoat layer ranges from 1.2 to 2 µm in thickness.

Aspect D22. The method of any of aspects D7-D21, wherein the expandable scaffold further comprises a support coating disposed over the braided polymeric strands and under the therapeutic-agent-containing layer.

Aspect D23. The method of aspect D22, wherein the support coating comprises crosslinked poly(lactide-co-caprolactone).

Aspect D24. The method of aspect D22, wherein the support coating comprises crosslinked poly(lactide-co-caprolactone) having a molar percentage of lactide ranging from 30% to 50% and a molar percentage of caprolactone ranging from 50% to 70%, more particularly, having a molar percentage of lactide ranging from 35% to 45% and a molar percentage of caprolactone ranging from 55% to 65%.

Aspect D25. The method of any of aspects D22-D24, wherein the support coating comprises an isocyanate-crosslinked poly(lactide-co-caprolactone).

Aspect D26. The method of aspect D25, wherein to poly(lactide-co-caprolactone) in the support coating is crosslinked with hexamethylene diisocyanate.

Aspect D27. The expandable scaffold of any of aspects D1-D26, wherein the expandable scaffold has an unconstrained diameter ranging from 5 to 25 mm at the time of delivery.

Aspect D28. The expandable scaffold of any of aspects D1-D26, wherein the expandable scaffold has an unconstrained diameter ranging from 9 to 15 mm at the time of delivery.

Aspect D29. The expandable scaffold of any of aspects D1-D26, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect D30. The method of any of aspects D1-D29, wherein the scaffold self-expands to a first width within the sinus cavity upon delivery and wherein the scaffold expands over time to a second width in vivo as the surrounding sinus cavity enlarges such that the scaffold remains in contact with the sinus cavity.

Aspect D31. The method of aspect D30, wherein the scaffold further expands to the second width in vivo as the surrounding sinus cavity enlarges and wherein the second width is at least 125% of the first width.

Aspect D32. The method of aspect D30, wherein the scaffold further expands to the second width in vivo as the surrounding sinus cavity enlarges and wherein the second width is at least 150% of the first width.

Aspect D33. The method of aspect D30, wherein the scaffold further expands to the second width in vivo as the surrounding sinus cavity enlarges and wherein the second width is at least 200% of the first width.

Aspect D34. The method of any of aspects D30-D33, wherein the scaffold further expands to the second width in vivo as the surrounding sinus cavity enlarges over a period of at least 12 weeks.

Aspect D35. The method of any of aspects D1-D34, wherein the therapeutic agent is mometasone furoate, and wherein a quantity of mometasone furoate initially present in the scaffold per unit scaffold area ranges from 0.1 µg/mm$^2$ to 20 µg/mm$^2$. Aspect E1. A method of treatment, comprising delivering an expandable scaffold comprising a therapeutic agent to a sinus cavity of a human patient, wherein the expandable scaffold releases the therapeutic agent for a period of 12 weeks or less.

Aspect E2. The method of aspect E1, wherein the expandable scaffold releases an effective amount of therapeutic agent for a period of 6 weeks or less.

Aspect E3. The method of any of aspects E1- E2, wherein 10% to 30% of the therapeutic agent is released during the first week.

Aspect E4. The method of any of aspects E1- E2, wherein 20% to 50% of the therapeutic agent is released during the first two weeks.

Aspect E5. The method of any of aspects E1-E4, wherein the scaffold self-expands to a first width within the sinus cavity upon delivery and wherein the scaffold expands over time to a second width in vivo as the surrounding sinus cavity enlarges such that the scaffold remains in contact with the sinus cavity.

Aspect E6. The method of aspect E5, wherein the scaffold further expands to the second width in vivo as the surrounding sinus cavity enlarges and wherein the second width is at least 125% of the first width.

Aspect E7. The method of aspect E5, wherein the scaffold further expands to the second width in vivo as the surrounding sinus cavity enlarges and wherein the second width is at least 150% of the first width.

Aspect E8. The method of aspect E5, wherein the scaffold further expands to the second width in vivo as the surrounding sinus cavity enlarges and wherein the second width is at least 200% of the first width.

Aspect E9. The method of any of aspects E1-E8, wherein the expandable scaffold is implanted into a human middle meatus.

Aspect E10. The method of aspect E9, wherein the native middle meatus has a width ranging from 2 to 5 mm at the time of scaffold delivery.

Aspect E11. The method of any of aspects E1- E10, wherein the expandable scaffold has an unconstrained diameter ranging from 5 to 25 mm at the time of delivery.

Aspect E12. The method of any of aspects E1- E10, wherein the expandable scaffold has an unconstrained diameter ranging from 9 to 15 mm at the time of delivery.

Aspect E13. The method of any of aspects E1- E10, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect E14. The method of any of aspects E1-E13, wherein the therapeutic agent is mometasone furoate, and wherein a quantity of mometasone furoate initially present in the scaffold per unit scaffold area ranges from 0.1 µg/mm$^2$ to 20 µg/mm$^2$.

Aspect F1. A method of treatment, comprising delivering an expandable scaffold comprising a therapeutic agent is delivered to a sinus cavity of a human patient, wherein the expandable scaffold releases an amount of therapeutic agent for a period of at least 26 weeks, and wherein the therapeutic agent is released in a substantially linear fashion.

Aspect F2. The method of aspect F1, wherein the therapeutic agent is an anti-inflammatory agent and wherein the amount of therapeutic agent is an amount effective to reduce inflammation in the sinus cavity.

Aspect F3. The method of any of aspects F1-F2, wherein the absolute quantity of therapeutic agent released into the human patient over any one week period does not vary more than 33% between week 3 and week 26 of implantation.

Aspect F4. The method of any of aspects F1-F3, wherein the expandable scaffold is delivered to a native middle meatus of a human patient.

Aspect F5. The method of any of aspects F1-F4, wherein the expandable scaffold has an unconstrained diameter ranging from 5 to 25 mm at the time of delivery, more particularly, an unconstrained diameter ranging from 9 to 15 mm at the time of delivery.

Aspect F6. The method of any of aspects F1-F5, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect F7. The method of any of aspects F1-F6, wherein the expandable scaffold comprises a plurality of braided polymeric strands that comprise a biodegradable polymer and a therapeutic-agent-containing layer over braided polymeric strands that comprises a biodegradable polymer and the therapeutic agent.

Aspect F8. The method of aspect F7, wherein the braided polymeric strands comprise poly(lactide-co-glycolide).

Aspect F9. The method of aspect F7, wherein the braided polymeric strands comprise poly(lactide-co-glycolide) having a molar percentage of lactide ranging from 82% to 87% and a molar percentage of glycolide ranging from 13% to 18%.

Aspect F10, The method of any of aspects F7-F9, wherein the therapeutic-agent-containing layer comprises poly(lactic acid-co-caprolactone).

Aspect F11. The method of any of aspects F7-F9, wherein the therapeutic-agent-containing layer comprises poly(lactic acid-co-caprolactone) and mometasone furoate.

Aspect F12. The method of any of aspects F7-F11, wherein the expandable scaffold further comprising a topcoat layer over the therapeutic-agent-containing layer that comprises a blend of poly(lactic acid-co-caprolactone) and polylactic acid.

Aspect F13. The method of aspect F12, wherein poly (lactide-co-caprolactone) in each of the therapeutic-agent-containing layer and the topcoat layer has a molar percentage of lactide ranging from 60% to 80% and a molar percentage of caprolactone ranging from 20% to 40%.

Aspect F14. The method of aspect F12, wherein poly (lactide-co-caprolactone) in each of the therapeutic-agent-containing layer and the topcoat layer has a molar percentage of lactide ranging from 65% to 75% and a molar percentage of caprolactone ranging from 25% to 35%.

Aspect F15. The method of aspect F12, wherein the blend comprises from 60 to 80 wt % poly(lactic acid-co-caprolactone) and from 20 to 40 wt % polylactic acid.

Aspect F16. The method of aspect F12, wherein the blend comprises from 70 to 80 wt % poly(lactic acid-co-caprolactone) and from 20 to 30 wt % polylactic acid, for example, from 73 to 77 wt % poly(lactic acid-co-caprolactone) and from 23 to 27 wt % polylactic acid.

Aspect F17. The method of aspect F12, wherein poly (lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 60 to 80 wt % poly(lactic acid-co-caprolactone) and from 20 to 40 wt % polylactic acid, for example, from 70 to 80 wt % poly(lactic acid-co-caprolactone) and from 20 to 30 wt % polylactic acid, more particularly, from 73 to 77 wt % poly(lactic acid-co-caprolactone) and from 23 to 27 wt % polylactic acid.

Aspect F18. The method of any of aspects F7-F17, wherein the therapeutic-agent-containing layer comprises between 5 wt % and 50 wt % mometasone furoate.

Aspect F19. The method of any of aspects F7-F17, wherein the therapeutic-agent-containing layer comprises between 20 wt % and 40 wt % mometasone furoate.

Aspect F20. The method of any of aspects F12-F19, wherein the therapeutic-agent-containing layer ranges from 10 to 20 µm in thickness and the topcoat layer ranges from 1 to 5 µm in thickness.

Aspect F21. The method of any of aspects F12-F19, wherein the therapeutic-agent-containing layer ranges from 10 to 16 µm in thickness and the topcoat layer ranges from 1.2 to 2 µm in thickness.

Aspect F22. The method of any of aspects F7-F21, wherein the expandable scaffold further comprises a support coating disposed over the braided polymeric strands and under the therapeutic-agent-containing layer.

Aspect F23. The method of aspect F22, wherein the support coating comprises crosslinked poly(lactide-co-caprolactone).

Aspect F24. The method of aspect F22, wherein the support coating comprises crosslinked poly(lactide-co-caprolactone) having a molar percentage of lactide ranging from 30% to 50% and a molar percentage of caprolactone ranging from 50% to 70%.

Aspect F25. The method of aspect F22, wherein the support coating comprises an isocyanate-crosslinked poly (lactide-co-caprolactone).

Aspect F26. The method of aspect F25, wherein to poly(lactide-co-caprolactone) in the support coating is crosslinked with hexamethylene diisocyanate.

Aspect F27. The method of any of aspects F1-F26, wherein the scaffold self-expands to a first width within the sinus cavity upon delivery and wherein the scaffold expands over time to a second width in vivo as the surrounding sinus cavity enlarges such that the scaffold remains in contact with the sinus cavity.

Aspect F28. The method of aspect F27, wherein the scaffold further expands to the second width in vivo as the surrounding sinus cavity enlarges and wherein the second width is at least 125% of the first width.

Aspect F29. The method of aspect F27, wherein the scaffold further expands to the second width in vivo as the surrounding sinus cavity enlarges and wherein the second width is at least 150% of the first width.

Aspect F30. The method of aspect F27, wherein the scaffold further expands to the second width in vivo as the surrounding sinus cavity enlarges and wherein the second width is at least 200% of the first width.

Aspect F31. The method of any of aspects F27-F30, wherein the scaffold further expands to the second width in vivo as the surrounding sinus cavity enlarges over a period of at least 6 weeks.

Aspect F32. The method of any of aspects F27-F30, wherein the scaffold further expands to the second width in vivo as the surrounding sinus cavity enlarges over a period of at least 26 weeks.

Aspect F33. The method of any of aspects F1-F32, wherein the therapeutic agent is mometasone furoate, and wherein a quantity of mometasone furoate initially present in the scaffold per unit scaffold area ranges from 0.1 µg/mm$^2$ to 20 µg/mm$^2$.

Aspect G1. A method of treatment, comprising delivering an expandable scaffold comprising a therapeutic agent to a sinus cavity of a human patient, wherein the expandable scaffold is one for which, when submersed in a pH 7.4 PBS buffer solution containing 2% wt % SDS at 37° C. under gentle shaking on a rotary shaker and the buffer solution is removed completely on a weekly basis as a sample for therapeutic agent quantification and replaced with fresh buffer, a quantity of therapeutic agent released in each sample, relative to a total amount of therapeutic agent originally in the scaffold, ranges from 1% to 10%, beginning with the second week sample and extending up to the twelfth week sample. (In other words, samples are taken at 1 week of submersion, at 2 weeks of submersion, at 3 weeks of submersion, at 4 weeks of submersion, at 5 weeks of submersion, at 6 weeks of submersion, at 7 weeks of submersion, at 8 weeks of submersion, at 9 weeks of submersion, at 10 weeks of submersion, at 11 weeks of submersion and at 12 weeks of submersion, and the quantity of therapeutic agent released in each sample, relative to a total amount of therapeutic agent originally in the scaffold, within a given week is calculated by dividing the quantified (i.e., measured) total amount of therapeutic agent released by the scaffold during that week by the total amount of therapeutic agent originally in the scaffold, and the calculated values for the samples taken at 2, 3, 4, 5, 6, 7, 8, 9, 10, 11 and 12 weeks of submersion range from 1% to 10%.)

Aspect G2. The method of aspect G1, wherein the absolute quantity of therapeutic agent released in each sample does not vary by more than 33% between any two samples, beginning with the second week sample and extending up to the twelfth week sample.

Aspect G3. The method of any of aspects G1-G2, wherein the quantity of therapeutic agent released in each sample, relative to a total amount of therapeutic agent originally in the scaffold, ranges from 5% to 9%, beginning with the second week sample and extending up to the twelfth week sample.

Aspect G4. The method of any of aspects G1-G2, wherein the quantity of therapeutic agent released in each sample, relative to a total amount of therapeutic agent originally in the scaffold, ranges from 6% to 8%, beginning with the second week sample and extending up to the twelfth week sample.

Aspect G5. The method of any of aspects G1-G4, wherein the therapeutic agent is mometasone furoate.

Aspect G6. The method of any of aspects G1-G5, wherein the expandable scaffold comprises (a) a plurality of braided polymeric strands that comprise a biodegradable polymer and (b) a therapeutic-agent-containing layer over the braided polymeric strands that comprises the therapeutic agent.

Aspect G7. The method of aspect G6, wherein the braided polymeric strands comprise poly(lactide-co-glycolide).

Aspect G8. The method of aspect G6, wherein the braided polymeric strands comprise poly(lactide-co-glycolide) having a molar percentage of lactide ranging from 82% to 87% and a molar percentage of glycolide ranging from 13% to 18%.

Aspect G9, The method of any of aspects G6-G8, wherein the therapeutic-agent-containing layer comprises poly(lactic acid-co-caprolactone).

Aspect G10. The method of any of aspects G6-G8, wherein the therapeutic-agent-containing layer comprises poly(lactic acid-co-caprolactone) and mometasone furoate.

Aspect G11. The method of any of aspects G6-G9, wherein the expandable scaffold further comprising a topcoat layer over the therapeutic-agent-containing layer that comprises a blend of poly(lactic acid-co-caprolactone) and polylactic acid.

Aspect G12. The method of aspect G11, wherein poly(lactide-co-caprolactone) in each of the therapeutic-agent-containing layer and the topcoat layer has a molar percentage of lactide ranging from 60% to 80% and a molar percentage of caprolactone ranging from 20% to 40%.

Aspect G13. The method of aspect G11, wherein poly(lactide-co-caprolactone) in each of the therapeutic-agent-containing layer and the topcoat layer has a molar percentage of lactide ranging from 65% to 75% and a molar percentage of caprolactone ranging from 25% to 35%.

Aspect G14. The method of aspect G11, wherein the blend comprises from 60 to 80 wt % poly(lactic acid-co-caprolactone) and from 20 to 40 wt % polylactic acid.

Aspect G15. The method of aspect G11, wherein the blend comprises from 70 to 80 wt % poly(lactic acid-co-caprolactone) and from 20 to 30 wt % polylactic acid, for example, from 73 to 77 wt % poly(lactic acid-co-caprolactone) and from 23 to 27 wt % polylactic acid.

Aspect G16. The method of aspect G11, wherein poly(lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 60 to 80 wt % poly(lactic acid-co-caprolactone) and from 20 to 40 wt % polylactic acid, for example, from 70 to 80 wt % poly(lactic acid-co-caprolactone) and from 20 to 30 wt % polylactic acid, more particularly, from 73 to 77 wt % poly(lactic acid-co-caprolactone) and from 23 to 27 wt % polylactic acid.

Aspect G17. The method of any of aspects G6-G16, wherein the therapeutic-agent-containing layer comprises between 5 wt % and 50 wt % mometasone furoate.

Aspect G18. The method of any of aspects G6-G16, wherein the therapeutic-agent-containing layer comprises between 20 wt % and 40 wt % mometasone furoate.

Aspect G19. The method of any of aspects G6-G18, wherein the therapeutic-agent-containing layer ranges from 10 to 20 μm in thickness and the topcoat layer ranges from 1 to 5 μm in thickness.

Aspect G20. The method of any of aspects G11-G18, wherein the therapeutic-agent-containing layer ranges from 10 to 16 μm in thickness and the topcoat layer ranges from 1.2 to 2 μm in thickness.

Aspect G 21. The method of any of aspects G11-G20, wherein the expandable scaffold further comprises a support coating disposed over the braided polymeric strands and under the therapeutic-agent-containing layer.

Aspect G22. The method of aspect G21, wherein the support coating comprises crosslinked poly(lactide-co-caprolactone).

Aspect G23. The method of aspect G21, wherein the support coating comprises crosslinked poly(lactide-co-caprolactone) having a molar percentage of lactide ranging from 30% to 50% and a molar percentage of caprolactone ranging from 50% to 70%.

Aspect G24. The method of aspect G21, wherein the support coating comprises an isocyanate-crosslinked poly(lactide-co-caprolactone).

Aspect G25. The method of aspect G24, wherein to poly(lactide-co-caprolactone) in the support coating is crosslinked with hexamethylene diisocyanate.

Aspect G26. The method of any of aspects G1-G25, wherein the scaffold self-expands to a first width within the sinus cavity upon delivery and wherein the scaffold further expands over time to a second width in vivo as the surrounding sinus cavity enlarges such that the scaffold remains in contact with the sinus cavity.

Aspect G27. The method of aspect G26, wherein the second width is at least 125% of the first width.

Aspect G28. The method Aspect G26, wherein the second width is at least 150% of the first width.

Aspect G29. The method of any of aspects G26-G28, wherein the scaffold further expands to the second width over a period of at least 13 weeks.

Aspect G30. The method of any of aspects G26-G28, wherein the scaffold further expands to the second width over a period of at least 26 weeks.

Aspect G31. The method of any of aspects G1-G30, wherein the scaffold is implanted into a human middle meatus.

Aspect G33. The method of aspect G31, wherein the expandable scaffold is delivered to the native middle meatus using a 2 to 4 mm catheter.

Aspect G34. The method of any of aspects G1-G33, wherein the expandable scaffold has an unconstrained diameter ranging from 5 to 25 mm at the time of delivery.

Aspect G35. The method of any of aspects G1-G33, wherein the expandable scaffold has an unconstrained diameter ranging from 9 to 15 mm at the time of delivery.

Aspect G36. The method of any of aspects G1-G33, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect G37. The method of any of aspects G1-G36, wherein the therapeutic agent is mometasone furoate, and wherein a quantity of mometasone furoate initially present in the scaffold per unit scaffold area ranges from 0.1 µg/mm² to 20 µg/mm².

Aspect H1. A method of treatment, comprising delivering an expandable scaffold comprising a therapeutic agent to a sinus cavity of a human patient, wherein the expandable scaffold is one for which, when submersed in a pH 7.4 PBS buffer solution containing 2% wt % SDS at 37° C. under gentle shaking on a rotary shaker and the buffer solution is removed completely on a weekly basis as a sample for therapeutic agent quantification and replaced with fresh buffer, a quantity of therapeutic agent released per unit scaffold area in each sample, beginning with the second week sample and extending up to the twelfth week sample, ranges from 0.05 to 4 µg/mm²/week, where scaffold area is equal to πDL, where D is the manufactured diameter of the scaffold and L is the manufactured length of the scaffold. (In other words, samples are taken at 1 week of submersion, at 2 weeks of submersion, at 3 weeks of submersion, at 4 weeks of submersion, at 5 weeks of submersion, at 6 weeks of submersion, at 7 weeks of submersion, at 8 weeks of submersion, at 9 weeks of submersion, at 10 weeks of submersion, at 11 weeks of submersion and at 12 weeks of submersion, and the quantity of therapeutic agent released per unit scaffold area within a given week is calculated by dividing the quantified (i.e., measured) total amount of therapeutic agent released by the scaffold into the sample by the scaffold area (i.e., πDL), and the calculated values for the samples taken at 2, 3, 4, 5, 6, 7, 8, 9, 10, 11 and 12 weeks of submersion are within the range of 0.05 to 4 µg/mm²/week.)

Aspect H2. The method of aspect H1, wherein the quantity of therapeutic agent released per unit scaffold area in each sample, beginning with the second week sample and extending up to the twelfth week sample, ranges from 0.1 to 1 µg/mm²/week Aspect H3. The method of any of aspects H1-H2, wherein the quantity of therapeutic agent released per unit scaffold area in each sample, beginning with the second week sample and extending up to the twelfth week sample, does not vary more than 33% between any to two samples.

Aspect H4. The method of any of aspects H1-H3, wherein the therapeutic agent is mometasone furoate.

Aspect H5. The method of any of aspects H1-H4, wherein the expandable scaffold comprises (a) a plurality of braided polymeric strands that comprise a biodegradable polymer and (b) a therapeutic-agent-containing layer over the braided polymeric strands that comprises the therapeutic agent.

Aspect H6. The method of aspect H5, wherein the braided polymeric strands comprise poly(lactide-co-glycolide).

Aspect H7. The method of aspect H5, wherein the braided polymeric strands comprise poly(lactide-co-glycolide) having a molar percentage of lactide ranging from 80% to 90% and a molar percentage of glycolide ranging from 10% to 20%.

Aspect H8. The method of aspect H5, wherein the braided polymeric strands comprise poly(lactide-co-glycolide) having a molar percentage of lactide ranging from 82% to 87% and a molar percentage of glycolide ranging from 13% to 18%.

Aspect H9, The method of any of aspects H5-H8, wherein the therapeutic-agent-containing layer comprises poly(lactic acid-co-caprolactone).

Aspect H10. The method of any of aspects H5-H8, wherein the therapeutic-agent-containing layer comprises poly(lactic acid-co-caprolactone) and mometasone furoate.

Aspect H11. The method of any of aspects H5-H9, wherein the expandable scaffold further comprising a topcoat layer over the therapeutic-agent-containing layer that comprises a blend of poly(lactic acid-co-caprolactone) and polylactic acid.

Aspect H12. The method of aspect H11, wherein poly (lactide-co-caprolactone) in each of the therapeutic-agent-containing layer and the topcoat layer has a molar percentage of lactide ranging from 60% to 80% and a molar percentage of caprolactone ranging from 20% to 40%.

Aspect H13. The method of aspect H11, wherein poly (lactide-co-caprolactone) in each of the therapeutic-agent-containing layer and the topcoat layer has a molar percentage of lactide ranging from 65% to 75% and a molar percentage of caprolactone ranging from 25% to 35%.

Aspect H14. The method of aspect H11, wherein the blend comprises from 60 to 80 wt % poly(lactic acid-co-caprolactone) and from 20 to 40 wt % polylactic acid.

Aspect H15. The method of aspect H11, wherein the blend comprises from 70 to 80 wt % poly(lactic acid-co-caprolactone) and from 20 to 30 wt % polylactic acid, for example, from 73 to 77 wt % poly(lactic acid-co-caprolactone) and from 23 to 27 wt % polylactic acid.

Aspect H16. The method of aspect H11, wherein poly (lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 60 to 80 wt % poly(lactic acid-co-caprolactone) and from 20 to 40 wt % polylactic acid, for example, from 70 to 80 wt % poly(lactic acid-co-caprolactone) and from 20 to 30 wt % polylactic acid, more particularly, from 73 to 77 wt % poly(lactic acid-co-caprolactone) and from 23 to 27 wt % polylactic acid.

Aspect H17. The method of any of aspects H5-H16, wherein the therapeutic-agent-containing layer comprises between 5 wt % and 50 wt % mometasone furoate.

Aspect H18. The method of any of aspects H6-H16, wherein the therapeutic-agent-containing layer comprises between 20 wt % and 40 wt % mometasone furoate.

Aspect H19. The method of any of aspects H11-H18, wherein the therapeutic-agent-containing layer ranges from 10 to 20 µm in thickness and the topcoat layer ranges from 1 to 5 µm in thickness.

Aspect H20. The method of any of aspects H11-H18, wherein the therapeutic-agent-containing layer ranges from 10 to 16 µm in thickness and the topcoat layer ranges from 1.2 to 2 µm in thickness.

Aspect H 21. The method of any of aspects H5-H20, wherein the expandable scaffold further comprises a support coating disposed over the braided polymeric strands and under the therapeutic-agent-containing layer.

Aspect H22. The method of aspect H21, wherein the support coating comprises crosslinked poly(lactide-co-caprolactone).

Aspect H23. The method of aspect H21, wherein the support coating comprises crosslinked poly(lactide-co-caprolactone) having a molar percentage of lactide ranging from 30% to 50% and a molar percentage of caprolactone ranging from 50% to 70%.

Aspect H24. The method of aspect H21, wherein the support coating comprises an isocyanate-crosslinked poly (lactide-co-caprolactone).

Aspect H25. The method of aspect H24, wherein to poly(lactide-co-caprolactone) in the support coating is crosslinked with hexamethylene diisocyanate.

Aspect H26. The method of any of aspects H1-H25, wherein the scaffold self-expands to a first width within the sinus cavity upon delivery and wherein the scaffold further expands over time to a second width in vivo as the surrounding sinus cavity enlarges such that the scaffold remains in contact with the sinus cavity.

Aspect H27. The method of aspect H26, wherein the second width is at least 125% of the first width.

Aspect H28. The method Aspect H26, wherein the second width is at least 150% of the first width.

Aspect H29. The method of any of aspects H26-H28, wherein the scaffold further expands to the second width over a period of at least 13 weeks.

Aspect H30. The method of any of aspects H26-H28, wherein the scaffold further expands to the second width over a period of at least 26 weeks.

Aspect H31. The method of any of aspects H1-H30, wherein the scaffold is implanted into a human middle meatus.

Aspect H33. The method of aspect H31, wherein the expandable scaffold is delivered to the native middle meatus using a 2 to 4 mm catheter.

Aspect H34. The method of any of aspects H1-H33, wherein the expandable scaffold has an unconstrained diameter ranging from 5 to 25 mm at the time of delivery.

Aspect H35. The method of any of aspects H1-H33, wherein the expandable scaffold has an unconstrained diameter ranging from 9 to 15 mm at the time of delivery.

Aspect H36. The method of any of aspects H1-H33, wherein the expandable scaffold is selected from an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

Aspect H37. The method of any of aspects H1-H36, wherein the therapeutic agent is mometasone furoate, and wherein a quantity of mometasone furoate initially present in the scaffold per unit scaffold area ranges from 0.1 µg/mm² to 20 µg/mm².

Additional aspects and embodiments of the present disclosure are discussed in the detailed description set forth below.

BRIEF DESCRIPTION OF THE DRAWINGS

Non-limiting embodiments of the present disclosure are described by way of example with reference to the accompanying figures, which are schematic and not intended to necessarily be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures:

FIG. 13 is a schematic side view of a conformal tube, in accordance with an embodiment of the present disclosure.

FIG. 14A is a schematic perspective view of a conformal tube with an associated three-dimensional support structure in expanded form, in accordance with an embodiment of the present disclosure.

FIG. 14B is a schematic end view of a conformal tube with an associated three-dimensional support structure in crimped form, in accordance with an embodiment of the present disclosure.

FIG. 15 is a schematic side view of a scaffold in the form of a unitary polymeric structure, in accordance with an embodiment of the present disclosure.

FIG. 28A, PLGA(10:90) scaffold without anisole co-solvent; FIG. 28B, PLGA(10:90) scaffold with anisole co-solvent; FIG. 28C, PLGA(75:25) scaffold without anisole co-solvent; FIG. 28D PLGA(75:25) with anisole co-solvent.

FIGS. 29A-29C show optical images of coated scaffolds with and without anisole as a co-solvent during spray-coating as follows: FIG. 29A scaffold coated with 62 wt % elastomer relative to the weight of the base braid from solution without anisole as a co-solvent; FIG. 29B scaffold coated with 63 wt % elastomer from solution containing anisole as a co-solvent; and FIG. 29C scaffold coated with 100 wt % elastomer from solution containing anisole as a co-solvent.

DETAILED DESCRIPTION

Figure 1A:
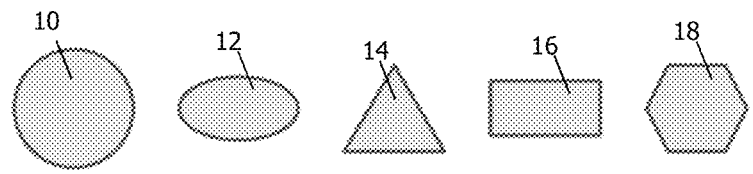
FIG. 1A schematically illustrates various fiber cross-sections, in accordance with embodiments of the present disclosure.

The implantable medical devices of the present disclosure are generally tubular devices, which devices are self-expanding devices in various embodiments. As used herein, "device," "scaffold," "stent", "carrier" and "implant" may be used synonymously. Also as used herein, "self-expanding" is intended to include devices that are crimped to a reduced delivery configuration for delivery into the body, and thereafter tend to expand to a larger suitable configuration once released from the delivery configuration, either without the aid of any additional expansion devices or with the partial aid of balloon-assisted or similarly-assisted expansion. As used herein, "strength" and "stiffness" may be used synonymously to mean the resistance of the medical scaffolds of the present disclosure to deformation by radial forces or a force applied by the scaffolds against a static abutting object. Examples of strength and stiffness measurements, as used to characterize the medical scaffolds of the present disclosure, include radial resistive force and chronic outward force, as further described herein.

Scaffolds in accordance with the present disclosure are typically tubular devices which may be of various sizes, including a variety of diameters and lengths, and which may be used for a variety of sinus applications. In the case of objects of non-circular cross-section, "diameter" denotes width. In certain beneficial embodiments, the as-manufactured (or unconstrained) diameter of the scaffold may range from 5 mm or less to 60 mm or more, for example, ranging from 5 mm to 10 mm to 15 mm to 20 mm to 25 mm to 30 mm to 35 mm to 40 mm or 50 mm to 60 mm (i.e., ranging between any two of the preceding numerical values), commonly ranging from 5 to 13 mm or from 15 to 30 mm. In certain beneficial embodiments, the as-manufactured (or unconstrained) length may range from 5 mm or less to 30 mm or more, for example, ranging from 5 mm to 10 mm to 15 mm to 20 mm to 25 mm or 30 mm (i.e., ranging between any two of the preceding numerical values), commonly ranging from 10 mm to 20 mm.

In certain beneficial embodiments, scaffold mass may range from 1 to 20 mg/mm of length.

Unless indicated otherwise, scaffold diameters and scaffold lengths given herein refer to unconstrained (manufactured) diameters and lengths.

The many scaffold embodiments of the present disclosure are self-expanding in that they are manufactured at a first diameter, subsequently reduced or "crimped" to a second, reduced diameter for placement within a delivery catheter, and self-expand towards the first diameter when extruded from the delivery catheter at an implantation site. The first diameter may be at least 10% larger than the diameter of the bodily lumen into which it is implanted in some embodiments. The scaffold may be designed to recover at least about 70%, at least about 80%, at least about 90%, up to about 100% of its manufactured, first diameter, in some embodiments.

Scaffolds in accordance with the present disclosure are provided with expansion and mechanical properties suitable to render the scaffolds effective for its intended purpose in the sinus cavities. Two measures of such mechanical properties that are used herein are "radial resistive force" ("RRF") and "chronic outward force" ("COF"). RRF is the force that the scaffold applies in reaction to a crimping force, and COF is the force that the scaffold applies against a static abutting surface. In certain embodiments, the scaffolds are configured to have a relatively high RRF to be able to hold open bodily lumens, cavities, and nasal features, and the like, yet have a relatively low COF so as to avoid applying possibly injurious forces against the walls of bodily lumens, optic nerve, brain, or the like. For example, the scaffolds of the present disclosure preferably expand to from 70 to 100% of their as-manufactured configuration after being crimped, have an RRF ranging from 50 to 300 mmHg, and/or have an acute COF (at the time of delivery into a sinus cavity) ranging from 10 to 100 mmHg.

Scaffolds in accordance with the present disclosure may be formed from a variety of polymeric and non-polymeric materials. Scaffolds in accordance with the present disclosure may be biodegradable or non-biodegradable, or be a combination of both biodegradable and non-biodegradable materials. Where biodegradable, the scaffolds may be fully absorbed, for example, within as little as three weeks or less to as long as 52 weeks or more following placement within a sinus cavity of a patient. In some embodiments, the generally tubular structures may become fully absorbed at some time after 12 weeks of placement and before 32 weeks of placement. Biodegradable devices may also be eliminated though nasal irrigation in other embodiments, as opposed to absorption into nasal mucosa. Devices may also be designed such that discrete portion(s) resorb leading to breakup into predetermined small pieces (typically <10 mm or more typically <5 mm in longest dimension) that can be eliminated from the sinuses and nasal cavity through normal mucocilliary action, leading to swallowing or expulsion from the nose. In this way, the amount of acidic resorption byproducts (e.g., lactic acid, glycolic acid) which are in contact with the sinus or nasal cavity surfaces may be reduced. This can reduce irritation or inflammation of these and surrounding tissues. Additives of a basic nature may also be added to the devices in some embodiments to neutralize the acidic byproducts, which may reduce the inflammatory response associated with the same. Moreover, multiple materials that bioresorb at different rates may also be combined in some embodiments to reduce the amount of material degrading at any one time and hence the biological response.

In various embodiments, the implantable scaffolds may comprise a generally tubular structure comprising scaffolding material. Scaffolds in accordance with the present disclosure may be fiber-based or non-fiber-based.

In various embodiments, the scaffolding material may be a biodegradable scaffolding material, typically, a biodegradable scaffolding material that comprises one or more biodegradable polymers. Non-limiting examples of biodegradable polymers for forming the biodegradable scaffolding material include biodegradable polyesters, polycarbonates, polyhydroxyalkanoates, polyanhydrides, and polyorthoesters, non-limiting examples of which include homopolymers of lactic acid (PLA), homopolymers glycolic acid (PGA), homopolymers of trimethylene carbonate (PTMC), homopolymers of caprolactone (PCL), homopolymers of polypropylene fumarate, and homopolymers of dioxanone (PDO), as well as copolymers that comprise two or more of the preceding monomers, for example, poly(lactic acid-co-glycolic acid) (PLGA), poly(lactic acid-co-caprolactone) (PLCL) and poly(glycolic acid-co-caprolactone) (PGCL). Preferred copolymers include PLGA having a molar percentage of lactic acid ranging from 10 to 90% and a molar percentage of glycolic acid ranging from 90 to 10%, more typically lactic acid ranging from 10 to 75% and a molar percentage of glycolic acid ranging from 90 to 25%; for example, PLGA 75:25 (mol/mol) or PLGA (10:90) (mol/mol) may be employed in some embodiments. The composition of PLGA polymers within these ranges may be optimized to meet the mechanical property and degradation requirements of the specific application for which the scaffold is used. In certain embodiments, the biodegradable scaffolding material may comprise a prodrug-based polymer, for example, polyaspirin, which can be used as a single-component or a subcomponent of the generally tubular structure to make scaffolds with degradation-controlled therapeutic-agent-releasing capability.

In various embodiments, the scaffolding material may be a non-biodegradable scaffolding material, typically a non-biodegradable scaffolding material that comprises one or more non-biodegradable polymers. Non-limiting examples of non-biodegradable polymers for forming the non-biodegradable scaffolding material include polyolefins such as polyethylene (HDPE and LDPE) and polypropylene, halogenated polyolefins such as polyvinyl chloride (PVC) and fluoropolymers including polytetrafluoroethylene (PTFE) and perfluoroalkoxy alkanes (PFAs), polyaromatics such as polystyrene, polyesters such as polyethylene terephthalate (PET), polyamides such as nylon, silicones, mucoadhesive materials and biostable polyurethanes (PU).

Scaffolds in accordance with the present disclosure may optionally comprise a coating formed of a coating material that at least partially coats the scaffolding material.

Coatings may be applied for various purposes including mechanical property enhancement, degradation control, and therapeutic agent release and control. Coatings may cover all or a portion of the scaffolds or, in fiber-based techniques, all or a portion of the filaments or strands forming the scaffolds. As used herein "strands" and "filaments" may be used interchangeably and include single fiber strands and filaments (also referred to as monofilaments) and multi-fiber strands and filaments.

If a scaffold to be coated is a fiber-based structure, coatings may be applied, for example, to individual strands prior to forming the scaffold or applied to the scaffold after the formation thereof. If the scaffold is a non-fiber-based structure, coatings may be applied, for example, to a solid polymer tube or sheet either before or after the removal of material using a suitable cutting technique such as mechanical or thermal cutting. Coatings may be created using any suitable method, including spraying, electrospraying, rolling, dipping, chemical vapor deposition, electrospinning and/or coextrusion, among others. In some embodiments, coatings may include additional agents, such as therapeutic agents, as detailed further below.

In various embodiments, the coating material may be a biodegradable or non-biodegradable coating material or a combination of both, typically, a biodegradable coating material that comprises one or more biodegradable polymers or a non-biodegradable coating material that comprises one or more non-biodegradable polymers. Non-limiting examples of biodegradable polymers for forming the biodegradable coating material include the biodegradable polymers listed above. Non-limiting examples of non-biodegradable polymers for forming the non-biodegradable coating material include the non-biodegradable polymers listed above.

In various embodiments, coatings are formed that comprise an elastomer. Potential benefits of such coatings include enhancement of mechanical properties. For example, coatings may be made from an elastomeric polymer that, due to its elastic nature when compressed or elongated, applies a force to scaffold that acts in favor of radial expansion, thus enhancing recoverability and/or radial stiffness, among other properties. An additional potential benefit of the elastomer may be to encapsulate the scaffold material (which may be a braid structure, among others), maintaining integrity and providing smooth, soft surfaces that minimize irritation of tissue at contact points while providing good conformability. In this regard, certain aspects of the designs described herein, including those resulting from composite structures and combinations of bioresorbable filaments and elastomeric coatings, provide properties that may not be achieved from other bioresorbable stent designs. Potential benefits include higher radial resistive force and/or chronic outward force with lower amounts of polymer, lower profile (thickness of stent wall) and/or better conformability due to spring-like structures at each fiber crossover point, thereby enabling delivery to the target location through smaller delivery systems or guide catheters and/or providing good apposition and conformability to the target location with smaller as-fabricated stent diameter. Better conformability may lead to more efficient drug delivery to the tissue based as a result of improved tissue contact. Furthermore, better conformability may facilitate manipulation of the implant post-deployment by the surgeon to a desired position. For example, when readjusting one side of the implant, the opposite side of the implant has a tendency to readjust its position unless it is well-contoured and adherent to the tissue.

Coating thickness for the elastomer coating may vary widely, with typical coating thicknesses ranging, for example, from 5 to 50 μm, among other thicknesses. Where a braided scaffold is coated, the elastomer coating may range, for example, between 30 and 150% by weight of the braided scaffold substrate.

Elastomers include thermoset and thermoplastic elastomers. The thermoset or thermoplastic elastomer beneficially has a glass transition temperature (Tg) that is lower than room temperature (25° C.) and is more beneficial when lower than 10° C. The thermoset elastomers may provide a high elongation to break with low permanent deformation under cyclic mechanical testing. Examples of elastomers include, for example, poly(glycolide-co-ε-caprolactone) (PGCL) or poly(lactide-co-ε-caprolactone) (PLCL), including poly(L-lactide-co-ε-caprolactone) and poly(D,L-lactide-co-ε-caprolactone). In certain embodiments, the PLCL may have a molar percentage of lactide ranging from 20 to 80% and a molar percentage of caprolactone ranging from 80 to 20%, more typically, a molar percentage of lactide ranging from 30 to 50% and a molar percentage of caprolactone ranging from 50 to 70%.

In certain embodiments, the biodegradable coating material is a thermoset elastomer formed from polymeric polyols including diols, triols, tetraols and/or higher alcohols. Such polymers may be crosslinked with a crosslinker that is a bi- or multi-functional small molecule or polymer. For example, crosslinks may be formed by reacting such polymers with bi- or multi-functional isocyanates, which may be in form of a small molecule or polymer.

In the event that the coating comprises a thermoset elastomer polymer, the crosslink density may be varied to yield desired mechanical properties. For example, optional chain terminators may be used in thermoset elastomeric materials such as polyester urethanes to control crosslink density. The chemical crosslink density is adjusted by using such chain terminators to control the degree of crosslinking taking place during the polyester-urethane curing. The crosslink density of the resultant elastomers depends on the concentration of chain terminators incorporated into the elastomeric network. Examples of suitable chain terminators include any suitable monofunctional compound such as monofunctional isocyanates, alcohols, amines, acyl chlorides, and sulfonyl chlorides.

In certain embodiments, the thermoset elastomer comprises a polyester polyol, diisocyanate crosslinker and an optional chain terminator. Such a thermoset elastomer may be prepared by a process that comprises the steps of: at least partially dissolving a polyester polyol in a solvent to form a solution; adding a diisocyanate crosslinker to said solution; optionally adding a chain terminator to said solution; coating said solution onto the scaffolding material; and curing said solution. Where solvent-based processing is employed, a less volatile co-solvent may be used to improve the node accumulation of thermoplastic elastomers during the coating process.

Non-limiting examples of suitable polyols for forming urethane-crosslinked elastomers include, for example, branched (3 arms or more) poly(lactic acid-co-caprolactone) (PLCL) and poly(glycolide-co-caprolactone) (PGCL) polyols. Besides branched polymers, linear polymer diols may also be used to create an elastic coating upon curing with isocyanates (e.g., hexamethylene diisocyanate) and other appropriate reagents. To reduce inflammation caused by material degradation, poly(trimethylene carbonate) (PTMC) based polyols may also be used to create an elastic coating. Various catalysts, including but not limited to, $Sn(Oct)_2$, $Zn(Oct)_2$, dibutyl tin dilaurate (DBTL), 1,4-diazabicyclo[2.2.2]octane (DABCO), and 1,8-diazabicycloundec-7-ene (DBU), may be used to facilitate the curing process.

In some embodiments, scaffolds and/or coatings may be fabricated using a shape-memory polymer that can change in size, shape, and/or conformability to mold to sinus anatomy. Non-limiting examples of shape-memory polymers include segmented polyurethanes made of oligolactide, oligocaprolactone, oligolactide-co-glycolide, oligo(trimethylene carbonate), or oligodioxanone coupled isocyanates and various chain extenders, (multi)block copolymers of lactide (glycolide) and caprolactone, dioxanone, or trimethylene carbonate, polymer blends of polylactide and polyamide elastomers.

As previously indicated, scaffolds in accordance with the present disclosure may be fiber-based or non-fiber-based. In fiber-based embodiments, polymeric materials may be first manufactured into fibers with cross-sectional dimension ranging, for example, from 10 μm to 1000 μm, more typically, 100 μm to 300 μm. Such fibers may be formed using a number of technologies including, for example, extrusion or spinning technologies.

The shape of the cross-section of the fibers may vary widely. Referring to FIG. 1A, such cross-sections include fibers having round cross-section 10, oval cross-section 12, and polygonal cross-section (e.g., triangular cross-section 14, quadrilateral cross-section 16, for instance, in the shape of a rectangle, parallelogram, trapezoid, etc., pentagonal cross-section, hexagonal cross-section 18, and so forth). Fiber cross-section may be varied by selecting a die of suitable cross-section for use during fiber manufacture.

Polymeric materials may also be formed into sheets, for example, through a suitable casting or extrusion process (e.g., solvent casting, melt casting, solvent-based extrusion, melt extrusion, etc.) The sheets may thereafter be cut into fibers (e.g., fibers having a polygonal cross-section, for instance, in the shape of a triangle or a quadrilateral such as rectangle, parallelogram, trapezoid, etc.).

The strength of the fibers may be optimized in certain embodiments, for example, by drawing at appropriate draw ratios or annealing at appropriate temperatures.

Figure 1B:
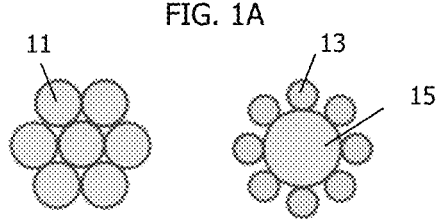
FIG. 1B schematically illustrates multi-fiber filament cross-sections, in accordance with two embodiments of the present disclosure.

Strength and/or flexibility of the fibers may also be optimized by braiding fibers of homogeneous or heterogeneous cross-section into multi-fiber strands (e.g., fish-wire-type structures). The fibers that are braided may be of the same composition or of different composition. Moreover, the fibers that are braided may be of the same diameter or different diameter. Two embodiments are shown in FIG. 1B, which illustrates (a) a cross-section of a multi-fiber strand 11 formed from strands of the same material and having the same diameter and (b) a cross-section of a multi-fiber strand 13 formed from strands of different composition and having different diameter.

Once the polymeric strands are prepared, fiber-based scaffolds may be made thereof. For example, single-fiber strands and/or multi-fiber strands of various shapes (e.g., as illustrated in FIGS. 1A-1B, among others) may be braided into a generally tubular structure. The strands that form the braids may vary widely in diameter, ranging, for example, from 10 to 1000 μm, among other possibilities. In certain embodiments, the materials forming the strands may have an elastic modulus within the range of about 1 GPa to about 10 GPa, and more preferably within the range of about 4-9 GPa.

To facilitate low-profile aspects of the present disclosure (e.g., the delivery of the scaffolds into small diameter sinus cavities), in certain beneficial embodiments, the strands used in forming scaffolds may have a diameter ranging from 100 to 500 μm, more beneficially ranging from 125 to 250 μm. The use of small diameter strands results in a scaffold with minimal wall thickness and the ability to collapse (i.e., to be crimped) within low diameter catheter delivery systems. In certain embodiments, the diameters of strands may be chosen so as to render the scaffold deliverable from a 15 French delivery catheter or smaller, from a 9 French delivery catheter or smaller, from a 6 French delivery catheter or smaller, or even from a 4 French delivery catheter or smaller.

Figure 2:
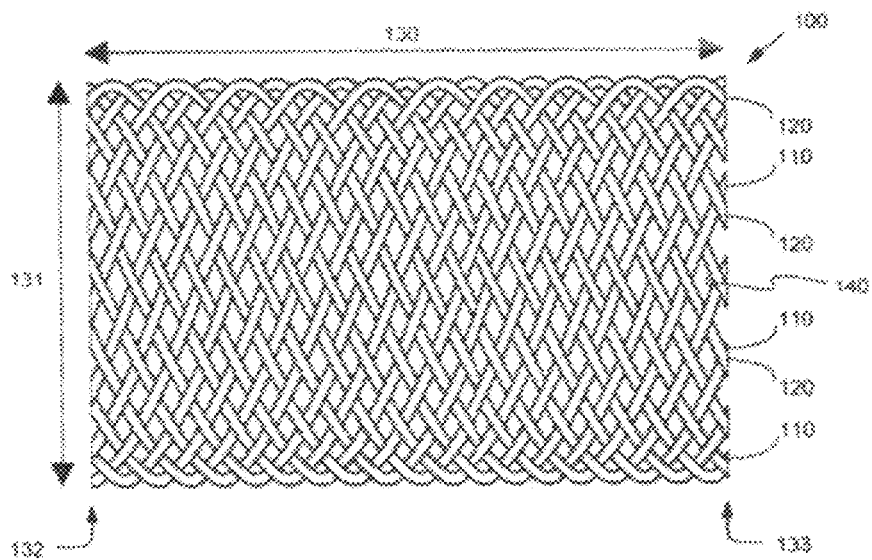
FIG. 2 is a schematic side view of a self-expanding scaffold, in accordance with an embodiment of the present disclosure.

FIG. 2 illustrates an embodiment of a braided scaffold 100, which comprises at least one strand (e.g., a single-fiber or multi-fiber strand) woven to form a substantially tubular configuration having a length 130, a width 131, and first and second ends 132, 133 along the longitudinal dimension. For example, the tubular structure may comprise two sets of strands 110 and 120, with each set extending in an opposed helical configuration along the longitudinal dimension of the scaffold. In certain embodiments, the number of helical strands forming the scaffold may range, for example, from 8 to 48 strands, among other possibilities. The sets of strands 110 and 120 cross each other at a braid angle 140. The braid angle 140 may range, for example, from about 30 degrees or less to about 150 degrees or more, among other values, for example, ranging anywhere from 30 degrees to 40 degrees to 50 degrees to 60 degrees to 70 degrees to 80 degrees to 90 degrees to 100 degrees to 110 degrees to 120 degrees to 130 degrees to 140 degrees to 150 degrees (i.e., ranging between any two of the preceding numerical values). Strands may be woven together using a variety of methods known in the art including, for example, various 1×1, 1×2 and 2×2 designs and may be woven using particular known weave patterns such as Regular pattern "1 wire, 2-over/2-under", Diamond half load pattern "1 wire, 1-over/1-under", or Diamond pattern "2 wire, 1-over/1-under".

Various factors contribute to the radial strength of scaffold 100, including the diameter(s) of the strands, the braid angle 140, the strand material(s), and the number of strands used, among others.

Figure 3A:
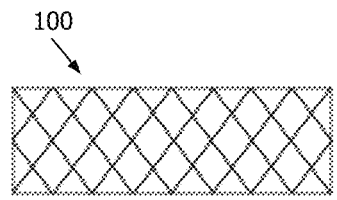
FIG. 3A is a schematic side view of a self-expanding scaffold having uniform braid angles, in accordance with an embodiment of the present disclosure.
Figure 3B:
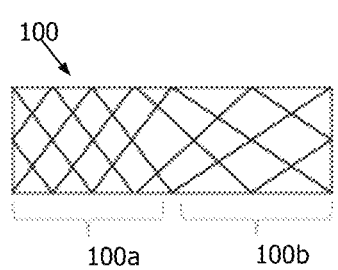
FIG. 3B is a schematic side view of a self-expanding scaffold having variable braid angles, in accordance with an embodiment of the present disclosure.

Strands may cross each other at a braid angle which is constant or which may change around the circumference of the scaffold and/or along the longitudinal dimension of the scaffold. FIG. 3A shows an embodiment in which a scaffold 100 has strands of constant braid angle, whereas FIG. 3B shows an embodiment in which a scaffold 100 has strands of variable braid angle. In the particular embodiment of FIG. 3B, a first region 100a having strands of a first braid angle transitions into a second region 100b having strands of a second braid angle that is less than the first braid angle. Various filament braiding patterns may be used to manufacture such constructs.

Potential attributes of a design with variable braid angles include one or more of the following, among others: (1) it allows for the orientation of segments with specific density for preferential therapeutic agent delivery; (2) it allows for tailored radial force depending on scaffold location; and (3) it may be used to provide a tapered tubular design that is useful for non-cylindrical anatomy.

In general, the shape and diameter of a scaffold in accordance with the present disclosure may change along the length of the device. In certain embodiments, in a cylindrical design the diameter at the ends of the device may be larger than the diameter at the midpoint (e.g. a dumbbell or hourglass shape). For instance, the diameter at the ends of the device may be 1.5 times or more, even 2 times or more, than the diameter at the midpoint. As another example, the shape of the device may be triangular at one end and hexagonal at the other end.

Radial stiffness for braided scaffolds may be tailored by partially or completely locking various strand cross-over points (also referred to as "nodes"). Nodes may be partially or completely locked, for example, by welding the strands at cross-over points, for instance, using heat (e.g., using a suitable laser such as a pico or femto laser), by using a suitable adhesive, by wrapping crossover points with a suitable filament, or by coating cross-over points with a suitable material that holds the filaments together, among other possible techniques. In some embodiments, elastomers may be coated onto the braids, for example, using procedures such as those described in U.S. Pat. Nos. 8,137,396, 8,540,765, and 8,992,601, the disclosures of which are hereby incorporated by reference.

Figure 4:
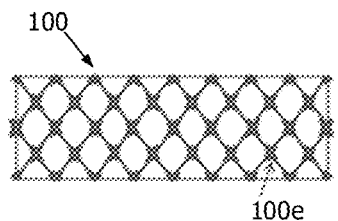
FIG. 4 is a schematic side view of a self-expanding scaffold having an elastomer coating, in accordance with an embodiment of the present disclosure.

Underlying braids, either with or without previously locked nodes, may be subject to elastomer coating. One embodiment is illustrated in FIG. 4, which shows a braided scaffold 100 that is completely coated with an elastomer 100e. Varying the node accumulation of the coated elastomer may optimize both radial resistive force (RRF) and chronic outward force (COF) for this sinus cavity.

Figure 5:
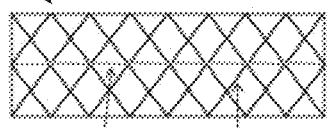
FIG. 5 is a schematic side view of a self-expanding scaffold having an elastic cross-fiber, in accordance with an embodiment of the present disclosure.

In alternative embodiments, scaffolds may be provided in which the nodes of the braided structure are connected using an elastic member such as an elastic filament or strand. One such embodiment is illustrated in FIG. 5, which shows a scaffold 100 in which an elastic strand 111 is attached to the braid 110 at various points along the length of the braid 110. In these embodiments, the braid itself provides the framework to support the sinus cavity, while the elastic filament or strand 111 is provided to enhance scaffold recovery during deployment. The elastic filament or strand 111 may be, for example, woven into the scaffold 100 during braiding process or introduced to the scaffold 100 after it is formed. In the latter case, the braid 110 forming the scaffold 100 may be made from softer, non-elastic materials that conform to sinus walls and have desired degradation profiles. The number of elastic filaments or strands 111 used in a given scaffold 100 may be tailored to afford appropriate recovery and radial stiffness.

A conformable scaffold is desirable in various embodiments, as it may be used to improve apposition to contacted tissues, reduce damage to the contacted tissue and, where a therapeutic agent is delivered, also increase the therapeutic agent delivery efficacy due to increased tissue contact.

Various strategies may be employed to increase conformability of the braided scaffolds. For example, in some embodiments, some or all of the nodes of the braids may be partially locked or not locked at all to allow at least some filaments at least some freedom to slide over one another. In a constrained space, scaffolds with freely movable filaments will have a tendency to better adapt to the geometry of the surrounding environment.

Figure 6A:
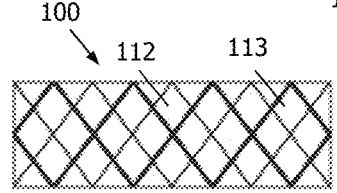
FIG. 6A is a schematic side view of a self-expanding scaffold having filaments of different stiffness, in accordance with an embodiment of the present disclosure.

Alternatively or in addition, scaffolds may be braided from filaments of different stiffness (e.g., having a combination of higher and lower stiffness). The stiffness of a given strand is determined, for example, by its inherent material properties, by its processing conditions, and by its dimension. One embodiment of this type of scaffold is schematically illustrated in FIG. 6A in which a scaffold 100 is shown that is formed from strands of higher stiffness 112 and strands of lower stiffness 113. In one specific embodiment, the strands of higher stiffness 112 may have an elastic modulus higher than 3 GPa and filament diameter greater than 100 μm, while the strands of lower stiffness 113 may have an elastic modulus lower than 3 GPa and filament diameter less than 200 μm. Filaments with lower stiffness may provide a weaker point in the scaffold to allow for deformation to comply with the sinus cavities, whereas filaments with higher stiffness may maintain mechanical integrity.

Figure 6B:
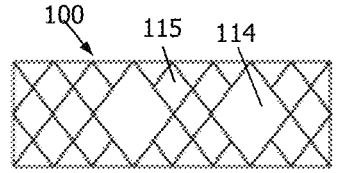
FIG. 6B is a schematic side view of a self-expanding scaffold having removed filament segments, in accordance with an embodiment of the present disclosure.

Conformability may also be improved by removing some of the strands from within the braided structure. One embodiment of this type of scaffold is schematically illustrated in FIG. 6B in which a scaffold 100 is shown in which cells of varying size are formed. In particular, a scaffold containing larger diamond shaped cells 114 and smaller diamond shaped cells 115 are shown. In some embodiments, a severed strand may be partially or completely locked at a cross-over point nearest to the severed tip of the strand.

Figure 7:
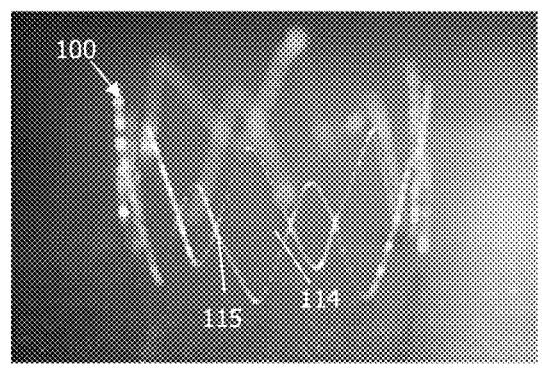
FIG. 7 is a photograph of a self-expanding scaffold having unequal cell sizes, in accordance with an embodiment of the present disclosure.

In related embodiments, different sized cells are created during the course of the braiding process, for example, through selection of a suitable braiding pattern. One embodiment of a scaffold 100 having larger braided cells 114 and smaller braided cells 115 is shown in FIG. 7.

Where cells of differing sizes are formed, the larger cells may have an area ranging from 1.1 times to 10 or more times an area of the smaller cells.

Potential advantages of scaffolds having a combination of larger and smaller cells is that the larger cells may provide flexibility (e.g. for ease of crimping and better conformability), whereas the smaller cells may maintain mechanical integrity.

Another route to create conformable scaffolds is to braid the scaffolds using a rigid rubber material such as carbon fiber reinforced silicone, poly(acrylonitrile butadiene), and poly(styrene butadiene) rubbers, among others. This results in completely elastic braids.

In some embodiments, a coating layer may be formed over all or a part of the scaffold structure. By employing a relatively non-elastic material for the coating layer (e.g., one formed using a relatively stiff polymer such as D,L-PLGA), the stiffness of the scaffold may be improved. Moreover, where the implant is formed using braids that are inherently elastic and where the coating layer is a degradable layer, upon degradation of the degradable layer, the scaffold strands will have increased conformability.

Figure 6C:
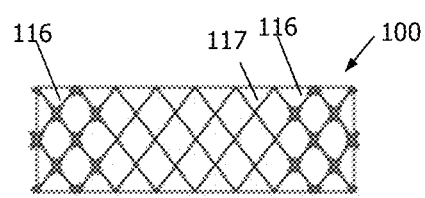
FIG. 6C is a schematic side view of a self-expanding scaffold having coated ends, in accordance with an embodiment of the present disclosure.
Figure 6D:
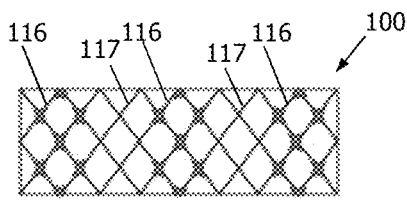
FIG. 6D is a schematic side view of a self-expanding scaffold having alternating coated and uncoated sections, in accordance with an embodiment of the present disclosure.

Furthermore, the coating layer may be applied in a pattern in order to tailor the conformability of the braided scaffolds. As one specific example, FIG. 6C shows an embodiment of a scaffold 100 where coated regions 116 are provided at each end of the scaffold 100 while an uncoated region 117 is provided at the center of the scaffold 100. Such a design may be used to provide ends having enhanced stiffness, which may allow the device to be better anchored into the sinus cavities. Moreover, leaving the middle region of the scaffold 100 uncoated may enhance the ability of the stent to comply with the shape of the sinus cavities at the time of implantation. As another specific example, FIG. 6D shows an embodiment of a scaffold 100 where coated regions 116 and uncoated regions 117 are provided in an alternating pattern. The presence of uncoated regions 117 provides regions of increased flexibility along the length of the scaffold, which may provide enhanced conformability to irregular surfaces such as those associated with the sinus cavities.

Regions of coated and uncoated material may be provided using various techniques. For instance, in some embodiments, a mask may be used in a spray coating process to create specific patterns of coated and uncoated regions.

By masking a part of the tubular braids longitudinally during spray coating, a U-shaped coating region (when viewed longitudinally) may be created. In these scaffolds, the coated region is relatively stiff while the uncoated region is relatively soft. The coated region would provide scaffold recoverability after deployment into sinus cavities. On the other hand, the soft uncoated region may readily deform to adapt the irregular surface of sinus cavities, affording optimized conformability. In one particular embodiment, such a scaffold may be useful to maintain patency in select cases where an opening is made between the left and right paranasal sinuses.

In some embodiments, the scaffold may be cut longitudinally, allowing the circumference of the scaffold to be readily resized to match the geometry of sinus cavities upon deployment, which may provide better compliance and conformability.

Figure 8:
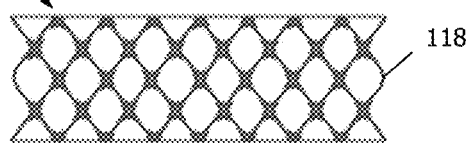
FIG. 8 is a schematic side view of a self-expanding scaffold having fold-back ends, in accordance with an embodiment of the present disclosure.

To reduce potential tissue irritation or patient discomfort caused by sharp scaffold edges, the scaffold edges may be coated and/or braided scaffolds may be made in which the end filaments are turned back toward the center of the scaffold. For instance, the filament ends may be woven back into the scaffold structure and bonded, for example, at the nodes. Bonding may be conducted using the techniques described hereinabove for bonding filaments at the nodes (e.g., by welding, application of a suitable adhesive, application of an elastomeric coating, etc.). A scaffold 100 of this type is schematically illustrated in FIG. 8 in which the end filaments 118 are turned back toward the center of the scaffold 100.

To the extent that difficulty may be encountered when short scaffolds are braided on large diameter mandrels (i.e., when forming scaffolds with large diameter to length ratios), zig-zag strands, including single- and multi-fiber strands, may be fabricated prior to braiding. The zig-zag strands may then be wound or looped around the mandrels, preferably in braided pattern. The ends of the filaments may then be attached, for example, using the techniques described hereinabove for bonding filaments at the nodes (e.g., by welding, application of a suitable adhesive, application of an elastomeric coating, etc.) to complete the braided structure. The size and shape of the final scaffold may be controlled by the turn angle, orientation and strut length of the zig-zag filaments. Such a braid may also have fold-back ends as depicted above.

In certain embodiments, it is beneficial to provide sinus scaffolds with a capability of being readily removed if it is desired to do so. In the case of a relatively soft braided scaffold, a tool with one or more hooks at the end may be used to capture a distal end of the implanted scaffold. Alternatively, the device could be removed by standard surgical instruments available to ENT surgeons. Then, the braid may be inverted by pulling the end, and thus the exterior surface, into the lumen. In this way, the scaffold may be removed by peeling off the sinus wall, reducing additional abrasion, irritation, and damage to sinus tissue.

Other scaffolds are based on non-braided structures or hybrid braided/non-braided structures.

Figure 9:
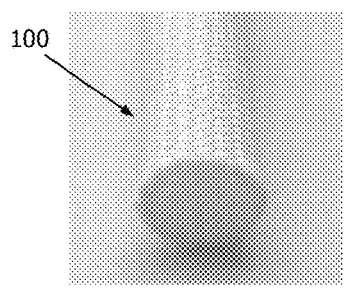
FIG. 9 is an illustration of a knitted scaffold, in accordance with an embodiment of the present disclosure.

For instance, in various embodiments, scaffolds are provided which are formed from woven or knitted strands. A scaffold 100 in the form of a knitted tube is illustrated in FIG. 9. Such a woven or knitted scaffold may provide the mechanical properties necessary to provide a stenting function, while also having enhanced compliance and conformability (as well as facilitating therapeutic agent delivery in some embodiments). In addition, in the case of a knitted structure, one end of a single strand used to form the tube may be pulled to unravel the stent, enabling removal of the scaffold, in some embodiments.

Figure 10:
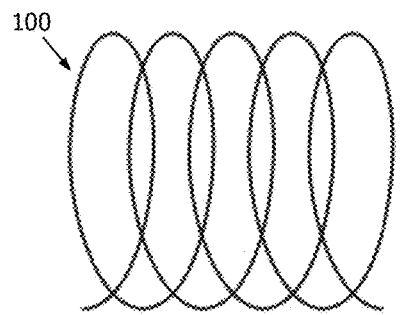
FIG. 10 is a schematic perspective view of a spiral-shaped self-expanding scaffold, in accordance with an embodiment of the present disclosure.

In various other embodiments, scaffolds may be in a spiral (e.g., helical) form. In some of these embodiments, a spiral form may be formed from a single strand (e.g., a single- or multi-fiber strand). An example of such a scaffold 100 is schematically illustrated in FIG. 10.

Figure 11A:
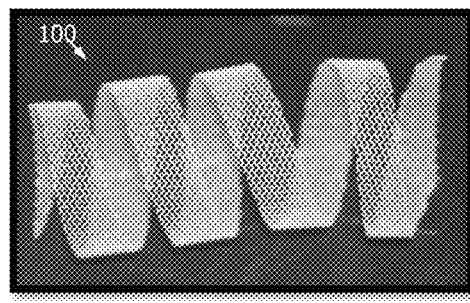
FIG. 11A is a photograph of a spiral-shaped self-expanding scaffold formed from a braided tubular scaffold, in accordance with an embodiment of the present disclosure.
Figure 11B:
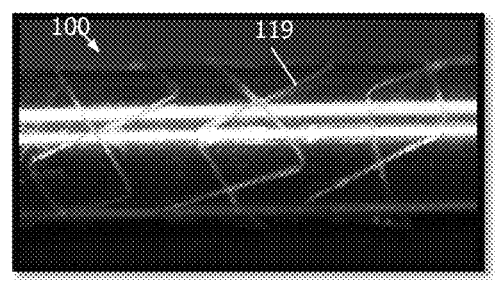
FIG. 11B is a photograph of a spiral-shaped self-expanding scaffold formed from a two-carrier braid, in accordance with an embodiment of the present disclosure.

In other of these embodiments, a spiral form may be formed from multi-stranded constructs. Examples of multi-stranded constructs include, for example, substantially two-dimensional structures (e.g., ribbon-shaped structures) which can be shaped into a spiral form. Two embodiments of spiral-shaped scaffolds of this type are shown in FIG. 11A and FIG. 11B. In the embodiment shown in FIG. 11A, a spiral shaped scaffold 100 is formed from a pre-existing tubular structure such as, for example, braided tubular structure (e.g., one of those previously described), which is subsequently cut into a spiral. In the embodiment shown in FIG. 11B, a scaffold 100 is formed by fashioning a previously formed substantially two-dimensional braid pattern 119 into a spiral structure, for example, by placing the substantially two-dimensional braid pattern on a mandrel and annealing it for a time and at a temperature suitable to form the two-dimensional braid pattern into a spiral shape. Examples of such braid patterns include multi-carrier braid patterns, such as a 2-carrier (shown in FIG. 11B), 3-carrier, 4-carrier, etc. braid pattern.

Figure 12A:
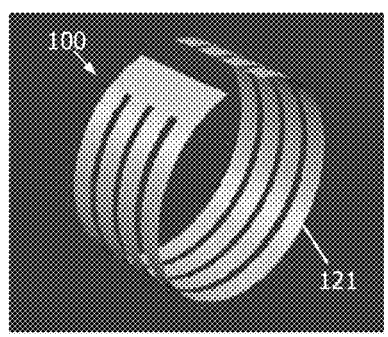
FIG. 12A is a schematic perspective view of a self-expanding scaffold having solid strut hoops, in accordance with an embodiment of the present disclosure.
Figure 12B:
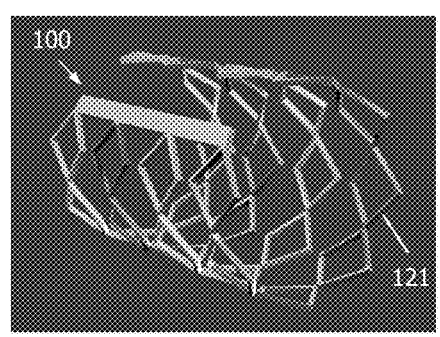
FIG. 12B is a schematic perspective view of a self-expanding scaffold having strut hoops in the form of a two carrier braid design, in accordance with an embodiment of the present disclosure.

It is noted that scaffolds analogous to the various braided structures described herein may be in the form of a unitary polymeric structure. The use of a unitary polymeric structure may provide a reduced profile when compared to the use of fiber-based techniques, which yield a minimum profile that is the sum of the widths of overlapping strands. One embodiment of such a structure is shown in FIG. 15, in which a scaffold 100 is illustrated and is characterized by a regular, repeating pattern such as a lattice structure. When the scaffold 100 is a unitary polymeric structure, it may be fabricated using a variety of suitable techniques, such as by mechanical cutting or laser cutting a pattern into a solid polymer tube or a solid polymer ribbon In various other embodiments, the scaffold may be in the form of an open cylinder. For example, as shown in FIGS. 12A and 12B, the scaffold 100 may be formed form a series of individual hoops 121 which are axially aligned with one another and connected at one end. In the embodiment shown in FIG. 12A, individual hoops 121 are solid hoops (e.g., in the form of a ribbon). In the embodiment shown in FIG. 12B, individual hoops 121 comprise cells, in particular, diamond-shaped cells analogous to those formed with a 2-carrier braid. Benefits of these designs may include one or more of the following, among others: the hoops are straightforward to crimp to size; and upon delivery, the scaffold unfurls to an expanded diameter. Because each hoop is allowed to expand to different widths, the scaffold may be more conformal in variable sized spaces.

In still other embodiments, a scaffold 100 may be in the form of a polymeric tube such as that shown in FIG. 13. Such a device is beneficial, for example, in that it may conform to the sinus wall 200 and, optionally release one or more therapeutic agents. The tube may utilize materials such as the scaffold materials described above, among others, and include thermally-forged PCL, or PLCL with high caprolactone content, among many other possible materials.

In a related device design, a tubular conformal scaffold like that shown in FIG. 13 may be attached to a crimpable three-dimensional support structure which may assist the tubular scaffold in expansion and support of the sinus. A specific example of such a device is shown in FIG. 14, which shows the tubular scaffold 110 attached to a crimpable three-dimensional structure 122. The structure 122 is crimpable to allow for minimally invasive delivery. Structures 122 may be provided at the ends of the tubular scaffold 110, and if desired, at one or more points along a length of the tubular scaffold 110. Examples of materials suitable for forming the crimpable three-dimensional structure include degradable or non-degradable elastomeric materials that can be compressed and recover from that deformation. In other embodiments, braided stent structures like those discussed hereinabove may be used as crimpable three-dimensional structures.

Supplemental agents such as therapeutic agents and inactive release-controlling agents may be integrated into the various devices described herein.

Examples of therapeutic agents are any suitable agents having desired biological effects, including small molecule agents, biologics, cells, including stem cells, gene therapies and RNAi, among others. Specific examples of therapeutic agents include: analgesic agents including simple analgesics such as aspirin and paracetamol, non-steroidal anti-inflammatory drugs such as ibuprofen, diclofenac, naproxen, celecoxib, ketoprofen, piroxicam and sulindac, and opioids such as codeine tramadol, dextropropoxyphe, paracetamol, morphine, oxycodone and pethidine hydrochloride; anesthetic agents such as lidocaine, bupivacaine, and ropivacaine; statins such as atorvastatin, cerivastatin, fluvastatin, lovastatin, mevastatin, pitavastatin, pravastatin, rosuvastatin, and simvastatin; steroidal anti-inflammatory drugs such as glucocorticoids, mometasone furoate, beclomethasone dipropionate, budesonide, ciclesonide, flunisolide, fluticasone furoate, fluticasone propionate, dexamethesone, cortisone, prednisone, methylprednisolone, triamcinolone acetonide, betamethasone, dexamethasone, prednisolone, corticosterone, estrogen, sulfasalazine, rosiglitazone, mycophenolic acid, and mesalamine; antihistamines including $H_1$-receptor antagonists such as diphenhydramine, loratadine, fexofenadine, cyproheptadine, promethazine, desloratadine, chlorpheniramine, hydroxyzine and pyrilamine and $H_2$-receptor antagonists such as cimetidine, famotidine, lafutidine, nizatidine, ranitidine, roxatidine and tiotidine; antimicrobial agents such as mupirocin, gentamycin and tobramycin; antibiotic agents such as penicillin, cefoxitin, oxacillin and tobramycin; endostatin, angiostatin and thymidine kinase inhibitors, and its analogs or derivatives; antileukotriene agents (e.g. montelukast, zafirlukast, zileuton, etc.); antifungal agents; and probiotics, among many others.

Further examples of therapeutic agents may be selected from anti-thrombogenic agents such as heparin, heparin derivatives, urokinase, and PPack (dextrophenylalanine proline arginine chloromethylketone), enoxaparin, hirudin; anti-proliferative agents such as angiopeptin, or monoclonal antibodies capable of blocking smooth muscle cell proliferation, acetylsalicylic acid, paclitaxel, sirolimus, tacrolimus, everolimus, zotarolimus, vincristine, sprycel, amlodipine and doxazosin; immunosuppressants such as sirolimus, tacrolimus, everolimus, zotarolimus, and dexamethasone; antineoplastic/antiproliferative/anti-mitotic agents such as paclitaxel, 5-fluorouracil, cisplatin, vinblastine, cladribine, vincristine, epothilones, methotrexate, azathioprine, halofuginone, adriamycin, actinomycin and mutamycin; anti-coagulants such as D-Phe-Pro-Arg chloromethyl ketone, an RGD peptide-containing compound, heparin, antithrombin compounds, platelet receptor antagonists, antithrombin antibodies, anti-platelet receptor antibodies, aspirin (aspirin is also classified as an analgesic, antipyretic and anti-inflammatory drug), dipyridamole, hirudin, prostaglandin inhibitors, platelet inhibitors and antiplatelet agents such as trapidil or liprostin, tick antiplatelet peptides; DNA demethylating drugs such as 5-azacytidine, which is also categorized as a RNA or DNA metabolite that inhibit cell growth and induce apoptosis in certain cancer cells; vascular cell growth promotors such as growth factors, Vascular Endothelial Growth Factors (VEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; angiogenic substances, such as acidic and basic fibrobrast growth factors, estrogen including estradiol (E2), estriol (E3) and 17-Beta Estradiol; drugs for heart failure, such as digoxin, beta-blockers, angiotensin-converting enzyme (ACE) inhibitors including captopril and enalopril, statins and related compounds; macrolides such as sirolimus and everolimus; and agents that have a primary mechanism of action of inhibiting extracellular matrix remodeling, and a secondary mechanism of action of inhibiting cell proliferation such as 5-fluorouracil, doxycyclin, carvedilol, curcumin, and tranilast.

Other therapeutic agents include bacteria or other microflora that may be beneficial to re-establishing a healthy microbiome in the nasal cavity and sinuses as well as agents or nutrients that may promote a healthy microbiome.

Inactive release-controlling agents may also be included to enhance control over the therapeutic agent release kinetics. Examples of inactive release-controlling agents include soluble polymers such as polyethylene glycol (PEG) (also known as polyethylene oxide, PEO), PEG-vinyl alcohol copolymers, polyacrylate and polymethacrylate esters containing cationic and anionic functionality, polyvinyl pyrrolidone, and dextran, as well as small molecule additives such as cyclodextrin or citrate esters such as acetyltributyl citrate (ATBC) or acetyltriethyl citrate (ATEC).

In embodiments where the scaffold delivers one or more therapeutic agents at the site of implantation, the therapeutic agent(s) may be provided in the device for delivery therefrom in a number of ways.

For example, the therapeutic agent may be directly embedded within a polymeric construct (e.g., filaments, sheets, solid tubes, etc.) that is subsequently used to form a generally tubular scaffold as described herein. In one embodiment, therapeutic agent and polymer(s) are dissolved in an appropriate solvent to make a homogenous solution or a suspension, or therapeutic agent and polymer(s) are heated to form a polymer melt containing the therapeutic agent. The solution, suspension or melt is then subjected to suitable solvent-based or melt-based processing such as extrusion, wet spinning, dry spinning, melt spinning, electrospinning or other process to afford therapeutic-agent-loaded polymeric constructs (e.g., filaments, sheets, tubes, etc.) with embedded therapeutic agents. In some embodiments, a polymeric region that does not contain a therapeutic agent (e.g., a polymer core) is coextruded with a therapeutic-agent-loaded polymeric coating to form therapeutic-agent-loaded polymeric constructs.

In some embodiments, therapeutic-agent-loaded polymeric constructs may then be subsequently processed into additional forms that are subsequently used to form generally tubular scaffolds as described herein. As a specific example, a solvent-cast therapeutic-agent-loaded polymeric construct in the form of a sheet may be made by controlled evaporation of a solution of a therapeutic agent and one or more carrier polymers. After removal of the solvent(s), the therapeutic-agent-loaded polymer sheet may be laser cut into therapeutic-agent-loaded polymeric constructs in the form of flat filaments for braid manufacture.

In some embodiments, the therapeutic agent may be applied onto a pre-formed construct (e.g., a filament, a sheet, or a tube, including a pre-formed device scaffold) in the presence or absence of a carrier material (e.g., a polymeric coating material such as those described above) using a suitable application technique such as spray-coating, dip-coating, rolling or vapor deposition, among others. The therapeutic agent releasing profile may be tailored, for example, by the thickness of the coating layer, by the addition of inactive ingredients and, where a polymer is provided as a carrier, changing the carrier polymer (e.g. changing the composition and/or molecular weight of the polymer) and/or the therapeutic-agent-to-polymer ratio.

A topcoat of a therapeutic-agent-free polymer layer may also be employed to regulate the delivery of the therapeutic agent from the device into bodily tissue. In embodiments pertaining non-biodegradable topcoats, the topcoat may act as a diffusion barrier such that the rate of delivery of the therapeutic agent(s) is limited by the rate of its diffusion through the topcoat. In some embodiments pertaining to biodegradable topcoats, the topcoat may also act as a diffusion barrier such that the rate of delivery of the therapeutic agent(s) is limited by the rate of its diffusion through the topcoat. In other embodiments pertaining to biodegradable topcoats, the therapeutic agent(s) cannot diffuse through the topcoat, such that delivery thereof is simply delayed until the degradation of the topcoat is complete.

Electrospinning provides another potential method to introduce therapeutic agent onto a pre-formed construct. In one embodiment, a fiber-based or non-fiber-based scaffold may be covered by an electrospun fiber mesh, such as a core-sheath fiber mesh. During electrospinning, the therapeutic agent may be either dissolved or suspended in a core polymer solution. The therapeutic agent release profiles may be tuned by adjusting the therapeutic agent loading, the particulate size of the therapeutic agent (where a suspension is employed), the types of polymers used to form the core and sheath, respectively, as well as the thickness of the sheath.

In other embodiments, core-sheath fibers are first fabricated through coaxial electrospinning of a core polymer solution or suspension with therapeutic agent and a sheath polymer solution. The therapeutic-agent-loaded fibers may be further braided onto a multi-fiber strand that will be used to manufacture devices. For example, a fish-wire-shaped composite strand may be formed and thereafter fabricated into a braided scaffold as described previously. In these designs, the therapeutic agent release may be dictated by the electrospun fibers.

In some embodiments, biologically active agents such as proteins and/or polysaccharides may be incorporated into electrospun fibers.

In some embodiments, the devices described herein can be used in conjunction with sinuplasty. For example, scaffolds such as those described herein can be deployed into the sinus cavities with the assistance of an expandable device such as an expandable frame (e.g., an expandable wire frame) or a balloon, among other possibilities. In such embodiments, a scaffold in accordance with the present disclosure may be positioned on, in, under, proximal to, or distal to the expandable device, either at a manufacturing site or by a healthcare professional at the time of delivery. The expandable device may be a drug-eluting device (e.g., via a drug-containing coating disposed on the expandable device) or a non-drug-eluting device. Examples of therapeutic agents which may be released by a drug-eluting device are described above.

Thus, in the case of a balloon, the balloon may be coated or uncoated, and a scaffold in accordance with the present disclosure may be positioned on, in, under, proximal to, or distal to a balloon catheter suitable for sinuplasty, either at a manufacturing site or by a healthcare professional at the time of delivery. The catheter may include an inflatable balloon assembly disposed at or near a distal end of a catheter shaft that comprises an inflation lumen for the balloon. In an uninflated state, the balloon assembly does not significantly increase the overall width of the distal end of the catheter. This allows the distal portion of the catheter to be inserted into a patient and guided to a desired treatment site in the patient's sinuses. Once at the treatment site, the balloon assembly is inflated to position the scaffold against the sinus wall proximate to the treatment site. The balloon assembly can include any number of individual balloons in a number of configurations, depending upon the treatment site. Additionally, the sinuplasty may be completed before delivery of the scaffold, after delivery of the scaffold, simultaneously with delivery of the scaffold, or any combination of perioperative procedural sequences.

In some embodiments, the devices described herein can be used as an adjunctive therapy. For instance, scaffolds such as those described herein can be deployed into the sinus cavities using a therapeutic-agent-eluting delivery device such as, for example, a therapeutic-agent-eluting balloon. Alternatively, scaffolds can be deployed into the sinus cavities, after the cavities have been treated with a therapeutic-agent-releasing spray such as a hydrogel spray, or irrigation liquid that contains one of the therapeutic agents previously described in this disclosure.

The scaffolds of the present disclosure may be radiopaque such that they are visible using conventional fluoroscopic techniques. In one embodiment, radiopaque additives are included within the polymer material of the scaffold and/or its coating, where present. Examples of suitable radiopaque additives include particles comprising iodine, bromine, barium sulfate, platinum, iridium, tantalum, and/or palladium. In another embodiment, the radiopaque groups, such as iodine, are introduced onto the polymer backbone. In yet another embodiment, one or more biostable or biodegradable radiopaque markers, for example, comprising platinum, iridium, tantalum, and/or palladium may be produced in the form of a tube, coil, wire, sphere, or disk, which is then placed at the ends of the scaffold or at other predetermined locations thereon.

To facilitate delivery, the scaffold may be loaded into a delivery catheter just prior to being implanted into a patient. Loading the scaffold in close temporal proximity to implantation avoids the possibility that the polymer of the scaffold will relax during shipping, storage, and the like within the delivery catheter. One aspect of the disclosure thus includes a method of delivering a scaffold of the disclosure that comprises a step of loading the scaffold into a delivery catheter within a short period of time, for example, within one hour, before implantation into a body lumen. It should be noted, however, that it is not required that the scaffolds of the present disclosure are loaded into delivery catheters just prior to being implanted.

In certain embodiments, scaffolds may be provided which are suitable for implantation into the vacated space that is formed during an ethmoidectomy, among other uses (e.g., using a 6 mm catheter, among other devices). Such scaffolds may range, for instance, from 10 to 30 mm in diameter, more particularly, from 15 to 20 mm in diameter, among other possible values. Such scaffolds may range, for instance, from 5 to 20 mm in length, more particularly, from 8 to 12 mm in length, among other possible values. In certain beneficial embodiments, the scaffolds comprises a braided scaffold material, which may comprise, for example, from 8 to 64 braiding strands, more particularly, from 16 to 32 braiding strands, among other possible values. In certain beneficial embodiments, braid angle may vary, for instance, from 30 to 150 degrees, more particularly, from 60 to 130 degrees, among other possible values. In certain beneficial embodiments, diameter of the strands that form the braids may vary from 50 to 500 µm, more particularly, from 150 to 300 µm, among other possible values. In certain beneficial embodiments, scaffold mass may range, for instance, from 1 to 20 mg/mm of length, more particularly, from 2 to 10 mg/mm, among other possible values. In certain beneficial embodiments, scaffolds have a % diameter recovery of at least 85% after being compressed to a diameter of that is 30% of the unconstrained diameter for 10 minutes. Where drug is released, in non-refractory patients the drug may be released over a period of 3 to 6 weeks, among other values, whereas in refractory patients the drug may be released over a period of 8 to 26 weeks, among other values In certain embodiments, scaffolds may be provided which are suitable for implantation into the middle meatus space, among other uses (e.g., using a 3-4 mm delivery catheter, among other possible devices). Such scaffolds may range, for instance, from 5 to 20 mm in diameter, more particularly, from 10 to 15 mm in diameter, among other possible values. Such scaffolds may range, for instance, from 5 to 20 mm in length, more particularly, from 8 to 12 mm in length, among other possible values. In certain beneficial embodiments, the scaffolds comprises a braided scaffold material, which may comprise, for example, from 8 to 64 braiding strands, more particularly, from 16 to 32 braiding strands, among other possible values. In certain beneficial embodiments, braid angle may vary, for instance, from 30 to 150 degrees, more particularly, from 60 to 130 degrees, among other possible values. In certain beneficial embodiments, diameter of the strands that form the braids may vary from 100 to 500 µm, more particularly, from 150 to 300 µm, among other possible values. In certain beneficial embodiments, scaffold mass may range, for instance, from 1 to 20 mg/mm of length, more particularly, from 2 to 10mg/mm of length, among other possible values. In certain beneficial embodiments, scaffolds have a % diameter recovery of at least 85% after being compressed to a diameter of that is 30% of the unconstrained diameter for 10 minutes. In certain beneficial embodiments, scaffolds have a RRF ranging from 30 to 500 mmHg upon being measured in an MSI radial force tester at a diameter less than the manufactured diameter, among other possible values. In certain beneficial embodiments, scaffolds have an acute COF ranging from 5 to 100 mmHg upon being measured in an MSI radial force tester at a diameter less than the manufactured diameter, among other possible values. Where drug is released, it may be released over a period of 8 to 26 weeks, among other values.

In certain embodiments, scaffolds may be provided which are suitable for implantation into the sinus ostia, among other uses (frontal, maxillary, or sphenoid) or the frontal sinus recess (e.g., using a 3-4 mm delivery catheter, among other possible devices). Such scaffolds may range, for instance, from 4 to 20 mm in diameter, more particularly, from 6 to 10 mm in diameter, among other possible values. Such scaffolds may range, for instance, from 5 to 20 mm in length, more particularly, from 6 to 12 mm in length, among other possible values. In certain beneficial embodiments, the scaffolds comprise a braided scaffold material, which may comprise, for example, from 8 to 64 braiding strands, more particularly, from 16 to 32 braiding strands, among other possible values. In certain beneficial embodiments, braid angle may vary, for instance, from 30 to 150 degrees, more particularly, from 60 to 130 degrees, among other possible values. In certain beneficial embodiments, diameter of the strands that form the braids may vary from 100 to 500 µm, more particularly, from 150 to 300 µm, among other possible values. In certain beneficial embodiments, scaffold mass may range, for instance, from 1 to 20 mg/mm of length, more particularly, from 2 to 10mg/mm, among other possible values. In certain beneficial embodiments, scaffolds have a % diameter recovery of at least 85% after being compressed to a diameter of that is 30% of the unconstrained diameter for 10 minutes. In certain beneficial embodiments, scaffolds have a RRF ranging from 30 to 500 mmHg upon being measured in an MSI radial force tester at a diameter less than the manufactured diameter, among other possible values. In certain beneficial embodiments, scaffolds have an acute COF ranging from 5 to 100 mmHg upon being measured in an MSI radial force tester at a diameter less than the manufactured diameter, among other possible values. Where drug is released, it may be released over a period of 6 to 26 weeks, among other values.

In some aspects, the scaffolds described herein may be provided in a kit that includes (a) one or more scaffolds, (b) delivery catheters, and (c) optional loading aids (e.g., crimping mechanisms), among other components.

EXAMPLE 1

Uniformly braided scaffolds (see, e.g. FIG. 3A) were first manufactured using a PLGA(85:15) copolymer by spooling fiber spun monofilaments onto individual bobbins. Each bobbin was placed on a braiding machine, strung through rollers and eyelets and wrapped around a mandrel of desired OD (e.g. 7, 8, or 10 mm). The braiding tension of the machine was set as appropriate for the size of the monofilament. The pix/inch was set to obtain a braid angle with optimal properties including radial strength. The braid pattern was selected and the monofilaments were braided off the spool onto the mandrel by the braiding machine. Tie wraps were used on the end of each mandrel to keep the tension on the filaments, which can be useful for heat annealing and obtaining high modulus properties. The braided polymer was heat annealed on the mandrel, and then cut into desired lengths with a blade and removed from the mandrel.

Figure 16:
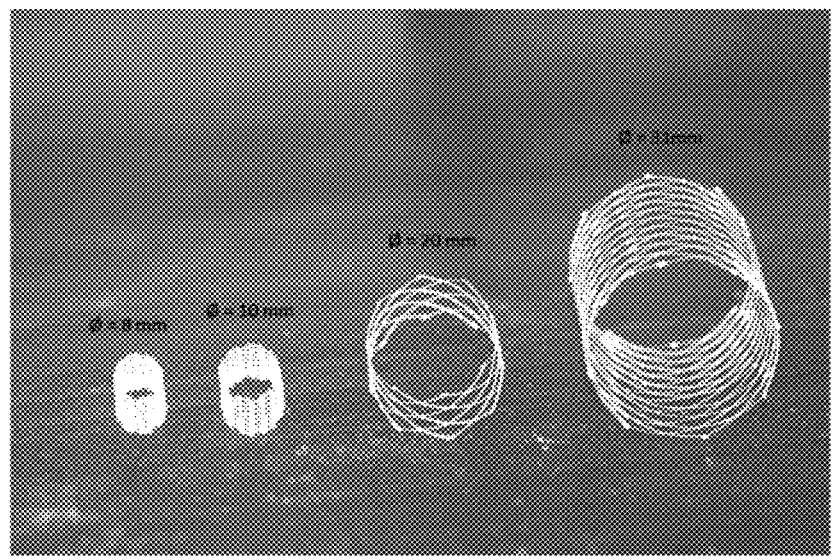
FIG. 16 is a photograph of an 8 mm diameter scaffold, a 10 mm diameter scaffold, a 20 mm diameter scaffold and a 31 mm diameter scaffold, each with 16 strands, in accordance with embodiments of the present disclosure.

The braided PLGA scaffolds were coated with a support coating made from poly(L-lactide-co-ε-caprolactone) (PLCL) cured with hexamethylene diisocyanate (HDI) in the presence of 1-dodecanol (DD) as a chain terminator with the optional use of a catalyst. In particular, a four-arm hydroxyl terminated PLCL (40:60) (mol/mol), HDI, and DD were dissolved in dichloromethane to make a stock solution for spray-coating. The solution was spray-coated onto the braided scaffolds. After thoroughly curing at elevated temperatures, the scaffolds were cut into various lengths for radial force and recovery testing. FIG. 16 shows the macroscopic images of 8 mm, 10 mm, 20 mm and 31 mm scaffolds, each with 16 strands and a braid angle of approximately 100-135 degrees. Some properties of these and analogous scaffolds with different manufactured diameters, numbers of strands, and braid angles are compiled in Table 1 (wherein @[D0-1] mm refers to measurement 1 mm below the manufactured diameter, i.e. 6 mm for the 7 mm scaffolds, 7 mm for the 8 mm scaffolds, and 9 mm for the 10 mm scaffolds). All scaffolds have shown excellent diameter recovery (Rec. %) after simulated use. They have variable radial stiffness (RRF and COF) depending on the design.

TABLE 1

| Entry | Diameter (mm) | Filaments | Filament diameter (in) | Braid angle (deg) | Mass (mg/mm) | RRF/COF@[$D_0$ – 1] mm (mmHg) | Rec. % |
|---|---|---|---|---|---|---|---|
| 1 | 7 | 32 | 0.006" | 127 | 2.6 | 492/166 | 97.9 |
| 2 | 7 | 24 | 0.006" | 127 | 2.1 | 436/133 | 98.1 |
| 3 | 7 | 16 | 0.006" | 127 | 1.6 | 363/66 | 97.9 |
| 4 | 8 | 32 | 0.006" | 127 | 2.6 | 431/66 | 98.8 |
| 5 | 8 | 16 | 0.006" | 127 | 1.6 | 251/18 | 99.3 |
| 6 | 10 | 32 | 0.006" | 127 | 2.6 | 175/30 | 98.4 |
| 7 | 10 | 32 | 0.006" | 110 | 2.0 | 54/10 | 98.6 |
| 8 | 10 | 16 | 0.0065" | 127 | 1.8 | 99/4 | 97.4 |
| 9 | 10 | 16 | 0.0065" | 110 | 1.4 | 31/4 | 98.6 |

EXAMPLE 2

The scaffolds prepared in Example 1 were further coated with an additional conformal coating comprising a mixture of PLCL and mometasone furoate (MF) as active agent. The PLCL in the MF-containing coating comprised about 70% (mol %) lactic acid, with the balance being caprolactone (PLCL 70:30). A homogenous solution of MF and PLCL was prepared in dichloromethane (DCM). Then, the DCM solution was spray-coated onto a 7 mm scaffold with 24 strands.

Figure 17A:
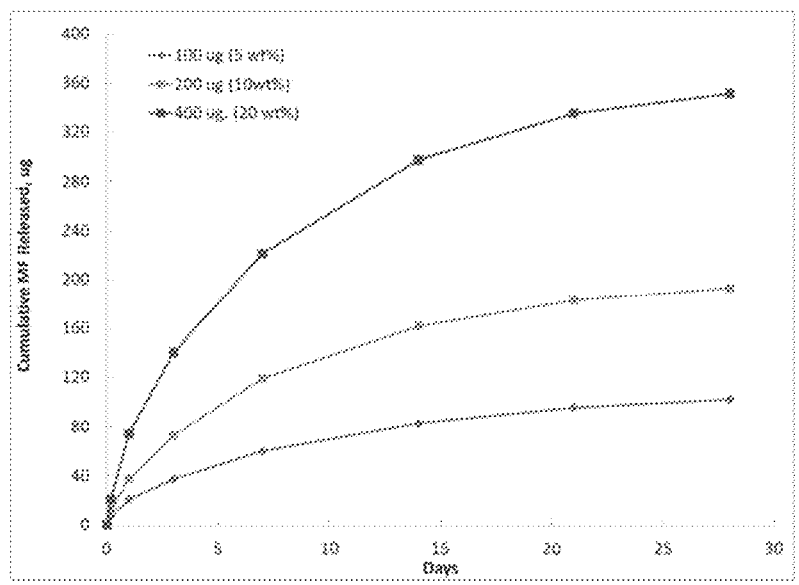
FIG. 17A is a graph illustrating cumulative absolute mass of mometasone furoate (MF) released in the presence of poly(lactic acid-co-caprolactone) (PLCL) as the drug carrier polymer as a function of time for three different drug loadings, in accordance with embodiments of the present disclosure.
Figure 17B:
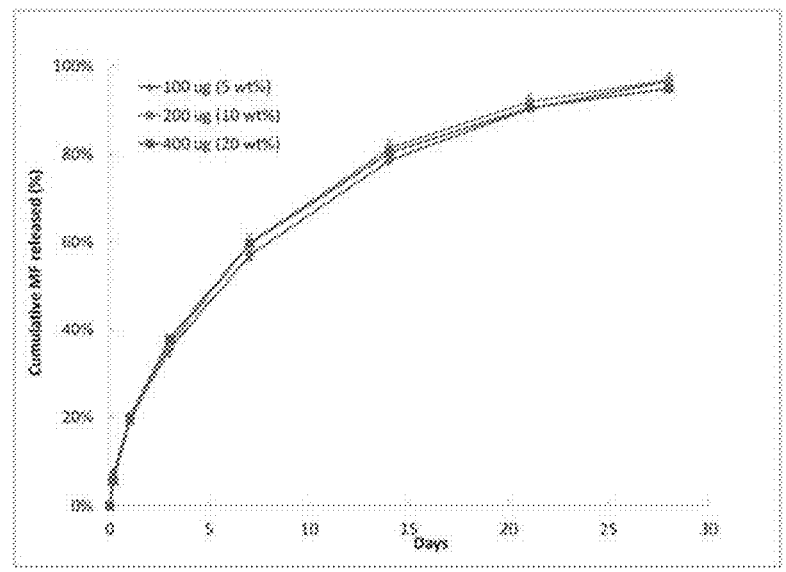
FIG. 17B is a graph illustrating cumulative percent mass of MF released in the presence of PLCL as the drug carrier polymer as a function of time for the embodiments of FIG. 17A.

The amount of MF carried by each scaffold was controlled by the thickness and loading rate of the MF-containing coating. By controlling thickness to between <1 µm to 10 µm and loading rate from about 1 wt % to about 40 wt % MF relative to total dry coating weight, the inventors have found a drug loading for a 7 mm diameter scaffold to beneficially be about 10 to 2400 µg per 10 mm of scaffold length, more beneficially 100 to 1600 µg per 10 mm of scaffold length. FIG. 17A shows the cumulative MF released in mass for scaffolds with different drug loading rates (5, 10 and 20 weight % corresponding to 100, 200 and 400 µg MF per 10 mm of scaffold length. Significantly, the inventors found that the percentage drug release profiles are marginally affected by the drug-loading rates within a certain range (see FIG. 17B).

EXAMPLE 3

Figure 18:
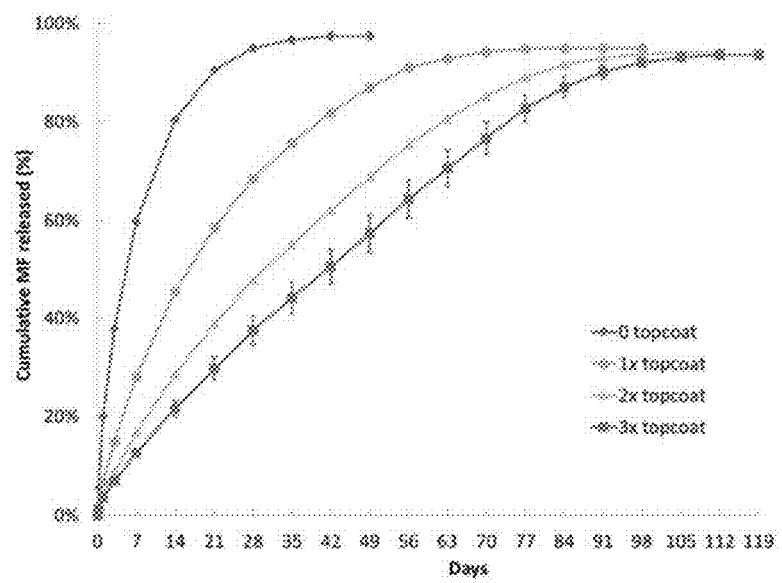
FIG. 18 is a graph illustrating cumulative percent mass of MF released in the presence of PLCL as the drug carrier polymer, with and without a topcoat comprising PLCL and PLA, as a function of time for one 400 µg MF scaffold with no topcoat and three 400 µg MF scaffolds with different topcoat thicknesses, in accordance with embodiments of the present disclosure.

To provide more linear release profiles, a topcoat comprising PLCL (70:30) and PLA was further coated onto the drug coated scaffolds. A homogenous solution of 0.75 wt % PLCL and 0.25 wt % PLA was prepared in DCM. Then, the DCM solution was spray-coated onto a 7 mm scaffold with 24 strands in a single coating layer with variable coating passes resulting in different top coat thickness. As shown in FIG. 18, the MF release can be tuned by changing the thickness of topcoat. The thicker is the topcoat, the slower is the drug release. In combination of this approach with different drug loading rate, it is readily to provide different daily dosage with programmable release duration.

EXAMPLE 4

Biodegradable polymers such as D,L-PLGA have also be used as the drug carrier. Conformal coatings comprising a mixture of D,L-PLGA and mometasone furoate (MF) as active agent were formed. The coatings contained 20 wt % MF. The D,L-PLGA in the mometasone-containing coating comprised D,L-PLGA having about 50% lactide and 50% ε-caprolactone (50:50) (mol %), D,L-PLGA having about 75% lactide and 25% ε-caprolactone (75:25) or D,L-PLGA having about 85% lactide and 15% ε-caprolactone (85:15). In each case a homogenous solution of MF and D,L-PLGA was prepared in anisole/ethyl formate (50:50 v/v). Then, the solution was spray-coated onto a 7 mm scaffold with 24 strands.

Figure 19:
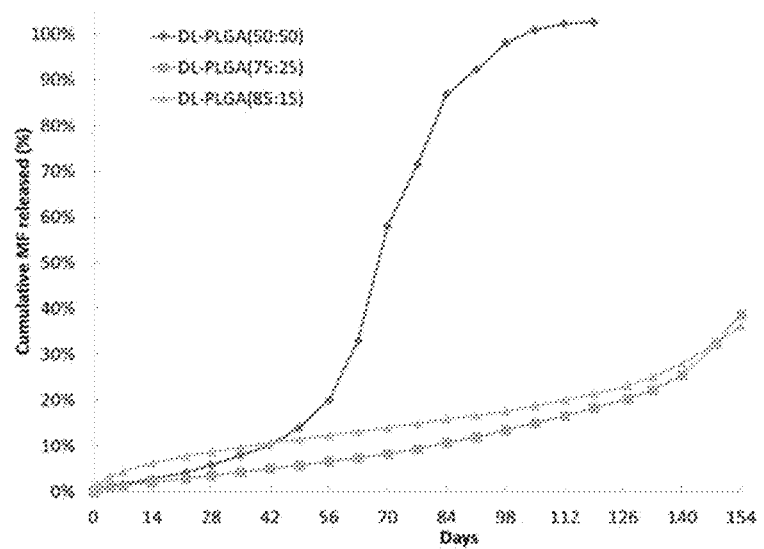
FIG. 19 is a graph illustrating cumulative percent mass of MF released in the presence of D,L-PLGA as the drug carrier polymer as a function of time for 400 µg MF scaffolds containing three different types of D,L-PLGA, in accordance with embodiments of the present disclosure.

As exemplified in FIG. 19, the drug released from the scaffolds with these polymers as the coating layer is drastically slower than that coated with PLCL(70:30). In the case of D,L-PLGA, and without wishing to be bound by theory, the drug release is most likely controlled by the degradation of the carrier polymer, with drug molecules to be released in a later stage after the polymer starts to degrade.

In this context, a scaffold with dual layers of drug coating can be manufactured to achieve sustainable release of MF over a long period of time. For example, a top layer comprising PLCL(70:30) and MF may be formed over a bottom layer comprising DL-PLGA and MF. Without wishing to be bound by theory, in the early stage, it is believed that drug released would be dominated by the diffusion-controlled release of MF from the top layer, whereas in the later stage, the drug in the bottom layer would be released in association with the degradation of DL-PLGA.

EXAMPLE 5

A scaffold consisting of 16 monofilament strands (0.0065" filament diameter, PLGA 85:15) was braided onto a large diameter mandrel (3.175 cm) in a 1×1 braid pattern at 25 picks per inch. The scaffolds were then annealed at 130° C. for 24 hours, cut to a working length and then placed onto fixtures in preparation for spray coating.

Figure 20A:
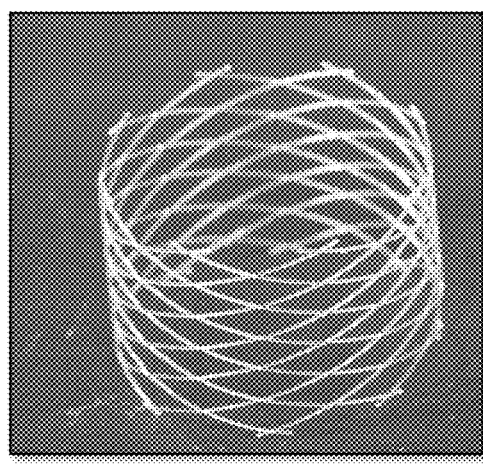
FIG. 20A is a photograph of a 31.75 mm scaffold with 16 strands, in accordance with an embodiment of the present disclosure.
Figure 20B:
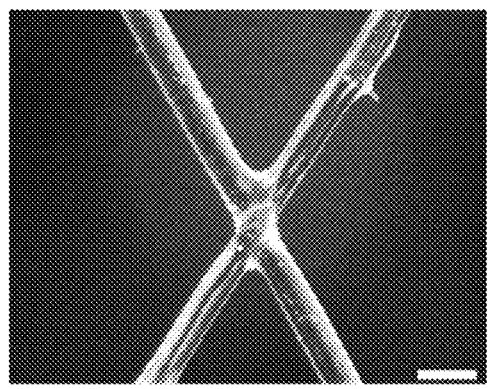
FIG. 20B is a photograph of a coated node of a scaffold like that of FIG. 20A.

An elastomer solution was prepared using 5 wt % PLCL (40:60) dissolved in DCM. A crosslinker, hexamethylene diisocyanate (45:1 NCO:OH) and zinc octoate catalyst (0.1 wt %) were added to the final solution. The elastomer solution was spray coated onto the scaffold and cured at 100° C. for 24 hrs in an open vial. A photograph of one stent produced in this matter is shown in FIG. 20A and a photograph of a coating node of such as stent is shown in FIG. 20B.

Figure 21:
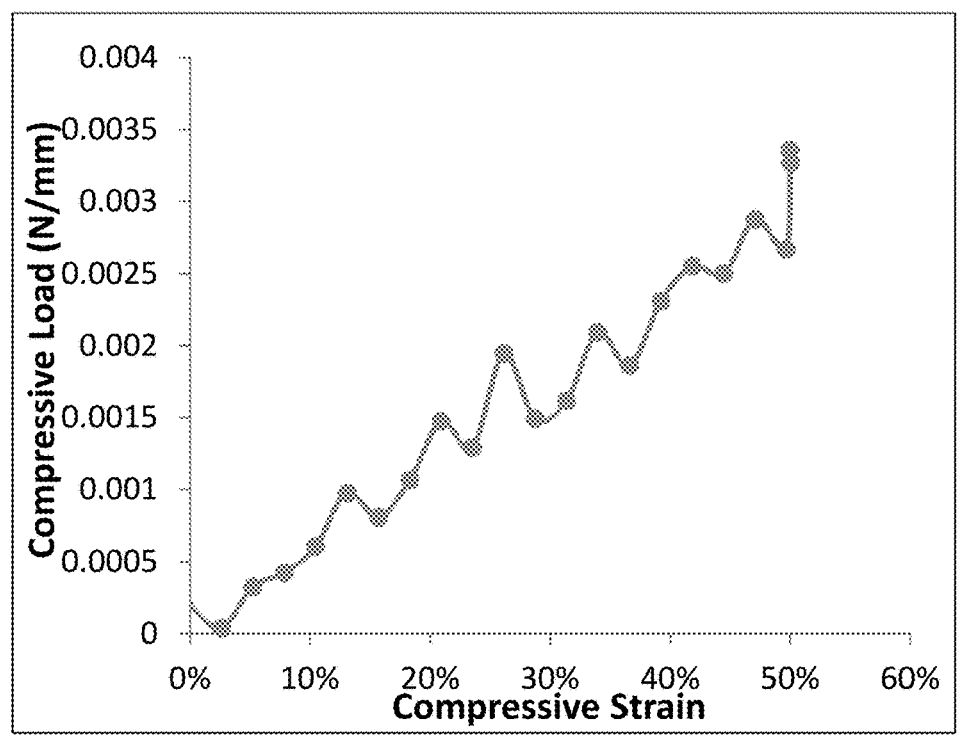
FIG. 21 is a graph illustrating compressive load versus compressive strain for a scaffold in accordance with an embodiment of the present disclosure.

A flat plate compression test was conducted to assess the mechanical performance of the scaffold post curing. The scaffold was compressed longitudinally up to 50% of the initial diameter. The results are shown in FIG. 21, wherein compressive load is per unit length of the scaffold.

EXAMPLE 6

A multifilament strand was prepared by twisting two 0.007" PLGA 85:15 monofilament strands together. The multifilament strand was then hand woven using a fixture into a variety of braid patterns. An example of the fixture used to prepare multifilament scaffold is shown in FIG. 22. The fixture was also used to prepare scaffolds using monofilament strands. After weaving, filament ends were secured to the fixture using tape and subsequently annealed at 100° C. overnight to set the filaments and maintain filament cross-over points. Scaffolds were then spray coated using an elastomer solution containing 5 wt % PLCL 40:60, HDI (45:1 NCO:OH) and zinc catalyst (0.1 wt %) in methylene chloride. All scaffolds were cured at 100° C. for 24 hrs in an open vial.

Table 2 contains data generated from five different braid patterns (shown in FIGS. 22A-22E) after spray coating. All scaffolds were measured for diameter, weight, braid angle, acute recovery and recovery post deployment.

TABLE 2

Figure 22A:
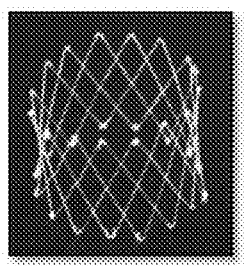
FIGS. 22A-22E are photographs illustrating various scaffold designs, in accordance with various embodiments of the present disclosure.
Figure 22B:
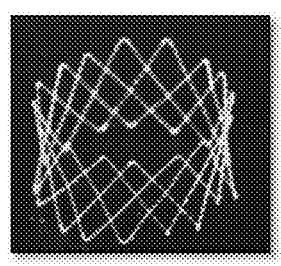
Figure 22C:
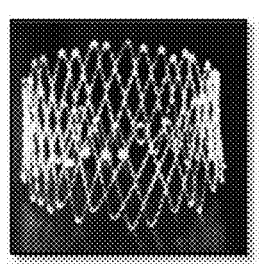
Figure 22D:
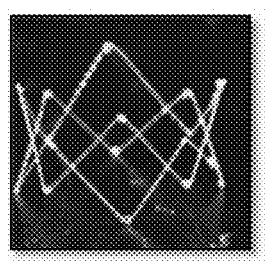
Figure 22E:
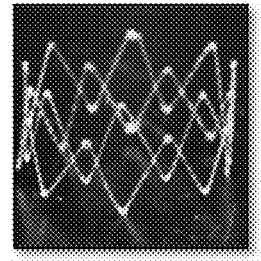
Figures 23A, 23B, 23C, 23D:
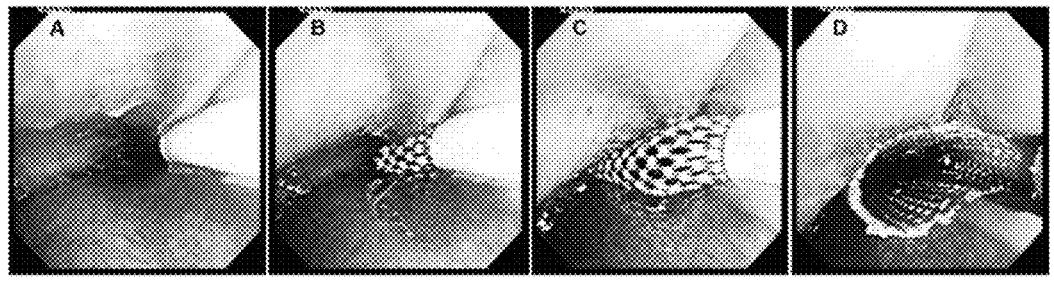
FIG. 23A, FIG. 23B, FIG. 23C and FIG. 23D are photographs illustrating deployment in a swine nasal cavity of a scaffold in accordance with an embodiment of the present disclosure.

| Device | Mono-filament 4 filament braid See FIG. 22A | Twisted multifilament | | | |
|---|---|---|---|---|---|
| | | 4 filament braid See FIG. 22B | 4 filament low braid angle See FIG. 22C | 2 filament braid See FIG. 22D | 2 filament low braid angle See FIG. 22E |
| Mass/length device (mg/mm) | 3.8 | 5.5 | 10 | 2.9 | 3.8 |
| Mass (mg) | 77.0 | ~110 | 203 | 57.4 | 76.6 |
| Braid angle | ~75 | ~70 | ~45 | ~80 | ~50 |
| Device diameter (mm) | ~38 | ~38 | ~38 | ~38 | ~38 |
| Acute recovery | 83% | 60% | Buckled (non-circular recovery) | 78% | 85% |
| Recovery (>10 mins post-deploy) | 85% | 68% | | 90% | 85% |

Recovery testing was performed by crimping and transferring the scaffolds through a series of large to small tubes using an outer braided mesh sheath until a crimp diameter of 4-5 mm was reached. The acute recovery and post deployment recovery is reported as a percentage of the initial diameter.

EXAMPLE 7

In vivo performance of a scaffold in accordance with the present disclosure was examined within a swine cadaver. This study utilized a scaffold in accordance with the present disclosure, approximately 7 mm in diameter and having a 32 filament braid (ref. Table 1, entry 1), and delivered through a 7.5F catheter.

Figure 24:
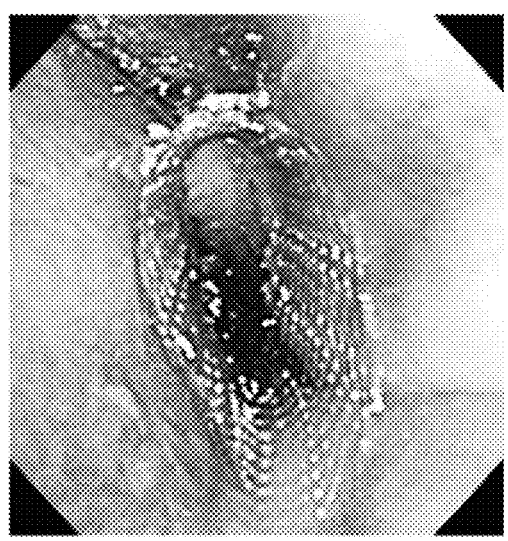
FIG. 24 is a photograph illustrating a scaffold in accordance with an embodiment of the present disclosure following deployment in a swine nasal cavity.

The device was implanted into folds of the nasal turbinate of a swine cadaver. The scaffold deployed in the swine nasal cavity in a smooth, controlled fashion by withdrawing the device outer sheath while holding a middle pusher in place. FIG. 23A, FIG. 23B, FIG. 23C and FIG. 23D are photographs illustrating the deployment process. The delivery catheter was approximately 2.8 mm in diameter. The scaffold expanded to fill the space between the nasal septum and a nasal turbinate as seen in FIG. 24.

These deployments identified some potential benefits of the scaffolds of the present disclosure, including: (a) controlled, accurate delivery, (b) improved apposition/conformability to nasal cavity walls and (c) reduced device profile.

EXAMPLE 8

A human cadaver study was conducted to assess the clinical performance of scaffolds in accordance with the present disclosure in the human anatomy. Device prototypes and delivery system prototypes were integrated to test multiple scenarios within the representative anatomy, both before and after functional endoscopic sinus surgery. Endpoints included visual appearance via endoscopy and clinical feedback.

Several small diameter scaffold prototypes in accordance with the present disclosure are described in Table 1, while two large diameter scaffold prototypes are described in Table 3.

TABLE 3

| Design | Mass (mg) | Diameter (cm) | Length (mm) | Filaments | Filament diameter (in) | Braid angle (deg) | Number of scaffolds | Load at 50% compression (N) | % Recovery |
|---|---|---|---|---|---|---|---|---|---|
| 2 filament braid offset | 60 | ~3.8 | 20 | 2 | 0.0075" twisted | 50 | 1 | 0.034 | 85 |
| 4 filament braid (monofilament) | 77 | ~3.8 | 20 | 4 | 0.0075" | 70 | 1 | 0.032 | 85 |

Figure 25:
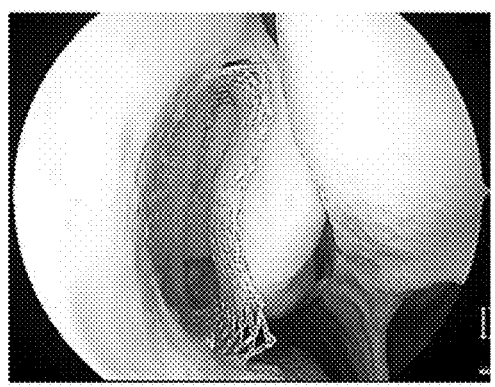
FIG. 25 is a photograph illustrating a 32 filament scaffold having a diameter of 13 mm diameter and a length of 10 mm, in accordance with an embodiment of the present disclosure, following deployment in the native middle meatus of a human cadaver.

Scaffolds formed using procedures along the lines described in Example 1 were placed in the middle meatus, providing mechanical force to displace the middle turbinate medially and demonstrating the potential to deliver drug to the ethmoid sinuses. Five deployments were conducted: (a) a 16 filament, 8 mm scaffold, (b) a 32 filament, 8 mm scaffold, (c) a 16 filament, 10 mm scaffold, (d) a 32 filament, 10 mm scaffold and (d) a 32 filament, 13 mm scaffold. Although all devices conformed relatively well to the tissues, displacing the middle turbinate medially (MT) and providing outward force on the uncinate process (UP) laterally, the 32 filament, 13 mm scaffold appeared to provide the best fit for the particular space into which it had been implanted. FIG. 25, is a photograph illustrating the 32 filament, 13 mm scaffold (length of 10 mm) following deployment in the middle meatus of a human cadaver. The implant conformed well to the tissues with appropriate medialization of middle turbinate.

Figure 26:
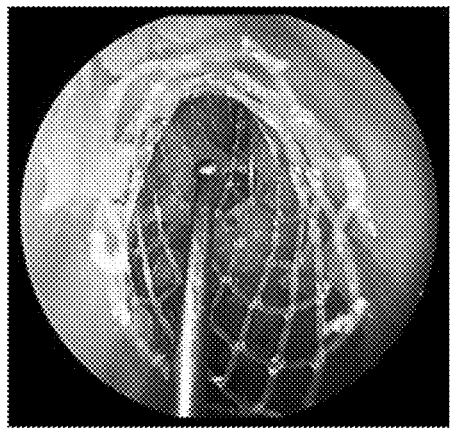
FIG. 26 is a photograph illustrating a 16 filament, 10 mm scaffold in accordance with an embodiment of the present disclosure following deployment in the frontal sinus ostia of a human cadaver.

Devices in accordance with the present disclosure were also placed in the frontal recesses of human cadavers. In a first cadaveric specimen, the frontal recess could not be accessed prior to surgical intervention. The ostia to the frontal sinus was approximately 1 mm in diameter and could not accommodate the delivery device. Functional endoscopic sinus surgery (FESS) was conducted to remove ethmoid cells and expand the passage to the frontal sinus. Following this procedure, 32 filament (Table 1, entry 6) and 16 filament (Table 1, group 8) implants were deployed into the fontal sinus ostia. Although both devices conformed well to the tissue, 16 filament device appeared to exhibit enhanced conformance for the particular space into which it had been implanted. FIG. 26 is a photograph illustrating the 16 filament, 10 mm scaffold following deployment in the frontal sinus ostia.

In a second cadaver, the frontal sinus ostia was accessible prior to surgical intervention. 10 mm, 16 filament implants (n=1 from Table 1, entry 8 and n=1 from Table 1, entry 9) were deployed into the frontal sinus before and after FESS, respectively. These implants conformed well to the sinus ostia.

Figure 27:
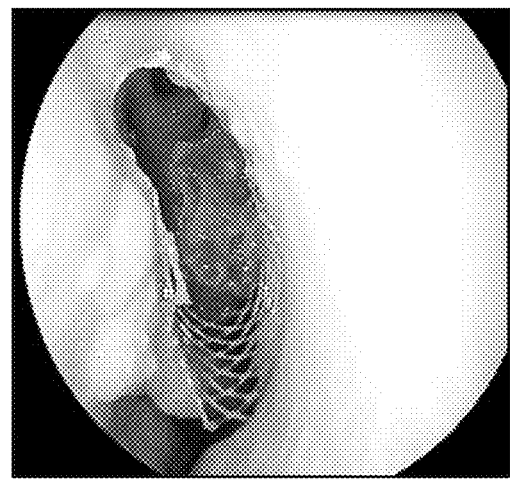
FIG. 27 is a photograph illustrating a 32 filament scaffold having a diameter of 17.5 mm and a length of 10 mm, in accordance with an embodiment of the present disclosure, following deployment in the ethmoid sinus of a human cadaver following FESS.

A 16 filament, 10 mm diameter scaffold, a 4 filament, 38 mm scaffold, a 2 filament, 38 mm scaffold, and a 32 filament, 17.5 mm scaffold were placed the ethmoid sinus of human cadavers following functional endoscopic sinus surgery, with the 10 mm diameter scaffold appearing to be undersize for the particular space into which it had been implanted, the 38 mm scaffolds appearing to be oversize for the particular space into which it had been implanted, and with the 17.5 mm scaffold appearing to provide the best fit for the particular space into which it had been implanted. FIG. 27, which is a photograph illustrating a 32 filament scaffold having a diameter of 17.5 mm and a length of 10 mm after deployment in the ethmoid sinus following FESS.

This study utilized 7.5 French and 9 French catheter systems. The 7.5F system was used to access all frontal sinuses, while the 9F system was used for device deployments into the ethmoid sinus. Both catheter diameters were acceptable, and devices functioned appropriately during use. A 90-degree bend was appropriate for reaching the frontal sinus. Catheters of this type are described, for example, in "SINUS SCAFFOLD DELIVERY SYSTEMS," Ser. No. 62/186,311, filed on Jun. 29, 2015, which is hereby incorporated by reference.

All devices were easily repositioned using standard tools following deployment. All devices were easily removed from the body.

EXAMPLE 9

Figure 28A:
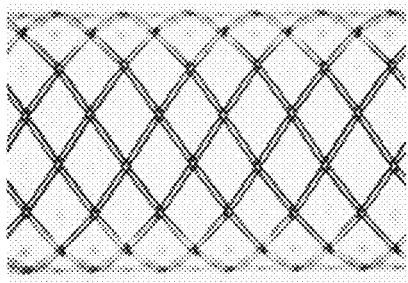
FIGS. 28A-28D are optical microscopic images of coated 8 mm scaffolds having 16 strands with and without anisole as a co-solvent during spray-coating as follows.
Figure 28B:
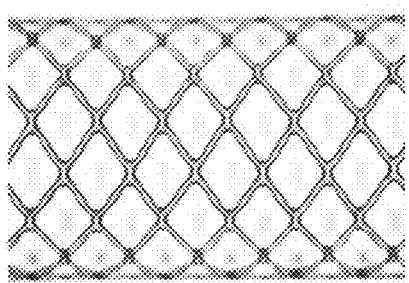
Figure 28C:
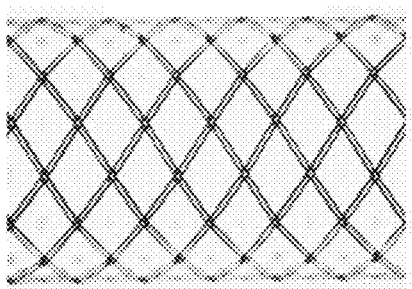
Figure 28D:
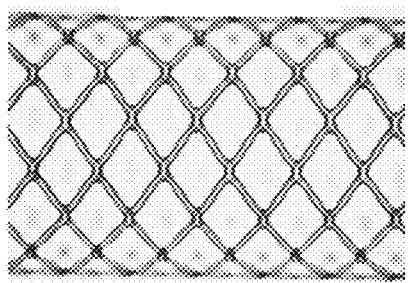

Uniformly braided PLGA(10:90) or PLGA(75:25) scaffolds (diameter=8 mm, 16 strands, having a braid angle of 120°) were coated with a support coating made from poly (L-lactide-co-ε-caprolactone) (PLCL) cured with hexamethylene diisocyanate (HDI) in the presence of 1-dodecanol (DD) as a chain terminator and zinc octoate $(Zn(Oct)_2)$ as a catalyst. More particularly, four-arm PLCL (40:60), HDI, DD, and $Zn(Oct)_2$ were dissolved in dichloromethane (DCM) to make a stock solution for spray-coating. The solution was spray-coated onto the braided scaffolds using standard procedures. After drying at room temperature under a nitrogen environment overnight, the scaffolds were thoroughly cured at 60° C. and then cut into 10 mm length for radial force and recovery testing. To improve the node accumulation of elastomer on the scaffolds, anisole (AN) was used as a co-solvent in the spray-coating solution. After drying and curing treatment as described above, these scaffolds were also subject to mechanical performance evaluation. FIGS. 28A-28D are optical microscopic images of coated 8 mm scaffolds having 16 strands with and without anisole as a co-solvent during spray-coating as follows: FIG. 28A, PLGA(10:90) scaffold without anisole co-solvent; FIG. 28B, PLGA(10:90) scaffold with anisole co-solvent; FIG. 28C, PLGA(75:25) scaffold without anisole co-solvent; and FIG. 28D PLGA(75:25) with anisole co-solvent. Some properties of these scaffolds are compiled in Table 4.

TABLE 4

| Base braid material | Solvent for coating | Wt % of elastomer | RRF/ mmHg (5.5 mm) | COF/ mmHg (5.5 mm) | Rec. % of initial diameter |
| --- | --- | --- | --- | --- | --- |
| PLGA(10:90) | DCM | 93 | 70 | 21 | 98.4 |
| PLGA(10:90) | DCM/AN | 95 | 151 | 65 | 98.5 |
| PLGA(75:25) | DCM | 98 | 70 | 24 | 98.8 |
| PLGA(75:25) | DCM/AN | 96 | 139 | 77 | 99.6 |

Figure 29C:
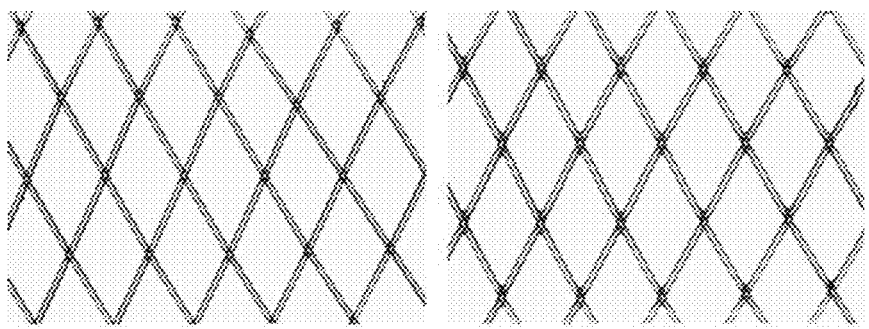
Figure 29C:
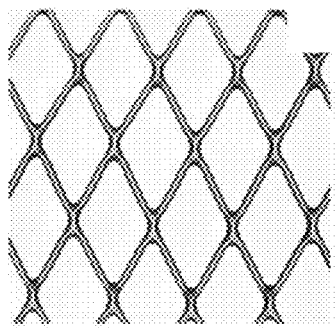

All scaffolds showed excellent diameter recovery after simulated deployment. However, the scaffolds have drastically different radial stiffness depending on the node accumulation of elastomer. The base braid material does not significantly impact the radial stiffness of the coated scaffolds as these two materials have comparable modulus. Similarly, 22 mm diameter PLGA(10:90) scaffolds were coated with the same elastomer in the absence and presence of anisole as a co-solvent during spray-coating as described above. The scaffolds have 32 strands and a braid angle of 128 or 140. FIGS. 29A-29C show optical images of coated scaffolds with and without anisole as a co-solvent during spray-coating as follows: FIG. 29A scaffold coated with 62 wt % elastomer relative to the weight of the base braid (i.e., the ratio between the mass of the elastomer and the mass of the base braid) from solution that does not contain anisole as a co-solvent; FIG. 29B scaffold coated with 63 wt % elastomer relative to the weight of the base braid from solution containing anisole as a co-solvent; and FIG. 29C scaffold coated with 100 wt % elastomer relative to the weight of the base braid from solution containing anisole as a co-solvent. As above, the presence of anisole during scaffold coating improves the node accumulation of the resultant elastomer on the scaffolds. In addition, more coating material would lead to further node accumulation. To evaluate their mechanical performance, these 22 mm diameter scaffolds (Length=10 mm) were subject to compression test in between two parallel flat aluminum plates assembled onto an INSTRON equipment. The scaffolds were compressed to 75% of their initial diameter and the forces at the compression and the rebound stages were recorded as a function of the compressive distance. Table 2 summarizes the compression force (Fc) and the rebound force (Fr) at 50% compression. These forces are normalized to the scaffold length.

TABLE 5

| Braid angle | Solvent for coating | Wt % of elastomer | Fc/ mN mm$^{-1}$ (50% compression) | Fr/ mN mm$^{-1}$ (50% compression) | Rec. % of initial Diameter |
|---|---|---|---|---|---|
| 128 | DCM | 62 | 7.6 | 5.2 | 94.8 |
|  | DCM/AN | 63 | 14.7 | 10.3 | 96.5 |
|  | DCM/AN | 100 | 14.7 | 10.3 | 96.8 |
| 140 | DCM | 87 | 15.5 | 10.8 | 98.1 |
|  | DCM/AN | 82 | 18.9 | 12.6 | 98.5 |
|  | DCM/AN | 118 | 20.8 | 13.4 | — |

It is noted that higher braid angle provides higher compression and rebound force of the scaffold. On the other hand, the node accumulation of the elastomer helps to enhance the stiffness of the scaffolds. However, it has been found that further increasing the quantity of the coating material only marginally improves the compression strength of the scaffolds once a certain level of materials has been introduced onto the nodes.

EXAMPLE 10

In this Example, scaffolds were further coated with an additional conformal coating comprising a mixture of PLCL and mometasone furoate (MF) as active agent. The PLCL in the MF-containing coating comprised about 70% (mol %) lactic acid, with the balance being caprolactone (PLCL 70:30). A homogenous solution of MF and PLCL was prepared in ethyl formate and anisole (50:50 v/v). Then, the solution was spray-coated onto a scaffold of d=10 mm with 16 strands or a scaffold of d=22 mm with 32 strands. The amount of MF carried by each scaffold was controlled by the thickness and loading rate of the MF-containing coating. In the case of 10 mm scaffolds, drug layers containing 20 wt % MF (80 wt % PLCL) and 40 wt % MF (60 wt % PLCL), respectively, have been coated onto the scaffolds to afford 240 µg and 590 µg MF per scaffold, respectively. In another case, 800 µg MF has been coated onto a 22 mm scaffold with 20 wt % MF (80 wt % PLCL) in the drug layer. The drug layer of these 22 mm and 10 mm scaffolds has comparable thickness.

Figure 30A:
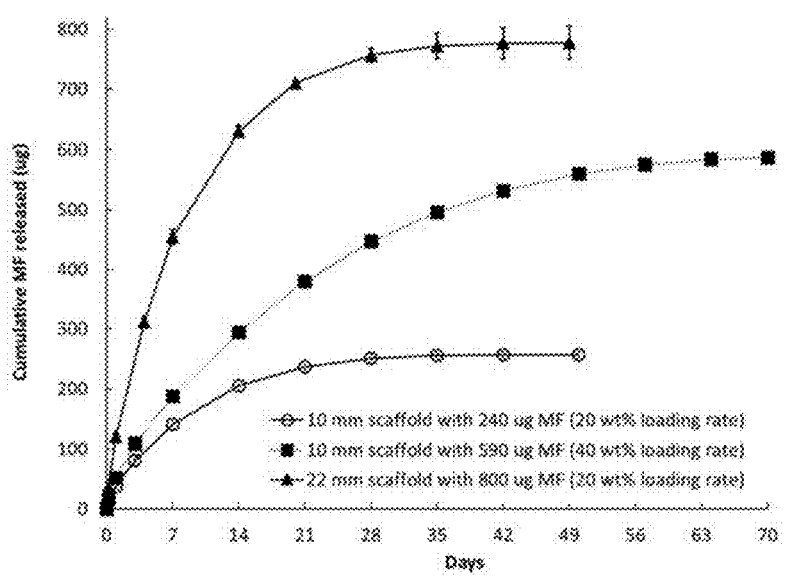
FIG. 30A illustrates cumulative absolute mass of MF released from three sets of MF-coated scaffolds as a function of time.
Figure 30B:
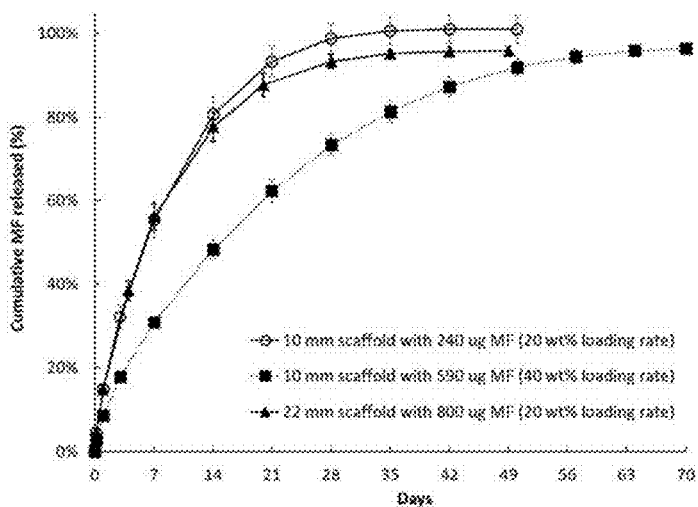
FIG. 30B illustrates cumulative percent mass of MF released from three sets of MF-coated scaffolds as a function of time.

The in vitro release of MF from these MF-coated scaffolds was determined. Each scaffold was incubated in a predefined amount of pH 7.4 PBS buffer with 2% SDS at 37° C. under gentle shaking. At each indicated time point (see FIGS. 30A and 30B), the buffer was removed completely for quantification of MF by HPLC and new buffer was added. FIGS. 30A and 30B illustrate respectively cumulative absolute and percent mass of MF released from these three sets of scaffolds. As expected, the amount of MF released daily depends on the total MF loading in the scaffolds. On the other hand, the 10 mm scaffolds with 40 wt % MF loading rate exhibit significantly slower percent release than their analogs with 20 wt % MF loading rate. This result is different from what the present inventors have observed for scaffolds with relatively low MF loading rates (e.g. from 5 wt % to 20 wt %). It is hypothesized that the high loading rate of MF in the drug coating layer may result in crystallization of MF, consequently leading to slower drug release. In this regard, tailoring drug crystal size is a method of choice to get control over the drug release profile. Interestingly, the 22 mm and 10 mm scaffolds with 20 wt % MF loading rate show essentially identical percent releasing profiles, suggesting that the releasing profile is barely affected by the dimension of the scaffolds when the drug layer has similar thickness.

EXAMPLE 11

Figure 31:
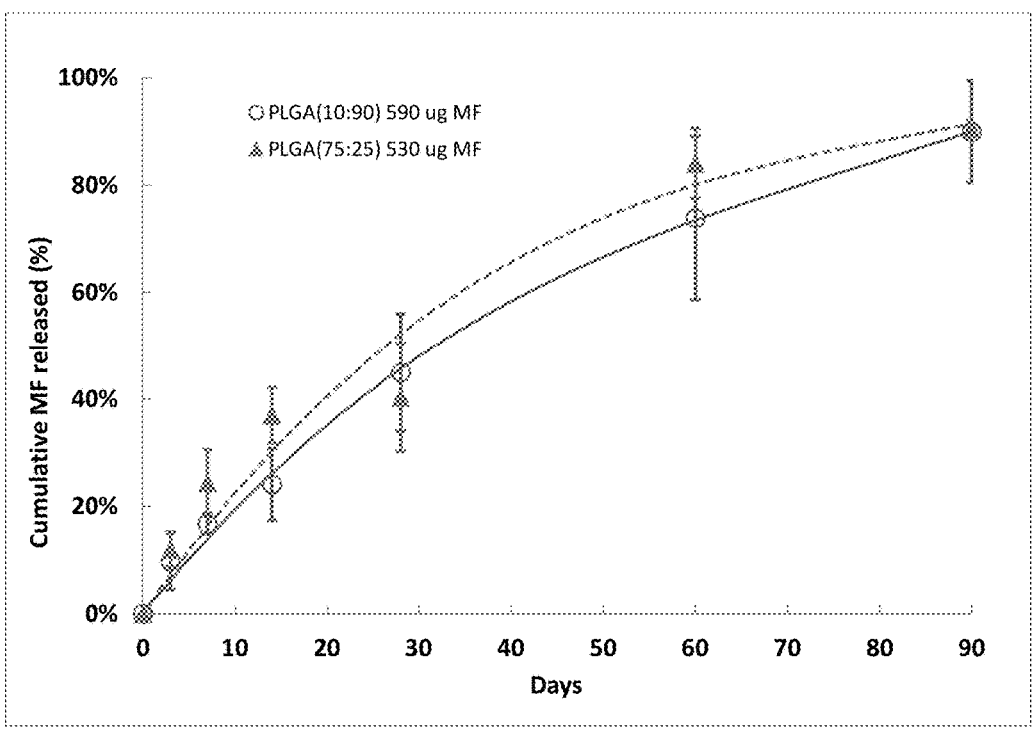
FIG. 31 illustrates in vivo drug release profiles of MF-coated PLGA(10:90) scaffolds and MF-coated PLGA(75:25) scaffolds.
Figure 32:
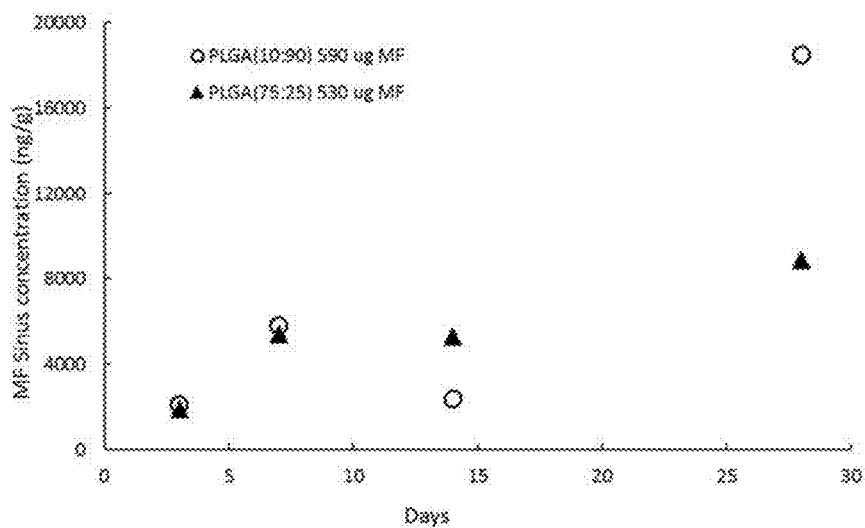
FIG. 32 illustrates MF concentration in the sinus mucosa of sacrificed rabbits as a function of time post-implantation.
Figure 33:
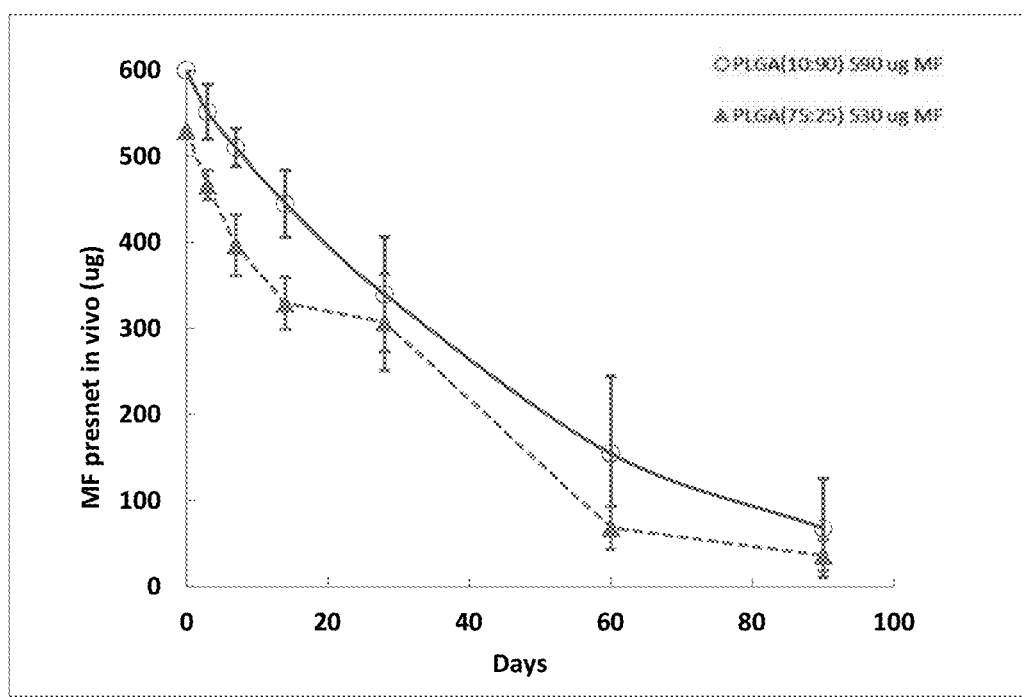
FIG. 33 illustrates total MF in vivo as a function of time (MF on scaffold plus MF in the sinus mucosa of scarified rabbits).

Scaffolds of PLGA (10:90) carrying 590 µg MF and scaffolds of PLGA (75:25) carrying 530 µg MF were manufactured at a diameter of 10 mm and length of 6.5 mm. These scaffolds were sterilized using ethylene oxide and implanted into the left and right maxillary sinus cavities of healthy young, 4-6 month old New Zealand white rabbits. Scaffolds were explanted at 3, 7, 14, and 28 days and analyzed for residual drug content using HPLC-UV. Kinetic drug release (KDR) profiles were generated by subtracting the residual drug from the initially loaded drug determined gravimetrically. The tissue that surrounded the scaffold while deployed was collected and analyzed to obtain the tissue drug concentration. FIG. 31 illustrates the in vivo KDR profiles for MF-coated PLGA(10:90) and PLGA(75:25) scaffolds. FIG. 32 shows the MF concentration in the sinus mucosa of sacrificed rabbits at given time points. FIG. 33 shows the total amount of MF on the scaffold plus the amount of drug in the sinus mucosa of scarified rabbits at given time points.

EXAMPLE 12

Braided PLGA 17.5 mm diameter scaffolds (PLGA 10:90, 32 strands) were coated with a support coating made from poly(L-lactide-co-ε-caprolactone), specifically, L-PLCL (40:60), cured with hexamethylene diisocyanate (HDI) in the presence of 1-dodecanol (DD) as a chain terminator with the optional use of a Zn(Oct)2 catalyst as described above. Then, an additional therapeutic-agent-containing layer comprising 30 wt % MF and 70 wt % PLCL was further coated onto the scaffold from a homogenous solution of MF and PLCL prepared in ethyl formate and anisole (70:30 v/v) as described above, except that D,L-PLCL(80:20) or D,L-PLCL(90:10) was used as the carrier polymer, rather than L-PLCL(70:30) as described above in Example 10.

Figure 34:
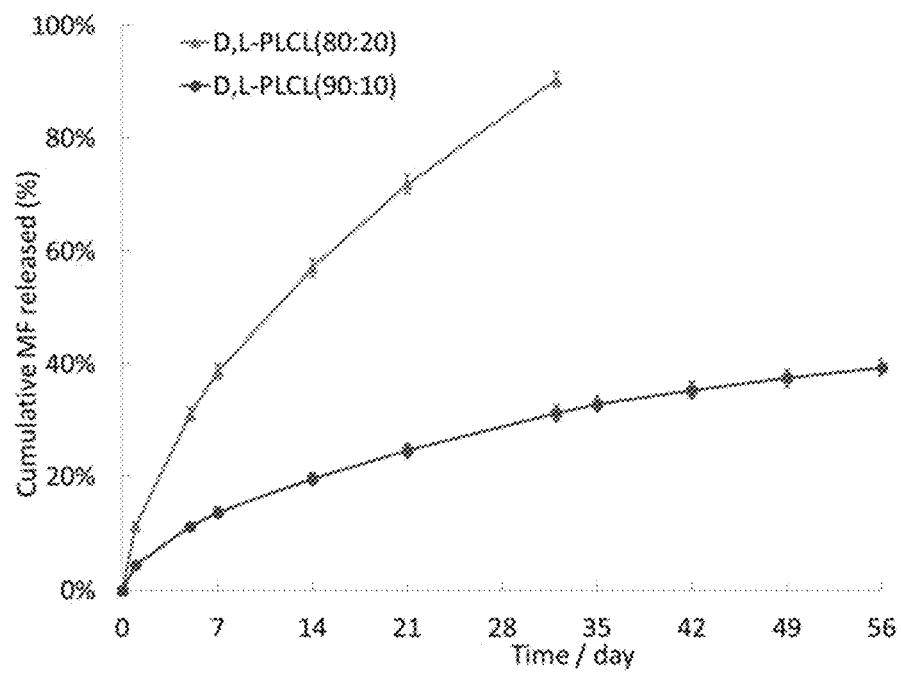
FIG. 34 illustrates cumulative percent mass of MF released from two sets of MF-coated scaffolds as a function of time.

The in vitro release of MF from these MF-coated scaffolds was further determined as described above in Example 10. As shown in FIG. 34, the MF release rate associated with of D,L-PLCL(80:20) (Tg=20° C.) is much faster than that of D,L-PLCL(90:10) (Tg=35° C.). Without wishing to be bound by theory, it is believed that the glass transition temperature (Tg) of the carrier polymer plays an important role in determining the drug release profile. In this regard, in the absence of Tg effects, it would have normally been expected for the copolymer having the least amount of the more hydrophobic monomer (caprolactone), i.e., D,L-PLCL (90:10), to demonstrate the faster release.

EXAMPLE 13

Braided PLGA 17.5 mm diameter scaffolds (PLGA 10:90, 32 strands) were coated with a support coating made from poly(L-lactide-co-ε-caprolactone), specifically, L-PLCL (40:60), cured with hexamethylene diisocyanate (HDI) in the presence of 1-dodecanol (DD) as a chain terminator with the optional use of a catalyst as described above. Then, an additional therapeutic-agent-containing layer comprising 30 wt % MF and 70 wt % polymer material was further coated onto the scaffold from a homogenous solution of MF and polymer material prepared in ethyl formate and anisole (70:30 v/v) as described above, except that in addition to L-PLCL(70:30) as described above in Example 10, the polymeric materials tested further included a blend of PLCL (70:30) and PLGA(75:25) in a 75:25 wt/wt ratio, a blend of PLCL(70:30) and PLGA(85:15) in a 75:25 wt/wt ratio, and a blend of PLCL(70:30) and PLA in a 75:25 wt/wt ratio.

Figure 35:
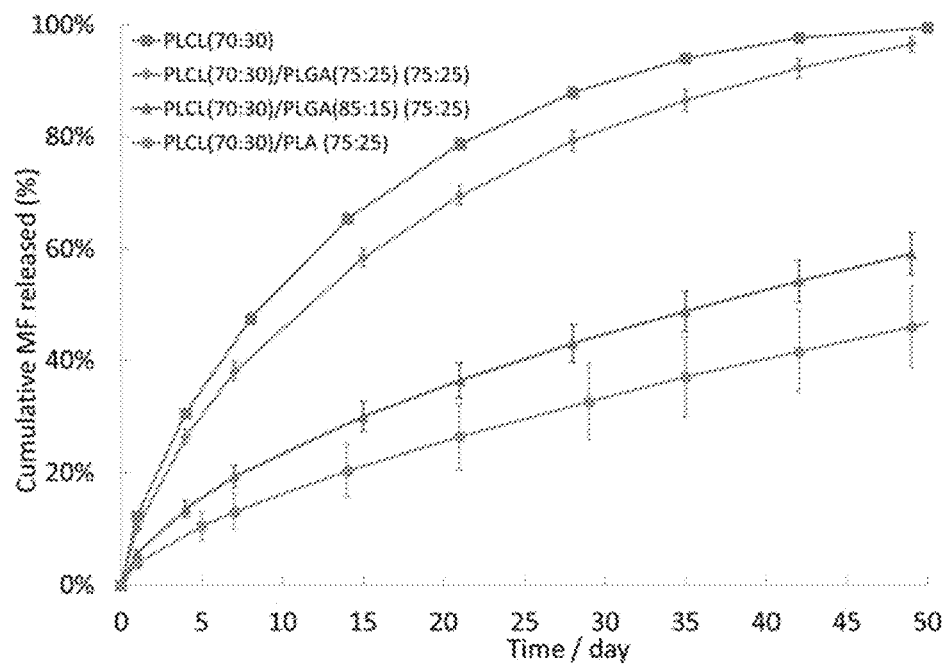
FIG. 35 illustrates cumulative percent mass of MF released from four sets of MF-coated scaffolds as a function of time.

The in vitro release of MF from these MF-coated scaffolds was further determined as described above in Example 10. As shown in FIG. 35, the MF release rate is reduced when copolymers of higher lactide content are blended into PLCL (70:30). Without wishing to be bound by theory, it is believed that MF release rate decreases with increasing Tg of the polymer that is blended with the PLCL(70:30). In this regard, PLA has the highest glass transition temperature among the three polymers used (PLGA(75:25) Tg~50° C., PLGA(85:15) Tg~55° C., and PLA Tg~60° C.).

EXAMPLE 14

Uniformly braided PLGA(10:90) scaffolds (diameter=17.5 mm, length=10 mm, 32 strands, having a braid angle of 90° or 128° were coated with a support coating made from poly(L-lactide-co-ε-caprolactone) (PLCL) cured with hexamethylene diisocyanate (HDI) in the presence of 1-dodecanol (DD) as a chain terminator with the optional use of a catalyst as described above and further coated with a conformal coating comprising a mixture of PLCL and mometasone furoate as described in prior Example 10.

Figure 38:
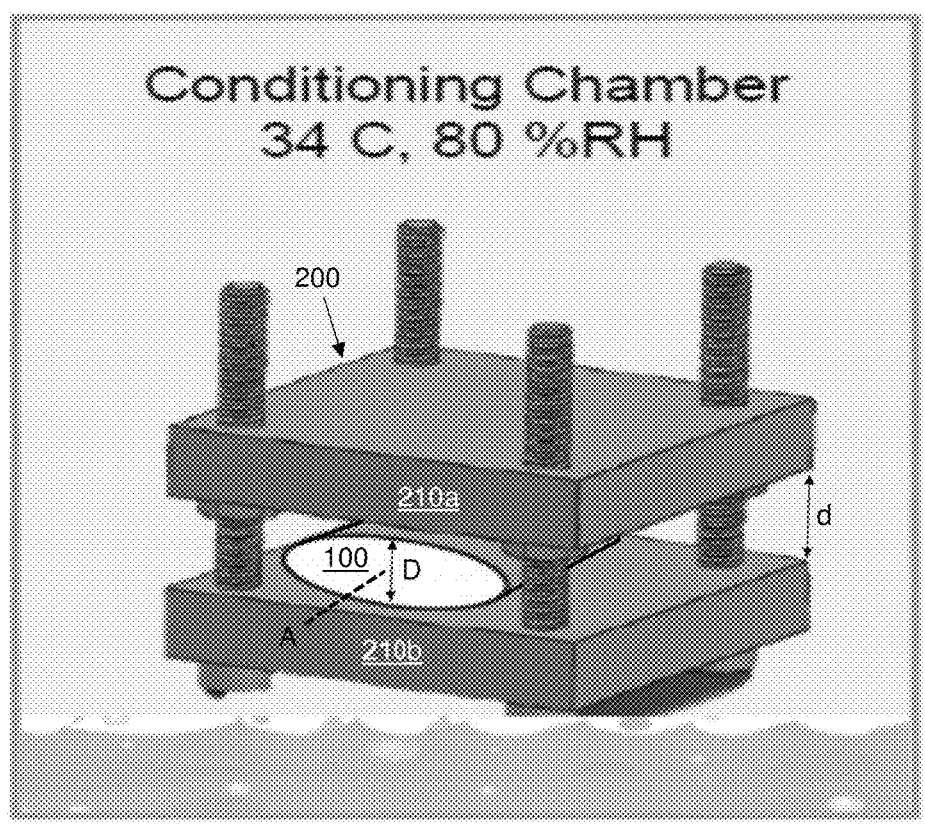
FIG. 38 is a schematic illustration of a testing apparatus for conducting compression testing, in accordance with an embodiment of the present disclosure.

To evaluate their mechanical performance, as shown schematically in FIG. 38, these scaffolds 100 were laid on their sides and compressed in between two parallel flat plates 210a, 210b of a compression apparatus 200 in a chamber maintained at 34° C. and 80% relative humidity. Stated differently, scaffolds 100 were placed in a compressed state between two parallel flat plates 210a, 210b such that the axis A of the tubular scaffold is parallel to the parallel flat plates and such that the tubular scaffold 100 is compressed between the parallel flat plates to a point where a distance d between the parallel flat plates is a percentage of the initial unconstrained diameter such that the tubular scaffold has a first minimum width D measured perpendicular to the axis A that is equal to the distance d, when the scaffold 100 is compressed in the compression apparatus 200 The scaffolds were compressed to either 1.5 mm (8.6% of their initial diameter) or 3 mm (17.1% of their initial diameter). On a weekly basis the scaffolds were removed from the compression apparatus and the recovered minimum width D (also referred to as the second minimum width D) of each scaffold was measured both immediately after removal from the compression apparatus and six hours after removal from the compression apparatus. % recovery is calculated by dividing the second minimum width D immediately after removal or 6 hours after removal from the compression plates by the first minimum width D (which is equal to the distance d across the gap between the parallel plates, i.e. D (in mm)/1.5 mm×100 or D (in mm)/3 mm×100.

In some embodiments, after being maintained in a compressed state for 10 weeks at a distanced that is 8.5% of the manufactured diameter of the scaffold (e.g., a 17.5 mm scaffold compressed to 1.5 mm), and after removal the tubular scaffold 100 from the compressed state for a period of six hours, the first minimum width D of the tubular scaffold (distance d) may recover to a second minimum width D measured perpendicular to the axis that is at least 450% (e.g., 450% to 1000%) of the first minimum width D (theoretical maximum 1166%). In some embodiments, after being maintained in a compressed state for 10 weeks at a distance d that is 17% of the manufactured diameter of the scaffold (e.g., a 17.5 mm scaffold compressed to 3.0 mm), and after removal the tubular scaffold 100 from the compressed state for a period of six hours, the first minimum width D of the tubular scaffold may recover to a second minimum width D measured perpendicular to the axis that is at least 250% (e.g., 250% to 500%) of the first minimum width D (theoretical maximum 583%).

Figure 36A:
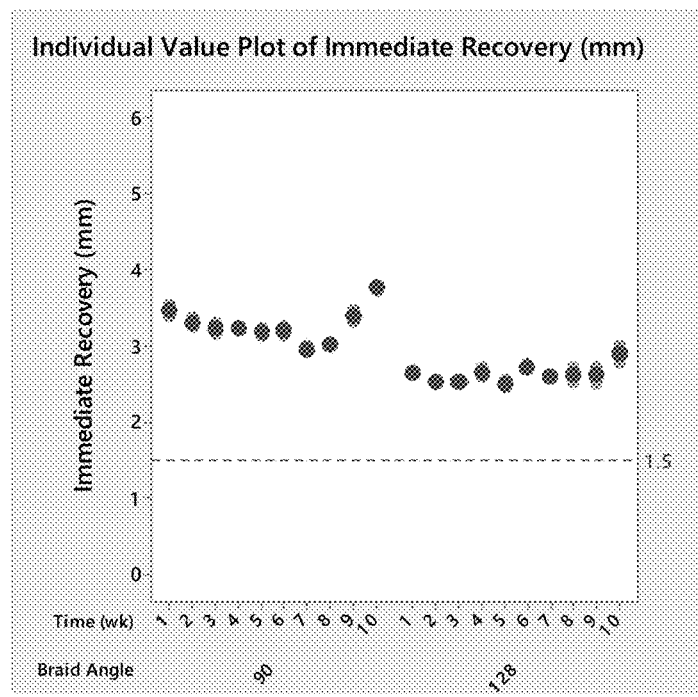
FIG. 36A illustrates immediate recovery from a first amount of compression of two sets of MF-coated scaffolds with 90 and 128 braid angles, as a function of compression time.
Figure 36B:
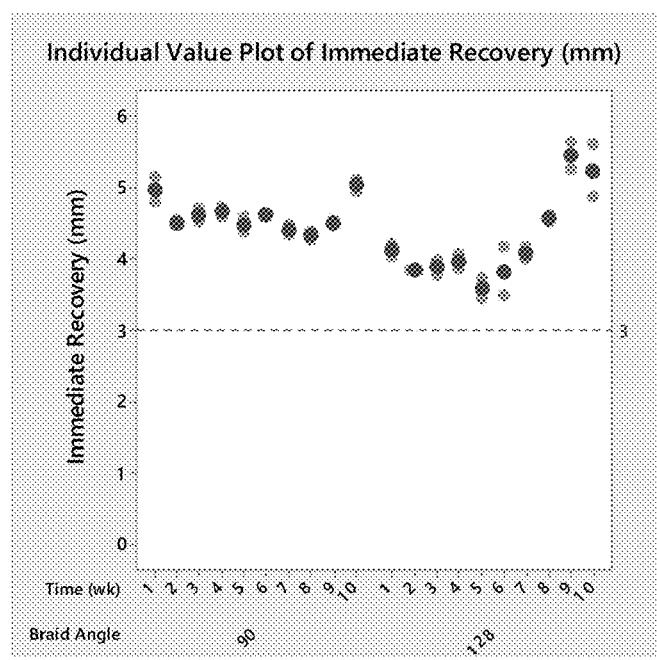
FIG. 36B illustrates immediate recovery from a second amount of compression of two sets of MF-coated scaffolds with 90 and 128 braid angles, as a function of compression time.

Results for the 90° and 128° braid angle scaffolds compressed to 1.5 mm immediately after removal is presented in FIG. 36A and results for the 90° and 128° braid angle scaffolds compressed to 3.0 mm immediately after removal is presented in FIG. 36B. As can be seen from FIG. 36A, the immediate recovery of 90° braid angle scaffolds from 1.5 mm compression is approximately 230% after 1 week and approximately 250% after 10 weeks. The immediate recovery of 128° braid angle scaffolds from 1.5 mm compression is approximately 175% after 1 week and approximately 190% after 10 weeks. As can be seen from FIG. 36B, immediate recovery of 90° braid angle scaffolds from 3.0 mm compression is approximately 165% after 1 week and approximately 170% after 10 weeks. The immediate recovery of 128° braid angle scaffolds from 3.0 mm compression is approximately 140% after 1 week and approximately 175% after 10 weeks.

Figure 37A:
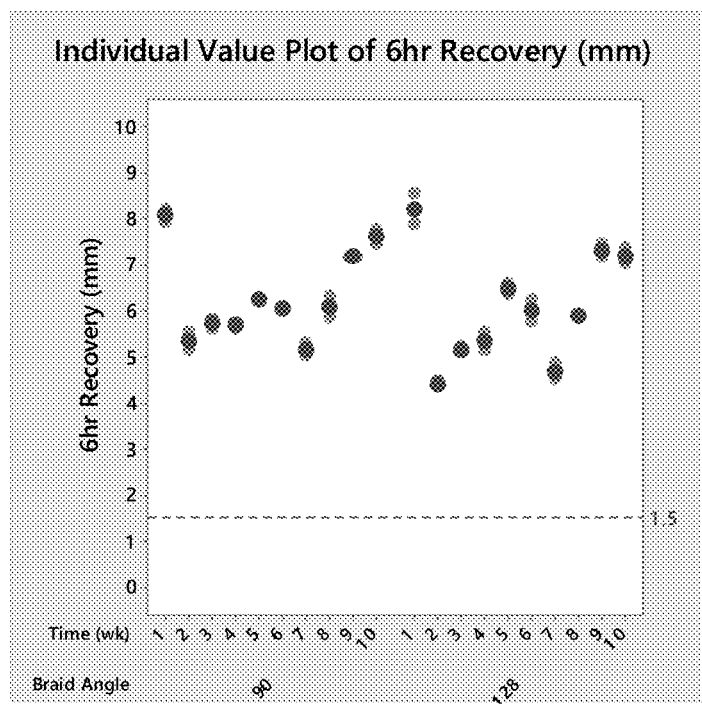
FIG. 37A illustrates six hour recovery from a first amount of compression of two sets of MF-coated scaffolds with 90 and 128 braid angles, as a function of compression time.
Figure 37B:
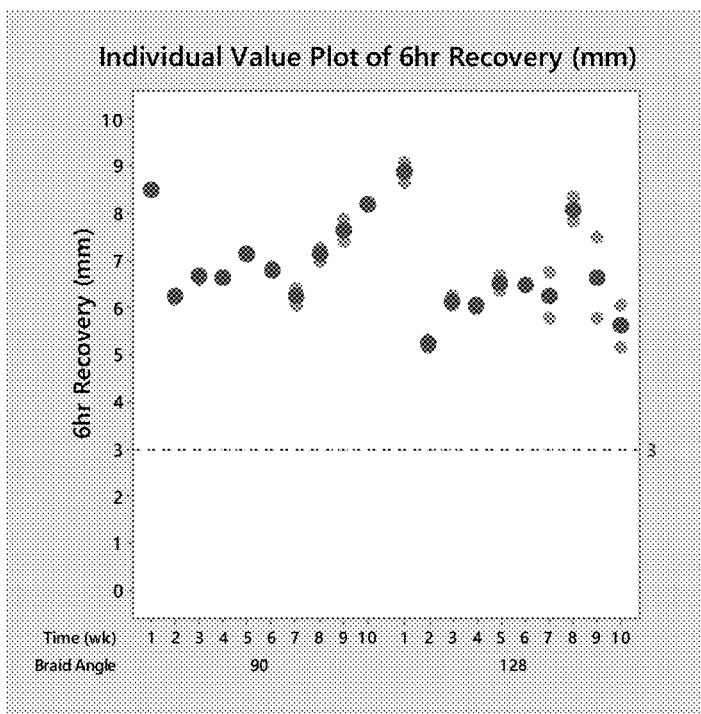
FIG. 37B illustrates six hour recovery from a second amount of compression of two sets of MF-coated scaffolds with 90 and 128 braid angles, as a function of compression time.

Results for the 90° and 128° braid angle scaffolds compressed to 1.5 mm, 6 hours after removal, is presented in FIG. 37A and Table 6, and results for the 90° and 128° braid angle scaffolds compressed to 3.0 mm, 6 hours after removal, is presented in FIG. 37B and Table 7. The 6 hour recovery of 90° braid angle scaffolds from 1.5 mm compression was approximately 540% after 1 week and approximately 510% after 10 weeks. The 6 hour recovery of 128° braid angle scaffolds from 1.5 mm compression was approximately 550% after 1 week and approximately 480% after 10 weeks. The 6 hour recovery of 90° braid angle scaffolds from 3.0 mm compression was approximately 280% after 1 week and approximately 270% after 10 weeks. The 6 hour recovery of 128° braid angle scaffolds from 3.0 mm compression was approximately 300% after 1 week and approximately 190% after 10 weeks.

TABLE 6

| | 1.5 mm Gap - 90 Braid Angle | | 1.5 mm Gap - 128 Braid Angle | |
|---|---|---|---|---|
| | 6 hr Recovery (mm) | 6 hr Recovery (%) | 6 hr Recovery (mm) | 6 hr Recovery (%) |
| 1 wk | 8.09 | 539% | 8.23 | 549% |
| 2 wk | 5.36 | 357% | 4.43 | 295% |
| 3 wk | 5.74 | 383% | 5.16 | 344% |
| 4 wk | 5.7 | 380% | 5.36 | 357% |
| 5 wk | 6.26 | 417% | 6.5 | 433% |
| 6 wk | 6.08 | 405% | 6.01 | 401% |
| 7 wk | 5.17 | 345% | 4.7 | 313% |
| 8 wk | 6.1 | 407% | 5.89 | 392% |
| 9 wk | 7.2 | 480% | 7.33 | 488% |
| 10 wk | 7.62 | 508% | 7.2 | 480% |

TABLE 7

|  | 3 mm Gap - 90 Braid Angle | | 3 mm Gap - 128 Braid Angle | |
| --- | --- | --- | --- | --- |
|  | 6 hr Recovery (mm) | 6 hr Recovery (%) | 6 hr Recovery (mm) | 6 hr Recovery (%) |
| 1 wk | 8.49 | 283% | 8.88 | 296% |
| 2 wk | 6.24 | 208% | 5.24 | 175% |
| 3 wk | 6.67 | 222% | 6.15 | 205% |
| 4 wk | 6.65 | 222% | 6.04 | 201% |
| 5 wk | 7.14 | 238% | 6.52 | 217% |
| 6 wk | 6.81 | 227% | 6.47 | 216% |
| 7 wk | 6.23 | 208% | 6.26 | 209% |
| 8 wk | 7.12 | 237% | 8.09 | 270% |
| 9 wk | 7.65 | 255% | 6.64 | 221% |
| 10 wk | 8.2 | 273% | 5.61 | 187% |

As can be seen from FIG. 37A, recovery of 90° braid angle scaffolds from 1.5 mm compression appears to be similar to recovery of 128° braid angle scaffolds from 1.5 mm compression at all time points, with each showing a substantial drop in recovery between 1 week and 2 weeks. Representative recovery data is provided in Table 6.

Likewise, as can be seen from FIG. 37B, recovery of 90° braid angle scaffolds from 3.0 mm compression appears to be similar to recovery of 128° braid angle scaffolds from 3.0 mm compression out to 7 weeks, with each showing a substantial drop in recovery between 1 week and 2 weeks. Representative recovery data is provided in Table 7.

EXAMPLE 15

Braided PLGA 13 mm diameter scaffolds (PLGA 85:15, 32 strands) were coated with a support coating made from poly(L-lactide-co-ε-caprolactone), specifically, L-PLCL (40:60 mol:mol), cured with hexamethylene diisocyanate (HDI) in the presence of 1-dodecanol (DD) as a chain terminator with the optional use of a $Zn(Oct)_2$ catalyst.

Then, a therapeutic-agent-containing layer comprising 30 wt % MF and 70 wt % PLCL(70:30 mol:mol) was coated onto the scaffold from a homogenous solution of MF and PLCL(70:30) prepared in ethyl formate and anisole. Finally, a topcoat layer of 75 wt % PLCL(70:30) and 25 wt % polylactide (PLA) was further coated onto the scaffold from a solution of PLCL(70:30) and PLA prepared in methylene chloride.

Figure 39:
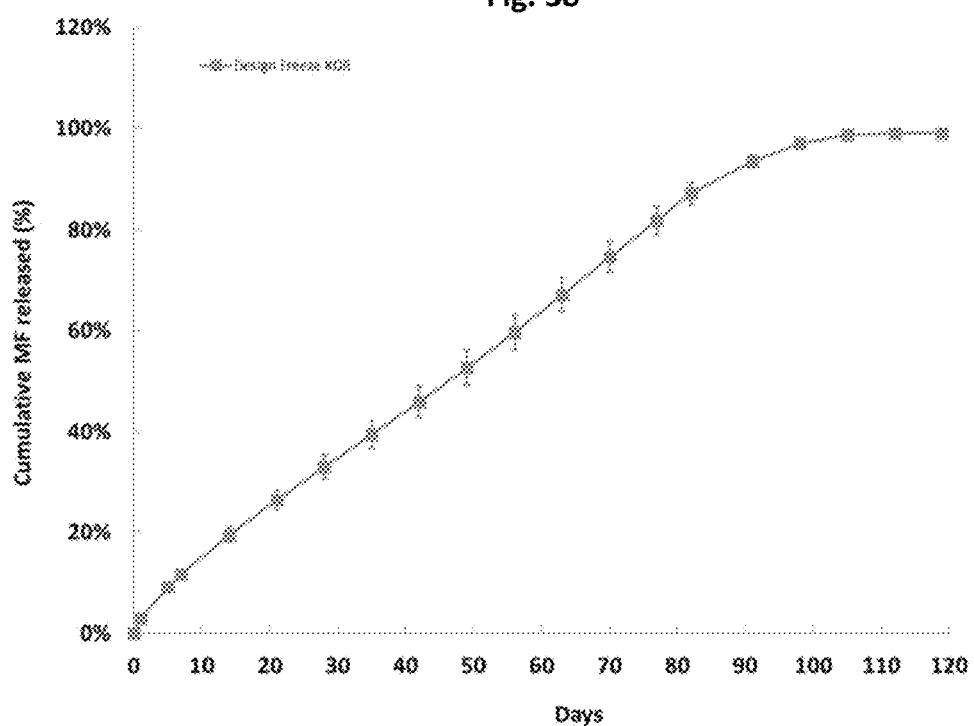
FIG. 39 illustrates cumulative absolute mass of MF released from a set of MF-coated scaffolds as a function of time.

The in vitro release of MF from these MF-coated scaffolds was further determined and is presented in FIG. 39. As shown in FIG. 39, the MF release rate associated with the scaffolds exhibits substantially linear release between 1 and 12 weeks in pH 7.4 PBS buffer containing 2% SDS at 37° C. under gentle shaking. It is noted that release under such conditions has been found to approximately 1.5 to 2 times faster than in vivo release.

Although various embodiments are specifically illustrated and described herein, it will be appreciated that modifications and variations of the present disclosure are covered by the above teachings and are within the purview of the appended claims without departing from the spirit and intended scope of the disclosure. For example, while the scaffolds are described herein for sinus applications, such scaffolds may also be useful for other applications such as Eustachian tube stenting.

What is claimed is:

1. A method of treatment, comprising delivering an expandable scaffold comprising a therapeutic agent to a sinus cavity of a human patient, wherein the scaffold self-expands to a first width within the sinus cavity upon delivery and wherein the scaffold further expands over time to a second width in vivo as the surrounding sinus cavity enlarges such that the scaffold remains in contact with the sinus cavity, and wherein the expandable scaffold is one for which, when submersed in a pH 7.4 PBS buffer solution containing 2 wt % SDS at 37° C. under gentle shaking on a rotary shaker and the buffer solution is removed completely on a weekly basis as a sample for therapeutic agent quantification and replaced with fresh buffer,
    (a) a quantity of therapeutic agent released in each sample, relative to a total amount of therapeutic agent originally in the scaffold, ranges from 1% to 10%, beginning with the second week sample and extending up to the twelfth week sample, or
    (b) a quantity of therapeutic agent released per unit scaffold area in each sample, beginning with the second week sample and extending up to the twelfth week sample, ranges from 0.05 to 4 $\mu g/mm^2$/week, where scaffold area is equal to $\pi DL$, where D is the manufactured diameter of the scaffold and L is the manufactured length of the scaffold, or
    (c) both (a) and (b).

2. The method of claim 1, wherein an absolute quantity of therapeutic agent released in each sample does not vary by more than 33% between any two samples, beginning with the second week sample and extending up to the twelfth week sample.

3. The method of claim 1, wherein the quantity of therapeutic agent released in each sample, relative to a total amount of therapeutic agent originally in the scaffold, ranges from 1% to 10%, beginning with the second week sample and extending up to the twelfth week sample.

4. The method of claim 1, wherein the quantity of therapeutic agent released in each sample, relative to a total amount of therapeutic agent originally in the scaffold, ranges from 5% to 9%, beginning with the second week sample and extending up to the twelfth week sample.

5. The method of claim 1, wherein the quantity of therapeutic agent released in each sample, relative to a total amount of therapeutic agent originally in the scaffold, ranges from 6% to 8%, beginning with the second week sample and extending up to the twelfth week sample.

6. The method of claim 1, wherein the quantity of therapeutic agent released per unit scaffold area in each sample, beginning with the second week sample and extending up to the twelfth week sample, ranges from 0.05 to 4 $\mu g/mm^2$/week.

7. The method of claim 1, wherein the quantity of therapeutic agent released per unit scaffold area in each sample, beginning with the second week sample and extending up to the twelfth week sample, ranges from 0.1 to 1 $\mu g/mm^2$/week.

8. The method of claim 1, wherein the therapeutic agent is mometasone furoate.

9. The method of claim 1, wherein the expandable scaffold comprises (a) a plurality of braided polymeric strands that comprise a biodegradable polymer and (b) a therapeutic agent-containing layer over the braided polymeric strands that comprises the therapeutic agent.

10. The method of claim 9, wherein the braided polymeric strands comprise poly(lactide-co-glycolide).

11. The method of claim 9, wherein the braided polymeric strands comprise poly(lactide-co-glycolide) having a molar percentage of lactide ranging from 82% to 87% and a molar percentage of glycolide ranging from 13% to 18%.

12. The method of claim 9, wherein the therapeutic-agent-containing layer comprises poly(lactic acid-co-caprolactone).

13. The method of claim 9, wherein the therapeutic-agent-containing layer comprises poly(lactic acid-co-caprolactone) and mometasone furoate.

14. The method of claim 9, wherein the expandable scaffold further comprising a topcoat layer over the therapeutic-agent-containing layer that comprises a blend of poly(lactic acid-co-caprolactone) and polylactic acid.

15. The method of claim 14, wherein poly(lactide-co-caprolactone) in each of the therapeutic-agent-containing layer and the topcoat layer has a molar percentage of lactide ranging from 60% to 80% and a molar percentage of caprolactone ranging from 20% to 40%.

16. The method of claim 14, wherein poly(lactide-co-caprolactone) in each of the therapeutic-agent-containing layer and the topcoat layer has a molar percentage of lactide ranging from 65% to 75% and a molar percentage of caprolactone ranging from 25% to 35%.

17. The method of claim 14, wherein the blend comprises from 60 to 80 wt % poly(lactic acid-co-caprolactone) and from 20 to 40 wt % polylactic acid.

18. The method of claim 14, wherein the blend comprises from 70 to 80 wt % poly(lactic acid-co-caprolactone) and from 20 to 30 wt % polylactic acid.

19. The method of claim 14, wherein poly(lactide-co-caprolactone) in each of the therapeutic-agent-containing layer and the topcoat layer has a molar percentage of lactide ranging from 60 to 80% and a molar percentage of caprolactone ranging from 20 to 40%, and wherein the blend comprises from 70 to 80 wt % poly(lactic acid-co-caprolactone) and from 20 to 30 wt % polylactic acid.

20. The method of claim 9, wherein the therapeutic-agent-containing layer comprises between 5 wt % and 50 wt % mometasone furoate.

21. The method of claim 9, wherein the therapeutic-agent-containing layer comprises between 20 wt % and 40 wt % mometasone furoate.

22. The method of claim 14, wherein the therapeutic-agent-containing layer ranges from 10 to 20 μm in thickness and the topcoat layer ranges from 1 to 5 μm in thickness.

23. The method of claim 14, wherein the therapeutic-agent-containing layer ranges from 10 to 16 μm in thickness and the topcoat layer ranges from 1.2 to 2 μm in thickness.

24. The method of claim 9, wherein the expandable scaffold further comprises a support coating disposed over the braided polymeric strands and under the therapeutic agent-containing layer.

25. The method of claim 24, wherein the support coating comprises crosslinked poly(lactide-co-caprolactone).

26. The method of claim 24, wherein the support coating comprises crosslinked poly(lactide-co-caprolactone) having a molar percentage of lactide ranging from 30% to 50% and a molar percentage of caprolactone ranging from 50% to 70%.

27. The method of claim 24, wherein the support coating comprises an isocyanate-crosslinked poly(lactide-co-caprolactone).

28. The method of claim 25, wherein to poly(lactide-co-caprolactone) in the support coating is crosslinked with hexamethylene diisocyanate.

29. The method of claim 1, wherein the second width is 125% of the first width.

30. The method of claim 1, wherein the second width is 150% of the first width.

31. The method of claim 1, wherein the scaffold further expands to the second width over a period of 13 weeks.

32. The method of claim 1, wherein the scaffold further expands to the second width over a period of 26 weeks.

33. The method of claim 1, wherein the scaffold is implanted into a human middle meatus.

34. The method of claim 1, wherein the expandable scaffold is delivered to the native middle meatus using a 2 to 4 mm catheter.

35. The method of claim 1, wherein the expandable scaffold has an unconstrained diameter ranging from 5 to 25 mm at the time of delivery.

36. The method of claim 1, wherein the expandable scaffold has an unconstrained diameter ranging from 9 to 15 mm at the time of delivery.

37. The method of claim 1, wherein the expandable scaffold is selected from the group consisting of an expandable scaffold ranging from 5 to 8 mm in unconstrained diameter at the time of delivery, an expandable scaffold ranging from 7 to 12 mm in unconstrained diameter at the time of delivery, an expandable scaffold ranging from 10 to 15 mm in unconstrained diameter at the time of delivery, an expandable scaffold ranging from 13 to 20 mm in unconstrained diameter at the time of delivery, and an expandable scaffold ranging from 17 to 25 mm in unconstrained diameter at the time of delivery.

38. The method of claim 1, wherein the therapeutic agent is mometasone furoate, and wherein a quantity of mometasone furoate initially present in the scaffold per unit scaffold area ranges from 0.1 μg/mm$^2$ to 20 μg/mm$^2$.

39. A method of treatment, comprising delivering an expandable scaffold comprising a therapeutic agent into the middle meatus of a human patient, wherein the scaffold self-expands to a first width within the middle meatus upon delivery and wherein the scaffold further expands over time to a second width in vivo as the middle meatus enlarges such that the scaffold remains in contact with the middle meatus, and wherein the expandable scaffold is one for which, when submersed in a pH 7.4 PBS buffer solution containing 2 wt % SDS at 37° C. under gentle shaking on a rotary shaker and the buffer solution is removed completely on a weekly basis as a sample for therapeutic agent quantification and replaced with fresh buffer,
  (a) a quantity of therapeutic agent released in each sample, relative to a total amount of therapeutic agent originally in the scaffold, ranges from 1% to 10%, beginning with the second week sample and extending up to the twelfth week sample, or
  (b) a quantity of therapeutic agent released per unit scaffold area in each sample, beginning with the second week sample and extending up to the twelfth week sample, ranges from 0.05 to 4 μg/mm$^2$/week, where scaffold area is equal to πDL, where D is the manufactured diameter of the scaffold and L is the manufactured length of the scaffold, or
  (c) both (a) and (b).

40. The method of claim 39, wherein the expandable scaffold is delivered to the native middle meatus using a 2 to 4 mm catheter.

41. The method of claim 39, wherein an absolute quantity of therapeutic agent released in each sample does not vary by more than 33% between any two samples, beginning with the second week sample and extending up to the twelfth week sample.

42. The method of claim 39, wherein the quantity of therapeutic agent released in each sample, relative to a total amount of therapeutic agent originally in the scaffold, ranges from 1% to 10%, beginning with the second week sample and extending up to the twelfth week sample.

43. The method of claim 39, wherein the quantity of therapeutic agent released in each sample, relative to a total amount of therapeutic agent originally in the scaffold, ranges from 5% to 9%, beginning with the second week sample and extending up to the twelfth week sample.

44. The method of claim 39, wherein the quantity of therapeutic agent released in each sample, relative to a total amount of therapeutic agent originally in the scaffold, ranges from 6% to 8%, beginning with the second week sample and extending up to the twelfth week sample.

45. The method of claim 39, wherein the therapeutic agent is mometasone furoate.

46. The method of claim 39, wherein the expandable scaffold comprises (a) a plurality of braided polymeric strands that comprise a biodegradable polymer and (b) a therapeutic agent-containing layer over the braided polymeric strands that comprises the therapeutic agent.

47. The method of claim 46, wherein the braided polymeric strands comprise poly(lactide-co-glycolide).

* * * * *